US011597967B2

(12) United States Patent
Georgiadis et al.

(10) Patent No.: US 11,597,967 B2
(45) Date of Patent: Mar. 7, 2023

(54) PROCESS FOR MICROSATELLITE INSTABILITY DETECTION

(71) Applicant: PERSONAL GENOME DIAGNOSTICS INC., Baltimore, MD (US)

(72) Inventors: Andrew Georgiadis, Ellicott City, MD (US); Mark Sausen, Baltimore, MD (US)

(73) Assignee: Personal Genome Diagnostics Inc., Baltimore, MD (US)

(*) Notice: Subject to any disclaimer, the term of this patent is extended or adjusted under 35 U.S.C. 154(b) by 0 days.

(21) Appl. No.: 16/204,642

(22) Filed: Nov. 29, 2018

(65) Prior Publication Data

US 2019/0169685 A1    Jun. 6, 2019

Related U.S. Application Data

(60) Provisional application No. 62/593,664, filed on Dec. 1, 2017, provisional application No. 62/741,448, filed on Oct. 4, 2018.

(51) Int. Cl.
| | |
|---|---|
| *C12Q 1/6869* | (2018.01) |
| *C12Q 1/6827* | (2018.01) |
| *C12Q 1/6886* | (2018.01) |
| *G16H 50/20* | (2018.01) |
| *G16B 5/20* | (2019.01) |
| *G16H 50/30* | (2018.01) |
| *G16B 20/00* | (2019.01) |
| *G16B 40/00* | (2019.01) |

(52) U.S. Cl.
CPC ......... *C12Q 1/6869* (2013.01); *C12Q 1/6827* (2013.01); *C12Q 1/6886* (2013.01); *G16B 5/20* (2019.02); *G16B 20/00* (2019.02); *G16B 40/00* (2019.02); *G16H 50/20* (2018.01); *G16H 50/30* (2018.01); *C12Q 2563/185* (2013.01)

(58) Field of Classification Search
None
See application file for complete search history.

(56) References Cited

U.S. PATENT DOCUMENTS

| | | | |
|---|---|---|---|
| 2015/0337388 A1* | 11/2015 | Garner, Jr. ............ | G16C 20/60 506/8 |
| 2016/0251704 A1 | 9/2016 | Talasaz et al. | |
| 2018/0155779 A1* | 6/2018 | Zimmermann ...... | C12Q 1/6806 |
| 2018/0251848 A1* | 9/2018 | Diehn .................. | C12Q 1/6806 |

FOREIGN PATENT DOCUMENTS

| | | |
|---|---|---|
| CN | 106755501 | 5/2017 |
| WO | WO 2014/099979 A2 | 6/2014 |
| WO | WO 2016/077553 A1 | 5/2016 |
| WO | WO 2016/109452 A1 | 7/2016 |
| WO | WO 2017/127742 A1 | 7/2017 |
| WO | WO 2018/093744 A2 | 5/2018 |

OTHER PUBLICATIONS

Gan et al. Applicability of Next Generation Sequencing Technology in Microsatellite Instability Testing. Genes 6:46-59. (Year: 2015).*
Kim et al. A Genome-wide View of Microsatellite Instability: Old Stories of Cancer Mutations Revisited with New Sequencing Technologies. Cancer Res. 74(2): 6377-82. (Year: 2014).*
Liljegren et al. Microsatellite Length Scoring by Single Molecule Real Time Sequencing-Effects of Sequence Structure and PCR Regime. PLoS ONE 11(7): e0159232 (17 pages). (Year: 2016).*
Le et al. PD-1 Blockade in Tumors with Mismatch-Repair Deficiency. The New England Journal of Medicine 372(26):2509-20. (Year : 2015).*
Bettegowda et al. Detection of Circulating Tumor DNA in Early- and Late-Stage Human Malignancies. Sci. Transl. Med. 6:224ra24. (Year: 2014).*
Supplementary Materials for Detection of Circulating Tumor DNA in Early- and Late-Stage Human Malignancies. Sci. Transl. Med. 6:224ra24. (Year: 2014).*
International Search Report dated Feb. 21, 2019, regarding PCT/US2018/063083.
Kim et al.: "*The landscape of microsatellite instability in colorectal and endometrial cancer genomes*,"; Cell, Nov. 7, 2013, vol. 155, No. 4, pp. 858-868.
Phallen et al.: "*Direct detection of early-stage cancers using circulating tumor DNA*,"; Sci Transl Med, Aug. 16, 2017, vol. 9, No. 403, pp. 1-12.
Behjati S., et al., "What is next generation sequencing?", Arch Dis Child Educ Pract Ed 2013;98:236-238. doi:10.1136/archdlschild-2013-304340, Aug. 28, 2013, pp. 1-3.
EP Supplementary European Search Report in European Application No. EP 18 88 3093, dated Jul. 19, 2021, 14 pages.
Gan et al., "Applicability of Next Generation Sequencing Technology in Microsatellite Instability Testing", Genes, Feb. 2015, 6(1):46-49.
Goessl et al., "Microsatellite Analysis of Plasma DNA from Patients with Clear Cell Renal Carcinoma", Cancer Research, Oct. 1998, pp. 4728-4732.

(Continued)

*Primary Examiner* — Samuel C Woolwine
(74) *Attorney, Agent, or Firm* — Kilpatrick Townsend & Stockton LLP

(57) ABSTRACT

The invention provides methods for determining the MSI status of a patient by liquid biopsy with sample preparation using hybrid capture and non-unique barcodes. In certain aspects, the invention provides a method of detecting microsatellite instability (MSI). The method includes obtaining cell-free DNA (cfDNA) from a sample of blood or plasma from a patient and sequencing portions of the cfDNA to obtain sequences of a plurality of tracts of nucleotide repeats in the cfDNA. A report is provided describing an MSI status in the patient when a distribution of lengths of the plurality of tracts has peaks that deviate significantly from peaks in a reference distribution.

32 Claims, 21 Drawing Sheets

(56) References Cited

OTHER PUBLICATIONS

Kim et al., "A Genome-wide View of Microsatellite Instability: Old Stories of Cancer Mutations Revisited with New Sequencing Technologies", Cancer Research, Nov. 2014, 74(22):6377-6382.
Mokarram et al., "Microsatellite instability typing in serum and tissue of patients with colorectal cancer: comparing real time PCR with hybridization probe and high-performance liquid chromatography", Molecular Biology Reports, May 2014, 41(5):2835-2844.
Rawnaq et al., "Monitoring of Loss of Heterozygosity in Serum Microsatellite DNA Among Patients with Gastrointestinal Stromal Tumors Indicates Tumor Recurrence", Journal of Surgical Research, Jul. 2011, 169(1):31-35.
Salipante et al., "Microsatellite Instability Detection by Next Generation Sequencing", Clinical Chemistry, Sep. 2014, 60(9):1192-1199.
Vandekerkhove et al., "Clinical utility of emerging liquid biomarkers in advanced prostate cancer", Cancer Genetics, Aug. 2017, 228-229:151-158.
Vartia et al., "A novel method of microsatellite genotyping-by-sequencing using individual combinatorial barcoding", Royal Society open Science, Jan. 2016, 3(1):150565.

\* cited by examiner

401

PATIENT RESULTS

TEST: CPT
NUMBER OF MARKERS: 5
TARGET BASES: 478,861
SEQUENCED TUMOR BASES: 1,667,418,600
SEQUENCED NORMAL BASES: 822,428,100

SEQUENCE MUTATIONS

CDH1 CHR16 68835670Q>C

AMPLIFICATIONS

EGFR CHR7 55086724-5527503

MSI

MSI-HIGH: BAT25, BAT26, MONO27, NR21, AND NR24

FIG 4.

PROCESS FOR MICROSATELLITE INSTABILITY DETECTION

CROSS-REFERENCE TO RELATED APPLICATIONS

This application claims benefit of priority under 35 U.S.C. § 119(e) of U.S. Ser. No. 62/593,664 filed Dec. 1, 2017, and of U.S. Ser. No. 62/741,448 filed Oct. 4, 2018, the entire contents of which is incorporated herein by reference in its entirety.

TECHNICAL FIELD

The present invention relates generally to the detection, monitoring, and treatment of cancer and more specifically to determining the MSI status of a patient by liquid biopsy.

BACKGROUND

Cancer causes more than a half a million deaths each year in the United States alone. The success of current treatments depends on the type of cancer and the stage at which it is detected. Many treatments include costly and painful surgeries and chemotherapies, and are often unsuccessful. Early and accurate detection of mutations is essential for effective cancer therapy.

Many cancers involve the accumulation of mutations that results from failure of the DNA mismatch-repair (MMR). One important marker of MMR deficiency is microsatellite instability (MSI), a polymorphism of tandem nucleotide repeat lengths ubiquitously distributed throughout the genome. The presence of MMR-deficiency or MSI may serve as a marker for immunotherapy response with checkpoint inhibition. Knowledge of MSI status is thus important and valuable for the treatment of cancer. While it may be possible to determine MSI status by sequencing DNA from a tumor sample, such as a formalin-fixed paraffin-embedded (FFPE) tumor tissue specimen, there are patients for whom tumor material is not readily obtained.

Absent a fixed tissue specimen, a potential source for tumor information is through the analysis of circulating tumor DNA (ctDNA). ctDNA is released from tumor tissue into the blood and can be analyzed by liquid biopsy. Liquid biopsies potentially allow for the detection and characterization of cancer. However, liquid biopsies present their own inherent challenges associated with low circulating tumor DNA (ctDNA) levels as well as problems with faithfully amplifying and sequencing regions of DNA characterized by tracts of mononucleotide repeats.

SUMMARY OF THE INVENTION

The present invention is based on the seminal discovery that a circulating tumor DNA based approach is useful for the detection of high tumor mutation burden and microsatellite instability in cancer patients with advanced disease and can be used to predict responders to immune checkpoint blockade.

The invention provides methods for determining the MSI status of a patient by liquid biopsy. Methods include a sample preparation using hybrid capture and non-unique barcodes. The sample preparation both compensates for errors such as sequencing artifacts and polymerase slippage and provides for the successful capture of target DNA even when present only at a very low fraction of total DNA. Methods include sequencing tracts of mononucleotide repeats within captured sample and modelling the distribution of lengths of those tracts. A peak-finding operation evaluates peaks in the modelled distribution and reveals MSI in the patient when the peaks deviate from a reference distribution (e.g., such as by indicating that the tracts of mononucleotide repeats in the patient's DNA are markedly shorter than in healthy DNA).

Methods of the disclosure are amenable to implementation in conjunction with other genomic screenings such as screening panels of markers, genes, or whole genomes to report mutations or mutational burden. Methods may be implemented by including MSI markers within any suitable liquid-biopsy based sequencing assay and may evaluate MSI status by interrogating MSI markers such as BAT-25, BAT-26, MONO-27, NR-21, and NR-24, BAT-40, TGFβ RII, IGFIIR, hMSH3, BAX and dinucleotide D2S123, D9S283, D9S1851 and D18S58 loci, by way of example, or by modeling distributions of lengths of any other suitable set(s) of repeats in the genome.

In certain aspects, the invention provides a method of detecting microsatellite instability (MSI). The method includes obtaining cell-free DNA (cfDNA) from a sample of plasma from a patient and sequencing portions of the cfDNA to obtain sequences of a plurality of tracts of nucleotide repeats in the cfDNA. A report is provided describing an MSI status in the patient when a distribution of lengths of the plurality of tracts has peaks that deviate significantly from peaks in a reference distribution. Obtaining the cfDNA may include capturing target portions of DNA with probes, fragmenting the target portions to yield fragments, and attaching barcodes to the fragments. In preferred embodiments, the barcodes are non-unique barcodes that include duplicates such that different ones of the fragments are attached to identical barcodes.

The method may include amplifying the fragments to produce amplicons that include barcode information and copies of the fragments, wherein the sequencing step comprises sequencing the amplicons. In one aspect, the sequencing is next-generation, short-read sequencing. The obtained sequences may include a plurality of sequence reads and the method may include aligning the sequence reads to a reference, and identifying groups of sequence reads that originated from a unique segment of the cfDNA by means of the barcode information and position or content of the sequence reads.

The use of the non-unique barcodes to identify groups of sequence reads that originated from a unique segment of the cfDNA allows for the lengths of the plurality of tracts to be determined correctly by correcting for errors introduced by sequencing artifacts or polymerase slippage during the amplifying step.

Preferably, the target portions are markers for MSI such as one or more of BAT25, BAT26, MON027, NR21, NR24, Penta C, and Penta D. For example, the markers may include all of BAT25, BAT26, MON027, NR21, and NR24. In certain embodiments, each of the microsatellite markers is selected from the group consisting of BAT-25, BAT-26, MONO-27, NR-21, NR-24, Penta C, and Penta D, BAT-40, TGFβ RII, IGFIIR, hMSH3, BAX and dinucleotide D2S123, D9S283, D9S1851 and D18S58 loci, by way of example.

In some embodiments, the method includes recommending a treatment for the patient based on the MSI status. Where the MSI status indicates that the patient is microsatellite instable, the treatment may include an immune checkpoint inhibitor. In certain embodiments, the method includes administering the treatment (e.g., the immune checkpoint inhibitor) to the patient. The immune checkpoint inhibitor may be, for example, an antibody such as an anti-PD-1 antibody; an anti-IDO antibody; anti-CTLA-4 antibody; an anti-PD-L1 antibody; or an anti-LAG-3 antibody.

Related aspects provide a method of detecting microsatellite instability (MSI) that includes obtaining a sample comprising fragments of cell-free DNA from a patient; attaching barcodes to the fragments, wherein at least some of the barcodes are not unique; sequencing the barcodes to obtain sequences of a plurality of markers in the DNA; determining a distribution of lengths of the plurality of markers; and providing a report describing MSI in the patient when peaks in the distribution deviate significantly from expected peaks in a modeled healthy distribution.

BRIEF DESCRIPTION OF THE DRAWINGS

FIG. 4 shows a report provided by systems and methods of the invention.

DETAILED DESCRIPTION OF THE INVENTION

Figure 1:
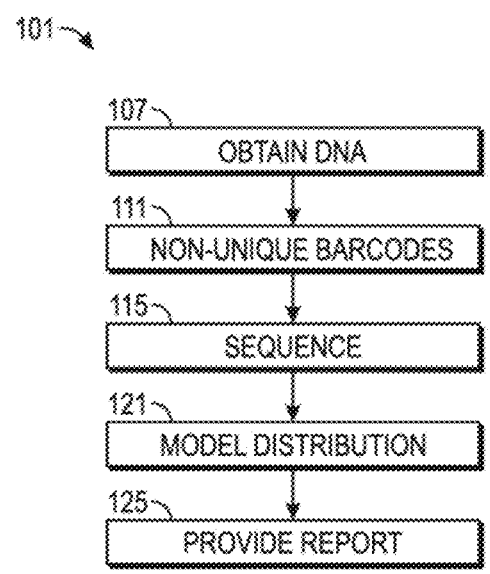
FIG. 1 diagrams a method for determining MSI status.

The present invention relates to the discovery that microsatellite instability (MSI) and high tumor mutation burden (TMB-High) are pan-tumor biomarkers used to select patients for treatment with immune checkpoint blockade. The present invention shows a plasma-based approach for detection of MSI and TMB-High in patients with advanced cancer. To detect sequence alterations across a 98 kilobase panel, including those in microsatellite regions, the inventors developed an error correction approach with specificities >99% (n=163) and sensitivities of 75% (n=12) and 60% (n=10), respectively, for MSI and TMB-High. For patients treated with PD-1 blockade, the data demonstrate that MSI and TMB-High in pre-treatment plasma predicted progression-free survival (hazard ratios 0.2 and 0.12, p=0.01 and 0.004, respectively). The data shows the results when plasma during therapy was analyzed in order to develop a prognostic signature for patients who achieved durable response to PD-1 blockade. These analyses demonstrate the feasibility of non-invasive pan-cancer screening and monitoring of patients who exhibit MSI or TMB-High and have a high likelihood of responding to immune checkpoint blockade.

The disclosure provides for the detection of MSI by liquid biopsy. While plasma is the illustrative example provided herein, it is understood that a liquid biopsy can be performed with a biological sample including blood, plasma, saliva, urine, feces, tears, mucosal secretions and other biological fluids.

In particular, methods of the disclosure provide and include the analytical validation of an integrated NGS-based liquid biopsy approach for the detection of microsatellite instability associated with cancers such as pancreatic, colon, gastric, endometrial, cholangiocarcinoma, breast, lung, head and neck, kidney, bladder, or prostate cancer, as well as hematopoietic cancers, among others. Failure of the DNA mismatch repair (MMR) pathway during DNA replication in cancer leads to the increased accumulation of somatic mutations. One important marker of MMR deficiency is microsatellite instability (MSI), which presents as polymorphism of tandem nucleotide repeat lengths ubiquitously distributed throughout the genome. Methods of the disclosure are offered to assay for and detect those markers via liquid biopsy. Additionally, since the presence of MMR-deficiency or MSI may serve as a marker for immunotherapy response with checkpoint inhibition, methods may be used to determine a course of treatment such as immunotherapy or the administration of a checkpoint inhibitor.

Microsatellite instability (MSI) and mismatch repair (MMR) deficiency have recently been demonstrated to predict immune checkpoint blockade response. The checkpoint inhibitor pembrolizumab is now indicated for the treatment of adult and pediatric patients with any unresectable or metastatic solid tumors identified as having either of these biomarkers. This indication covers patients with solid tumors that have progressed following prior treatment and have no satisfactory alternative treatment options.

Cancer is characterized by the accumulation of somatic mutations that have the potential to result in the expression of neoantigens, which may elicit T-cell-dependent immune responses against tumors. MMR is a mechanism by which post-replicative mismatches in daughter DNA strands are repaired and replaced with the correct DNA sequence. MMR deficiency results in both MSI and high tumor mutation burden (TMB-High), which increases the likelihood that acquired somatic mutations may be transcribed and translated into proteins that are recognized as immunogenic neoantigens. Historically, testing for MSI has been restricted to screening for Hereditary Non-Polyposis Colorectal Cancer (HNPCC), which is often characterized by early age onset colorectal cancer and endometrial cancer, as well as other extracolonic tumors. HNPCC, commonly referred to as Lynch Syndrome, is caused by mutations in the DNA mismatch repair genes (MLH1, MSH2, MSH6 and PMS2), as well as the more recently described, EPCAM (16). In addition to familial conditions, MSI can occur sporadically in cancer, and both hereditary and sporadic MSI patients respond to immune checkpoint blockade (1,2). A recent study, conducted across 39 tumor types and 11,139 patients to determine the landscape of MSI prevalence, concluded that 3.8% of these cancers across 27 tumor types displayed MSI, including 31.4% of uterine/endometrial carcinoma, 19.7% of colon adenocarcinoma, and 19.1% of stomach adenocarcinoma.

MSI can be detected through alterations in the length of microsatellite sequences typically due to deletions of repeating units of DNA to create novel allele lengths in tumor-derived DNA when compared to a matched-normal or a reference population. Current methods for MSI testing, using tissue biopsies and resection specimens, include PCR-based amplification followed by capillary electrophoresis, and more recently, next-generation sequencing (NGS) based approaches, which are used to quantify microsatellite allele lengths. The challenge associated with application of the former approach are polymerase induced errors (stutter bands), particularly in samples with low tumor purity, such as cell-free DNA (cfDNA), which can mask true biological alleles exhibiting MSI. In the case of NGS based approaches, sensitivity is typically limited by the accuracy for determination of homopolymer lengths. A novel method was recently described for determination of MSI using pre-PCR elimination of wild-type DNA homopolymers in liquid biopsies. However, given the low prevalence of MSI across cancer, it would be preferable to develop an NGS profiling approach which can include other clinically actionable alterations in cancer, including TMB, sequence mutations, copy number alterations, and translocations.

In addition to the technical challenges associated with MSI detection, it is often not possible to readily obtain biopsy or resection tissue for genetic testing due to insufficient material (biopsy size and tumor cellularity), exhaustion of the limited material available after prior therapeutic stratification, logistical considerations for tumor and normal sample acquisition after initial diagnosis, or safety concerns related to additional tissue biopsy interventions (26). In contrast, plasma-based approaches offer the unique opportunity to obtain a rapid and real-time view of the primary tumor and metastatic lesions along with associated response to therapy. Circulating tumor DNA can be used to monitor and assess residual disease in response to clinical intervention, such as surgery or chemotherapy (27-33), which can directly impact patient care. To determine the clinical impact of identifying tumors that harbor MSI or TMB-High using cfDNA, we developed and applied a 98 kb 58-gene targeted panel to cancer patients with advanced disease treated with PD-1 blockade. FIG. 1 diagrams a method 101 of detecting microsatellite instability (MSI). The method 101 includes obtaining 107 cell-free DNA (cfDNA) from a sample of plasma from a patient. Preferably, non-unique barcode are attached 111. Portions of the cfDNA are sequenced 115 to obtain sequences of a plurality of tracts of nucleotide repeats in the cfDNA. The method 101 includes modeling 121 a distribution of lengths of tracts of nucleotide repeats. A report is provided 125 describing an MSI status in the patient when a distribution of lengths of the plurality of tracts has peaks that deviate significantly from peaks in a reference distribution. Obtaining the cfDNA may include capturing target portions of DNA with probes, fragmenting the target portions to yield fragments, and attaching barcodes to the fragments.

Briefly, cell-free DNA may be extracted from cell line or blood or plasma specimens and prepared into a genomic library suitable for next-generation sequencing with oligonucleotide barcodes through end-repair, A-tailing and adapter ligation. An in-solution hybrid capture, utilizing for example, 120 base-pair (bp) RNA oligonucleotides may be performed.

In one embodiment, at least about 10-100 ng, such as 50 ng of DNA in 100 microliters of TE is fragmented in a sonicator to a size of about 150-450 bp. To remove fragments smaller than 150 bp, DNA may be purified using Agencourt AMPure XP beads (Beckman Coulter, IN) in a ratio of 1.0 to 0.9 of PCR product to beads twice and, e.g., washed using 70% ethanol per the manufacturer's instructions. Purified, fragmented DNA is mixed with H2O, End Repair Reaction Buffer, End Repair Enzyme Mix (cat #E6050, NEB, Ipswich, Mass.). The mixture is incubated then purified using Agencourt AMPure XP beads (Beckman Coulter, IN) in a ratio of 1.0 to 1.25 of PCR product to beads and washed using 70% ethanol per the manufacturer's instructions. To A-tail, end-repaired DNA is mixed with Tailing Reaction Buffer and Klenow (exo-) (cat #E6053, NEB, Ipswich, Mass.). The mixture is incubated at 37 degree C. for 30 min and purified using Agencourt AMPure XP beads (Beckman Coulter, IN) in a ratio of 1.0 to 1.0 of PCR product to beads and washed using 70% ethanol per the manufacturer's instructions. For adaptor ligation, A-tailed DNA is mixed with H2O, PE-adaptor (Illumina), Ligation buffer and Quick T4 DNA ligase (cat #E6056, NEB, Ipswich, Mass.). The ligation mixture was incubated, then amplified.

Exonic or targeted regions were captured in solution using the Agilent SureSelect v.4 kit according to the manufacturer's instructions (Agilent, Santa Clara, Calif.). The captured library was then purified with a Qiagen MinElute column purification kit. To purify PCR products, a NucleoSpin Extract II purification kit (Macherey-Nagel, PA) may be used before sequencing.

Targeted sequencing is performed. Two technical challenges to implementing these approaches in the form of a liquid biopsy include the limited amount of DNA obtained and the low mutant allele frequency associated with the MSI markers. It may be that as few as several thousand genomic equivalents are obtained per milliliter of plasma, and the mutant allele frequency can range from <0.01% to >50% total cfDNA. see Bettegowda, 2014, Detection of circulating tumor DNA in early- and late-stage human malignancies, Sci Trans Med 6(224):224ra24, incorporated by reference. The disclosed techniques overcome such problems and improve test sensitivity, optimized methods for conversion of cell-free DNA into a genomic library, and digital sequencing approaches to improve the specificity of next-generation sequencing approaches.

Methods may include extracting and isolating cell-free DNA from a blood or plasma sample and assigning an exogenous barcode to each fragment to generate a DNA library. The exogenous barcodes are from a limited pool of non-unique barcodes, for example 8 different barcodes. The barcoded fragments are differentiated based on the combination of their exogenous barcode and the information about the reads that results from sequencing such as the sequence of the reads (effectively, an endogenous barcode) or position information (e.g., stop and/or start position) of the read mapped to a reference. The DNA library is redundantly sequenced 115 and the sequences with matching barcodes are reconciled. The reconciled sequences may be aligned to a human genome reference.

The invention recognizes that completely unique barcode sequences are unnecessary. Instead, a combination of pre-defined set of non-unique sequences together with the endogenous barcodes can provide the same level of sensitivity and specificity that unique barcodes could for biologically relevant DNA amounts and can, in-fact, correct for sequencing artifacts or polymerase slippage. A limited pool of barcodes is more robust than a conventional unique set and easier to create and use. Methods include obtaining a sample comprising nucleic acid fragments, providing a plurality of sets of non-unique barcodes, and tagging 111 the nucleic acid fragments with the barcodes to generate a genomic library, wherein each nucleic acid fragment is tagged with the same barcode as another different nucleic acid fragment in the genomic library.

In embodiments, the plurality of sets is limited to twenty or fewer unique barcodes. In other embodiments, the plurality of sets is limited to ten or fewer unique barcodes.

According to the present invention, a small pool of non-unique exogenous barcodes can be used to provide a robust assay that achieves levels of sensitivity that are comparable to traditional, more complex barcoding schemes, while vastly reducing cost and complication.

After processing steps such as those described above, nucleic acids can be sequenced. Sequencing may be by any method known in the art. DNA sequencing techniques include classic dideoxy sequencing reactions (Sanger method) using labeled terminators or primers and gel separation in slab or capillary, and next generation sequencing methods such as sequencing by synthesis using reversibly terminated labeled nucleotides, pyrosequencing, 454 sequencing, Illumina/Solexa sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Separated molecules may be sequenced by sequential or single extension reactions using polymerases or ligases as well as by single or sequential differential hybridizations with libraries of probes.

A sequencing technique that can be used includes, for example, use of sequencing-by-synthesis systems sold under the trademarks GS JUNIOR, GS FLX+ and 454 SEQUENCING by 454 Life Sciences, a Roche company (Branford, Conn.), and described by Margulies, M. et al., Genome sequencing in micro-fabricated high-density picotiter reactors, Nature, 437:376-380 (2005); U.S. Pat. Nos. 5,583,024; 5,674,713; and 5,700,673, the contents of which are incorporated by reference herein in their entirety.

Other examples of DNA sequencing techniques include SOLiD technology by Applied Biosystems from Life Technologies Corporation (Carlsbad, Calif.) and ion semiconductor sequencing using, for example, a system sold under the trademark ION TORRENT by Ion Torrent by Life Technologies (South San Francisco, Calif.). Ion semiconductor sequencing is described, for example, in Rothberg, et al., An integrated semiconductor device enabling non-optical genome sequencing, Nature 475:348-352 (2011); U.S. Pub. 2010/0304982; U.S. Pub. 2010/0301398; U.S. Pub. 2010/0300895; U.S. Pub. 2010/0300559; and U.S. Pub. 2009/0026082, the contents of each of which are incorporated by reference in their entirety.

Another example of a sequencing technology that can be used is Illumina sequencing. Illumina sequencing is based on the amplification of DNA on a solid surface using fold-back PCR and anchored primers. Adapters are added to the 5' and 3' ends of DNA that is either naturally or experimentally fragmented. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated. Sequencing according to this technology is described in U.S. Pat. Nos. 7,960,120; 7,835,871; 7,232,656; 7,598,035; 6,911,345; 6,833,246; 6,828,100; 6,306,597; 6,210,891; U.S. Pub. 2011/0009278; U.S. Pub. 2007/0114362; U.S. Pub. 2006/0292611; and U.S. Pub. 2006/0024681, each of which are incorporated by reference in their entirety.

Preferably sequencing is done redundantly for deep coverage, preferably at least 30× coverage or 100×. DNA libraries may be sequenced using paired-end 111umina HiSeq 2500 sequencing chemistry to an average target total coverage of either >20,000-fold or >5,000-fold coverage for each targeted base. Sequence data may be mapped to the reference human genome. Preferably, the sequencing is next-generation, short-read sequencing. The obtained sequences may include a plurality of sequence reads and the method may include aligning the sequence reads to a reference, and identifying groups of sequence reads that originated from a unique segment of the cfDNA by means of the barcode information and position or content of the sequence reads. Primary processing of sequence data may be performed using Illumina CASAVA software (v1.8), including masking of adapter sequences. Sequence reads may bealigned against the human reference genome (version hg18) using ELAND with additional realignment of select regions using the Needleman-Wunsch method.

In some embodiments, the barcodes are non-unique barcodes that include duplicates such that different ones of the fragments are attached to identical barcodes. The high clinical efficacy of MSI status now requires a fast, objective, highly sensitive screening method, particularly in late-stage patients where tumor material may not be readily obtained. However, to extend this approach to a liquid biopsy panel requires technological advances to both overcome the inherent challenges associated with low circulating tumor DNA (ctDNA) levels which is compounded by polymerase slippage in mononucleotide repeat regions during PCR amplification as well as other sequencing artifacts.

To overcome these limitations, we applied error correction approach using molecular barcoding together with high sequencing depth and a novel peak finding algorithm to more accurately identify the specific mononucleotide sequences in cell-free DNA (cfDNA) analyses of a 64 gene panel, by way of illustration. The MSI markers can be sequenced in conjunction with such 64 gene panel, or in isolation (e.g. just sequence the markers) or in conjunction with any other gene panel (e.g., >300 genes) or with whole genome or whole exome sequencing.

The method may include amplifying the fragments to produce amplicons that include barcode information and copies of the fragments, wherein the sequencing step comprises sequencing the amplicons.

The use of the non-unique barcodes to identify groups of sequence reads that originated from a unique segment of the cfDNA allows for the lengths of the plurality of tracts to be determined correctly by correcting for errors introduced by sequencing artifacts or polymerase slippage during the amplifying step. By eliminating a significant majority of sequencing errors and polymerase slippage artifacts, we were able to reduce background error rates by >90%. Combined with implementation of a distribution modeling and a peak finding algorithm, we were able to accurately sequence the mononucleotide tracts to minimize false discovery rates for cfDNA analyses.

Figure 2:
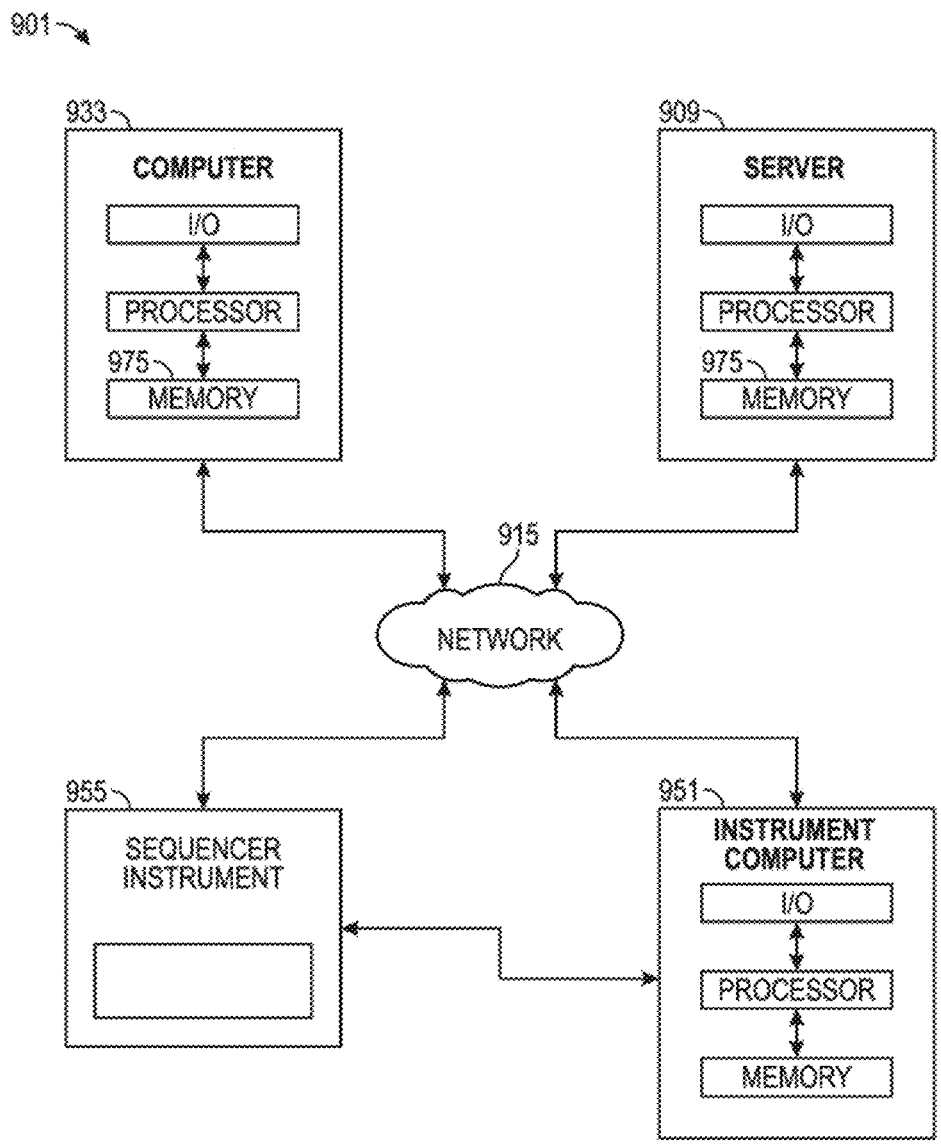
FIG. 2 shows a system for performing methods of the invention.

FIG. 2 shows a system 901 for performing methods of the disclosure. The system 901 includes a computer 933, and may optionally include a server computer 909. In certain embodiments, the system 901 includes a sequencing instrument 955 (such as an Illumina HiSeq device) which may itself include an instrument computer 951 (e.g., onboard in the sequencing instrument). Any of the computers may communicate via network 915. Each computer preferably includes at least one tangible, non-transitory memory device 975 and any input/output devices coupled to a processor. The memory may include instructions executable by the processor(s) to perform methods such as a method of detecting microsatellite instability (MSI) that includes obtaining a sample comprising fragments of cell-free DNA from a patient; attaching barcodes to the fragments, wherein at least some of the barcodes are not unique; sequencing the barcodes to obtain sequences of a plurality of markers in the DNA; determining a distribution of lengths of the plurality of markers; and providing a report describing MSI in the patient when peaks in the distribution deviate significantly from expected peaks in a modeled healthy distribution.

Figure 3:
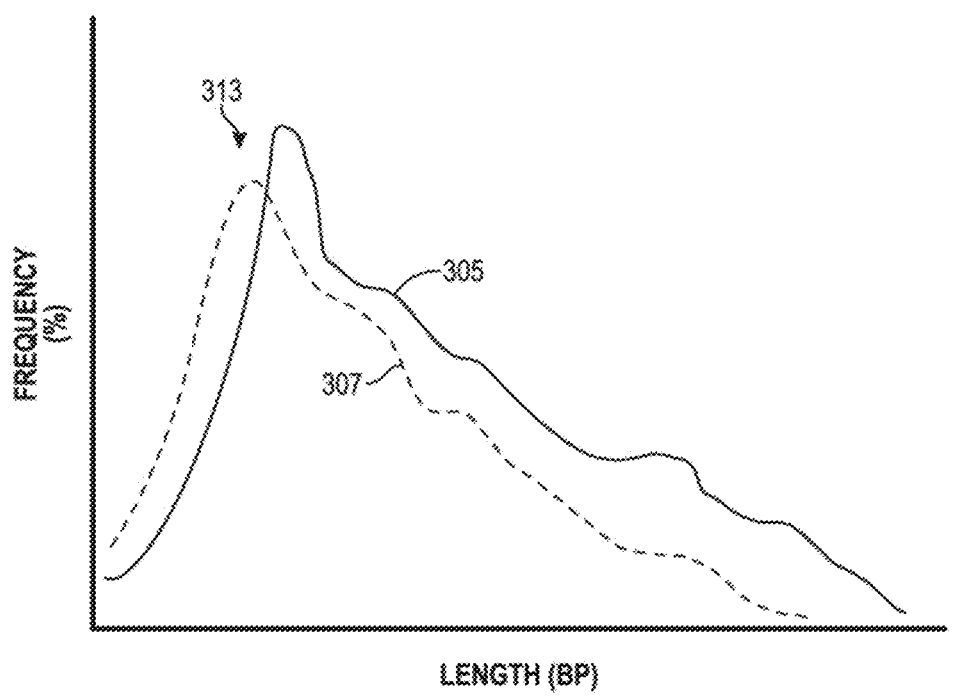
FIG. 3 shows a model of length distribution of mononucleotide repeats.

FIG. 3 illustrates distribution modeling for peak finding. In the illustrated distribution model 301, a model 307 of a distribution of lengths of tracts of nucleotide repeats is determined. It may be compared to a reference distribution 305 and an operation may be performed to find a peak 313 for the patient data 307 and/or the reference distribution 305 (which may be from patient healthy sample DNA or from a human genome reference or any other suitable source. In some embodiments, when the peak finding operation determines that the patient peak 313 is sufficiently deviant from a location of a reference peak, the method and system report the patient as MSI (microsatellite instable) for the relevant marker. Most preferably, the peak finding and distribution modeling is performed for each MSI marker. A benefit of the described method is that the distribution modeling and peak finding may be reliably implemented and automated in a high-throughput system.

MSI may be assayed by hybrid capture and NGS to address such markers as mononucleotide repeat markers such as BAT25, BAT26, MON027, NR21, and NR24. See U.S. Pub. 2017/0267760, incorporated by reference. Knowledge of MSI status is important and valuable in the treatment of many cancers, and there are patients for whom tumor material is not readily obtained. Tumors deficient in mismatch repair are particularly susceptible to a particular form of immunotherapy because this phenotype results in ongoing accumulation of mutations at a high frequency. Methods may include recommending or administering treatment for cancer patients that display the microsatellite instability phenotype or other high mutational burden. The treatment involves an inhibitory antibody for an immune checkpoint. Such checkpoints include PD-1, IDO, CTLA-4, PD-L1, and LAG-3 by way of example. Other immune checkpoints can be used as well. Antibodies can be administered by any means that is convenient, including but not limited to intravenous infusion, oral administration, subcutaneous administration, sublingual administration, ocular administration, nasal administration, and the like.

Preferably, the method 101 includes providing 125 a report with MSI status.

FIG. 4 shows a report 410 that includes a status of "instable" for certain MSI markers. Preferably, the target portions are markers for MSI such as one or more of BAT25, BAT26, MON027, NR21, NR24, Penta C, and Penta D. For example, the markers may include all of BAT25, BAT26, MON027, NR21, and NR24. In certain embodiments, each of the microsatellite markers is selected from the group consisting of BAT-25, BAT-26, MONO-27, NR-21, NR-24, Penta C, and Penta D.

In some embodiments, the method includes recommending a treatment for the patient based on the MSI status. Where the MSI status indicates that the patient is microsatellite instable, the treatment may include an immune checkpoint inhibitor. In certain embodiments, the method includes administering the treatment (e.g., the immune checkpoint inhibitor) to the patient. The immune checkpoint inhibitor may be, for example, an antibody such as an anti-PD-1 antibody; an anti-IDO antibody; anti-CTLA-4 antibody; an anti-PD-L1 antibody; or an anti-LAG-3 antibody. Types of antibodies which can be used include any that are developed for the immune checkpoint inhibitors. These can be monoclonal or polyclonal. They may be single chain fragments or other fragments of full antibodies, including those made by enzymatic cleavage or recombinant DNA techniques. They may be of any isotype, including but not limited to IgG, IgM, IgE. The antibodies may be of any species source, including human, goat, rabbit, mouse, cow, chimpanzee. The antibodies may be humanized or chimeric. The antibodies may be conjugated or engineered to be attached to another moiety, whether a therapeutic molecule or a tracer molecule. The therapeutic molecule may be a toxin, for example. The present invention is more particularly described in the following examples which are intended as illustrative only since numerous modifications and variations therein will be apparent to those skilled in the art. The following examples are intended to illustrate but not limit the invention.

EXAMPLES

Example 1

Methods

Patients and Sample Collection

Formalin fixed paraffin embedded (FFPE) tumor and matched normal buffy coat specimens (n=61) from individuals with cancer were obtained after surgical resection through commercial biorepositories from BioIVT (Hicksville, N.Y., USA), Indivumed (Hamburg, Germany), and iSpecimen (Lexington, Mass., USA). Plasma samples from healthy individuals (n=163) were procured through BioIVT (Hicksville, N.Y., USA) during routine screening with negative results and no prior history of cancer. Human cells from previously characterized MSI cell lines were obtained from ATCC (Manassas, Va., USA) (n=5; LS180, LS411N, SNU- C2B, RKO, and SNU-C2A). Finally, baseline and serial plasma samples from cancer patients with progressive metastatic carcinoma (n=16; 11 colorectal, 3 ampullary, and 2 small intestine) were obtained while patients were enrolled in a phase 2 clinical trial to evaluate immune checkpoint blockade with pembrolizumab (1,2). Radiographic and serum protein biomarker data for CEA and CA19-9 were collected as a part of routine clinical care. All samples were obtained under Institutional Review Board approved protocols with informed consent for research.

Orthogonal Testing of FFPE Tissue for MSI Status

The Promega MSI analysis system (Madison, Wis., USA) was used to assess MSI status in DNA derived from FFPE tumor tissue together with matched normal buffy coat by multiplex PCR and fluorescent capillary electrophoresis. Tumors were classified as MSI if two or more of the five mononucleotide markers (BAT25, BAT26, MONO27, NR21, and NR24) had significant length differences compared to the matched normal allele lengths. Additionally, 2-pentanucleotide repeat loci (PentaC and PentaD) were used to confirm case identity between normal and tumor samples.

Sample Preparation and Next-Generation Sequencing

FFPE Tumor and Normal Analyses

Sample processing from tissue or buffy coat, library preparation, hybrid capture, and sequencing were performed as previously described at Personal Genome Diagnostics (Baltimore, Md.)(34,36). Briefly, DNA was extracted from FFPE tissue and matched normal buffy coat cells using the Qiagen FFPE Tissue Kit and DNA Blood Mini Kit, respectively (Qiagen, Hilden, Germany). Genomic DNA was sheared using a Covaris sonicator (Woburn, Mass., USA) to a size range of 150-450 bp, and subsequently used to generate a genomic library using the New England Biolabs (Ipswich, Mass., USA) end-repair, A-tailing, and adapter ligation modules. Finally, genomic libraries were amplified and captured using the Agilent SureSelect XT in-solution hybrid capture system with a custom 120 bp RNA panel targeting the pre-defined regions of interest across 125 genes (Table 1). Captured libraries were sequenced on the Illumina HiSeq 2000 or 2500 (Illumina, San Diego, Calif., USA) with 100 bp paired end reads.

Plasma Analyses

Sample processing from plasma, library preparation, hybrid capture, and sequencing were performed as previously described at Personal Genome Diagnostics (Baltimore, Md.)(34). Briefly, blood was collected in EDTA tubes and centrifuged at 800 g for 10 minutes at 4° C. to separate plasma from white blood cells. Cell-free DNA was extracted from plasma using the QIAamp Circulating Nucleic Acid Kit (Qiagen, Hilden, Germany). Libraries were prepared with 5-250 ng of cfDNA using the NEBNext DNA Library Prep Kit (New England Biolabs, Ipswich, Mass., USA). After end repair and a-tailing, a pool of eight unique Illumina dual index adapters with 8 bp barcodes were ligated to cfDNA to allow for accurate error correction of duplicate reads, followed by 12 cycles of amplification. Targeted hybrid capture was performed using Agilent SureSelect XT in-solution hybrid capture system with a custom 120 bp RNA panel targeting the pre-defined regions of interest across 58 genes (Table 4) according to the manufacturer protocol (Agilent Technologies, Santa Clara, Calif., USA). Captured libraries were sequenced on the Illumina HiSeq 2000 or 2500 (Illumina, San Diego, Calif., USA) with 100 bp paired end reads.

Example 2

Microsatellite Instability Analyses by Next-Generation Sequencing

Sequence data were aligned to the human reference genome assembly (hg19) using BWA-MEM (37). Reads mapping to microsatellites were excised using Samtools (38) and analyzed for insertion and deletion events (indels). In most cases, alignment and variant calling did not generate accurate indel calls in repeated regions due to low quality bases surrounding the microsatellites. Therefore, a secondary local realignment and indel quantitation was performed. Reads were considered for an expanded indel analysis if (i) the mononucleotide repeat was contained to more than eight bases inside of the start and end of the read, (ii) the indel length was ≤12 bases from the reference length, (iii) there were no single base changes found within the repeat region, (iv) the read had a mapping score of 60, and (v) ≤20 bases of the read were soft clipped for alignment. After read specific mononucleotide length analysis, error correction was performed to allow for an aggregated and accurate quantitation among duplicated fragments using molecular barcoding. Reads were aggregated into barcode families by using the ordered and combined read 1 and read 2 alignment positions with the molecular barcode. Barcode families were considered for downstream analysis if they comprised of at least 2 reads and >50% of reads had consistent mononucleotide lengths. The error corrected mononucleotide length distribution was subjected to a peak finding algorithm where local maxima were required to be greater than the error corrected distinct fragment counts of the adjacent lengths±2 bp. Identified peaks were further filtered to only include those which had >3 error corrected distinct fragments at ≥1% of the absolute coverage. The shortest identified mononucleotide allele length was compared to the hg19 reference length. If the allele length was ≥3 bp shorter than the reference length, the given mononucleotide loci was classified as exhibiting instability. This approach was applied across all mononucleotide loci. Samples were classified as MSI-H if ≥20% of loci were MSI. In the targeted 58 gene plasma panel, BAT25, BAT26, MONO27, NR21, and NR24 mononucleotide loci were for the determination of MSI status. In the targeted 125 gene targeted tissue panel, an additional 65 microsatellite regions were used for MSI classification.

Example 3

Tumor Mutational Burden Analyses by Next-Generation Sequencing

Next generation sequencing data were processed and variants were identified using the VariantDx custom software as previously described (34). A final set of candidate somatic mutations were selected for tumor mutational burden analyses based on: (i) variants enriched due to sequencing or alignment error were removed (≤5 observations or <0.30% mutant allele fraction), (ii) nonsynonymous and synonymous variants were included, but variants arising in non-coding regions were removed, (iii) hotspot variants annotated in COSMIC (version 72) were not included to reduce bias toward driver alterations, (iv) common germline SNPs found in dbSNP (version 138) were removed as well as variants deemed private germline variants based on the variant allele frequency, and (v) variants associated with clonal hematopoietic expansion were not included in the candidate variant set (39).

In Silico TCGA Analyses

In order to evaluate the accuracy of the 98 kb targeted panel for prediction of TMB, a comparison to whole-exome sequencing data derived from The Cancer Genome Atlas (TCGA)(35) was performed by considering synonymous and nonsynonymous alterations, excluding known hotspot mutations which may not be representative of TMB in the tumor. The cutoff for consideration as TMB-High was set to 5 candidate variants (50.8 mutations/Mbp sequenced) based on in silico analyses utilizing the TCGA data to achieve >95% accuracy (>36 mutations/Mbp).

Statistical Analyses

Due to small sample size, Firth's Penalized Likelihood was used to evaluate significant differences between Kaplan-Meier curves for progression free survival and overall survival with the classifiers baseline MSI status, baseline TMB status, two consecutive timepoints with >80% reduction in baseline protein biomarker levels, two consecutive timepoints with 0% residual MSI alleles on treatment, and two consecutive timepoints with >90% reduction in baseline TMB levels. Pearson correlations were used to evaluate significant association between TMB in the 58 gene targeted panel compared to whole-exome analyses, progression free and overall survival compared to residual protein biomarker levels, and progression free and overall survival compared to residual MSI and TMB allele levels. A student t-test was used to evaluate significant differences between the mean TMB level in TMB-High and TMB-Low patients. Response rate was calculated as the number of patients exhibiting a complete or partial response as a proportion of the total patients considered, and then evaluated using a Fisher's exact test.

Example 4

Development of an Assay to Identify MSI in Cell-Free DNA

To identify MSI in tumor-derived cfDNA, a method to detect length polymorphisms in mononucleotide tract alleles in circulating tumor DNA (ctDNA), which occur at low frequency in plasma, is needed. To overcome this issue, we developed a highly sensitive error-correction approach incorporating the commonly-used mononucleotide tracts BAT25, BAT26, MONO27, NR21, and NR24 for the determination of MSI status in tissue and plasma specimens using NGS. DNA was converted into an NGS compatible library using molecular barcoding, after which these targeted microsatellite loci were enriched using in-solution hybrid capture chemistry together with the regions associated with other clinically relevant genomic alterations.

Figure 5A:
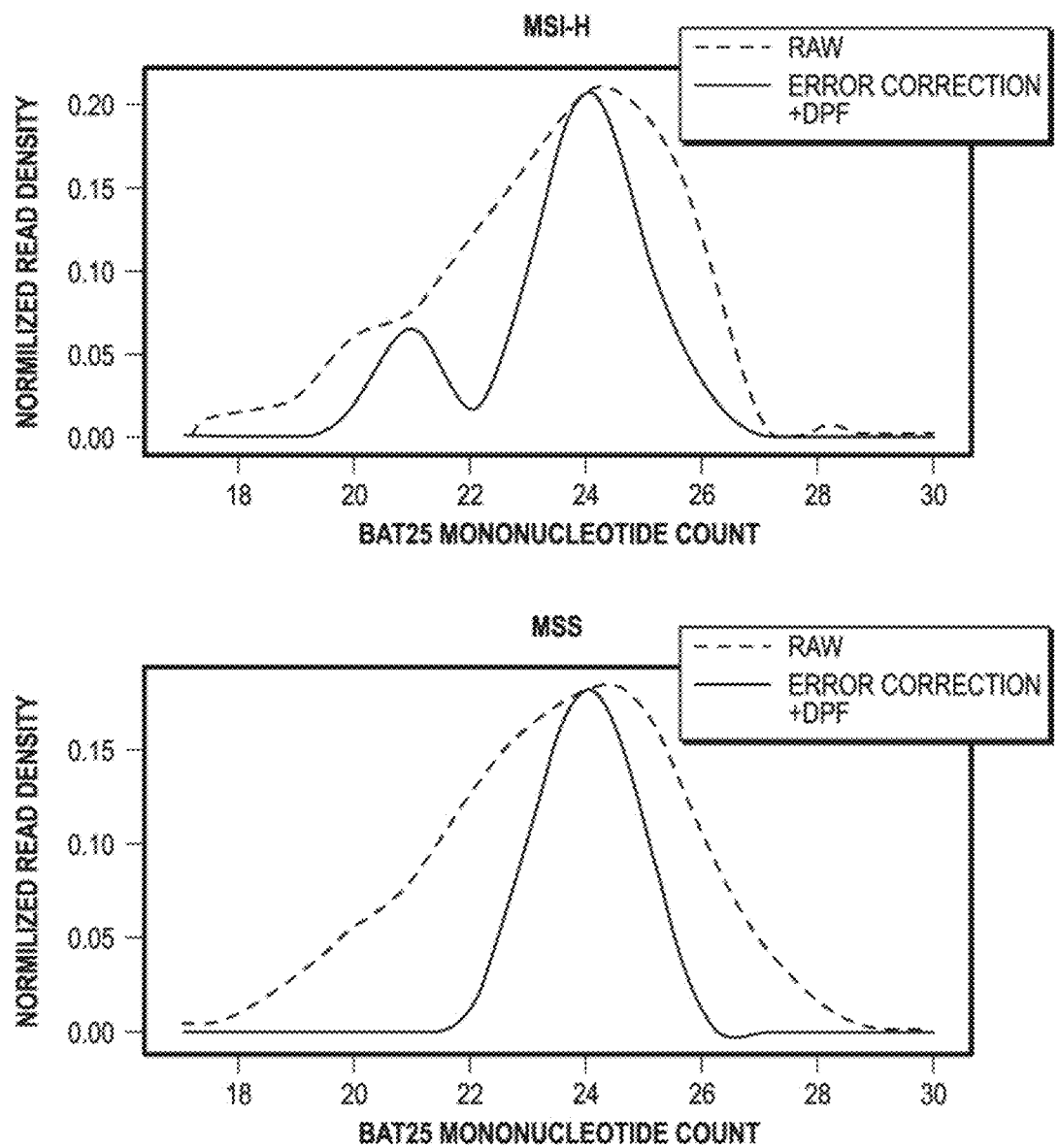
FIGS. 5A-5D Plasma-Based Detection of Microsatellite Instability. (A) Prior to error correction and Digital Peak Finding (DPF) (light pink), the mononucleotide count distribution demonstrated high background noise due to sequencing related aberrations and polymerase slippage in library preparation PCR and sequencing. These are subsequently resolved after error correction and DPF (dark pink) to create distinct distributions for MSI and MSS alleles. (B) Across the BAT25, BAT26, MON027, NR21, and NR24 mononucleotide loci in 163 healthy donor plasma specimens, the error corrected mononucleotide count distribution was assessed with a DPF algorithm to identify mononucleotide alleles and determine MSI status. Prior to error correction and DPF (light pink), the majority of healthy donor samples exhibit alleles below the MSI cutoff (hashed line). Kaplan-Meier curves for progression free survival (C) and overall survival (D) among patients with progressive metastatic carcinoma were determined using MSI status from pre-treatment plasma specimens. In MSI patients (n=9*), median progression free survival was 16.17 months, while median overall survival was not reached. In MSS patients (n=7*), median progression free survival and median overall survival were 2.81 and 7.6 months, respectively. *Three patients with a tissue enrollment status of MSI-H were classified as MSS using pre-treatment baseline cfDNA obtained from plasma.
Figure 5B:
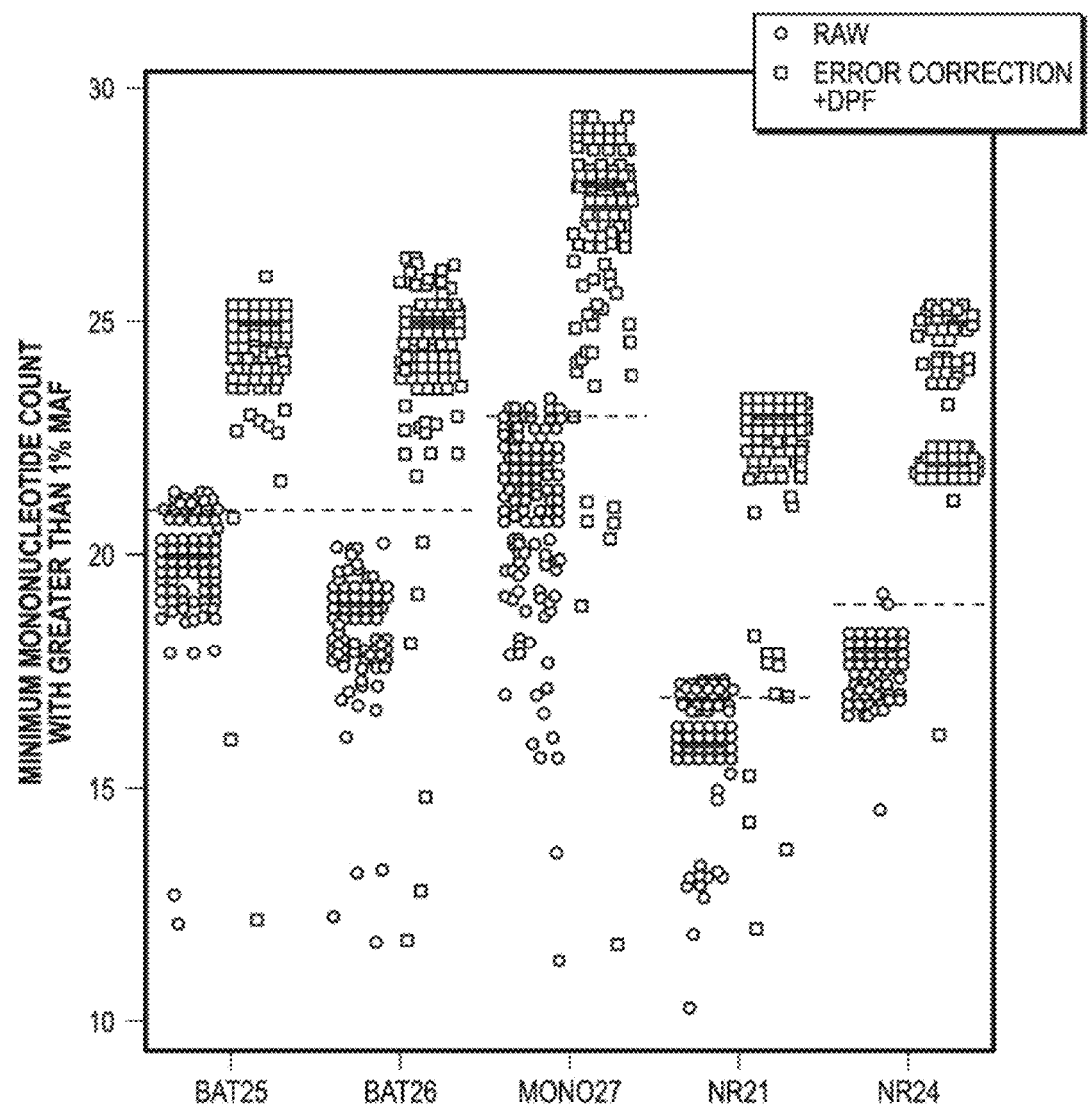

To address the technical challenges associated with detection of low level allele length polymorphisms obtained from NGS, we combined an error correction approach for accurate determination of insertions and deletions (indels) present in the cfDNA fragments, together with a digital peak finding (DPF) method for quantification of MSI and MSS alleles. Redundant sequencing of each cfDNA fragment was performed, and reads were aligned to the five microsatellite loci contained in the human reference genome (hg19). cfDNA sequences were then analyzed for indels through a secondary local alignment at these five microsatellite loci to more accurately determine the indel length. To perform the error correction, duplicated reads associated with each cfDNA molecule were consolidated, only recognizing indels present throughout barcoded DNA fragment replicates obtained through redundant sequencing. Finally, the DPF approach was applied across the error corrected distribution of indels to identify high confidence alleles which exhibit microsatellite instability (FIGS. 5A and 5B).

To demonstrate the capability of this approach, we first evaluated the performance of the method for detection of MSI in formalin fixed, paraffin embedded (FFPE) tumor tissue specimens obtained from 31 MSI-High (MSI-H) and 30 microsatellite stable (MSS) tumors previously characterized with the PCR-based Promega MSI analysis system. In addition to these five mononucleotide markers, we sequenced 125 selected cancer genes which harbor clinically actionable genetic alterations consisting of sequence mutations (single base substitutions and indels), copy number alterations, and gene rearrangements in cancer (Table 1). Analyses of these 61 colorectal tumors yielded 193 Gb of total sequence data, corresponding to 832-fold distinct coverage on average across the 979 kb panel (Table 2). Analysis of these five mononucleotide loci, together with 65 additional microsatellite regions contained within the 125 gene panel resulted in 100% sensitivity (31/31) and 100% specificity (30/30) for determination of MSI status using the patient-matched tumor and normal samples (Table 3) Similarly, analysis of tumor NGS data using the DPF approach without the patient-matched normal sample yielded 100% concordance (61/61).

Next, we evaluated the signal-to-noise ratio in homopolymer regions from next-generation sequencing data obtained using cfDNA extracted from plasma. Together with the five mononucleotide loci, we developed a 98 kb, 58 gene panel for sequence mutation (single base substitutions and indels) analyses of clinically actionable genetic alterations in cancer (Table 4). To demonstrate the specificity of this approach for direct detection of MSI, we first obtained plasma from healthy donors (n=163), all of which would be expected to be tumor-free and MSS. These analyses yielded over 1.2 Tb of total sequence data, corresponding to 2,600-fold distinct coverage on average across the 98 kb targeted panel, and resulted in a per-patient specificity of 99.4% (162/163) for determination of MSI status (FIG. 5B, Tables 5 and 6).

Because ctDNA, even in patients with advanced cancer, may be present at mutant allele fractions (MAFs) less than 5%, we characterized the ability of DPF for sensitive and reproducible detection of MSI at low MAFs. Five previously characterized MSI cell line samples obtained from ATCC (LS180, LS411N, SNU-C2B, RKO, and SNU-C2A) were sheared to a fragment profile simulating cfDNA and diluted with normal DNA to yield a total of 25 ng evaluated at 1% MAF. Additionally, three of these cell lines (LS180, LS411N, and SNU-C2B) were evaluated at 1% MAF in triplicate within, and triplicate across library preparation and sequencing runs (Table 5). Based on the MAF observed in the parental cell line, the cases detected as MSI were computationally confirmed to contain MSI allele MAFs of 0.35%-1.87%, with a median MSI allele MAF of 0.92%. In total, MSI was detected in 90% (18/20) of samples and demonstrated 93.3% (14/15) repeatability and reproducibility within and across runs (Table 6). For one case which was not detected as MSI, one MSI allele was identified at 0.33% MAF and for the other case, no MSI alleles were detected.

Example 5

Assessment of MSI in cfDNA in Patients Treated with PD-1 Blockade

To evaluate the analytical and clinical performance of this approach for determination of MSI in cfDNA from patients with late-stage cancers, we obtained baseline and serial plasma from patients with metastatic cancers (including 11 colorectal, 3 ampullary, and 2 small intestine), with or without MMR deficiency, while enrolled in a clinical trial to evaluate immune checkpoint blockade with the PD-1 blocking antibody, pembrolizumab(1,2)(Table 7). In total, 12 MSI-H cases and 4 MSS cases, determined through archival tissue-based analyses, were evaluated across at least two timepoints, including baseline, and after approximately 2 weeks, 10 weeks, 20 weeks, and >100 weeks.

Figure 9A:
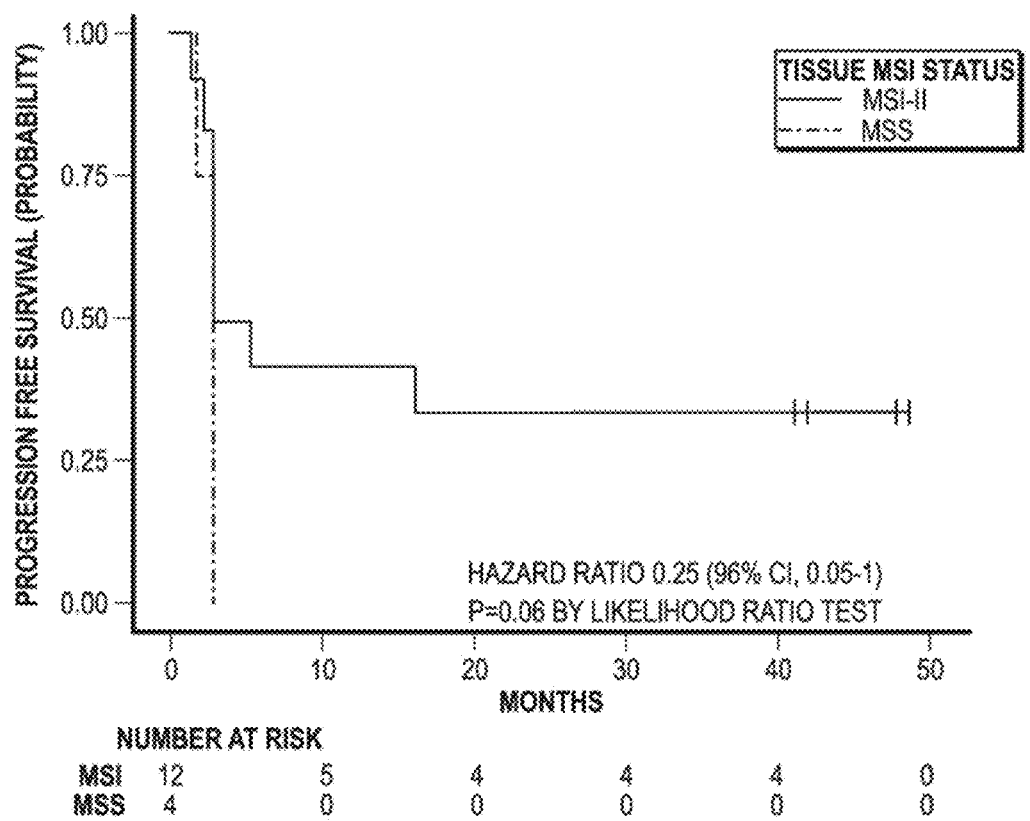
FIGS. 9A-9D Archival Tissue-Based Detection of Microsatellite Instability and High Tumor Mutation Burden. Kaplan-Meier curves for progression free survival (A) and overall survival (B) among patients with progressive metastatic carcinoma were determined using MSI status from archival tissue. In MSI patients (n=12), median progression free survival and median overall survival were 4.23 and 20.69 months, respectively. In MSS patients (n=4), median progression free survival and median overall survival were 2.81 and 6.31 months, respectively. Kaplan-Meier curves for progression free survival (C) and overall survival (D) among patients with progressive metastatic carcinoma were determined. In TMB-High patients (n=10), median progression free survival was 10.81 months, while median overall survival was not reached. In TMB-Low patients (n=3), median progression free survival and median overall survival were 2.81 and 5.02 months, respectively.
Figure 9B:
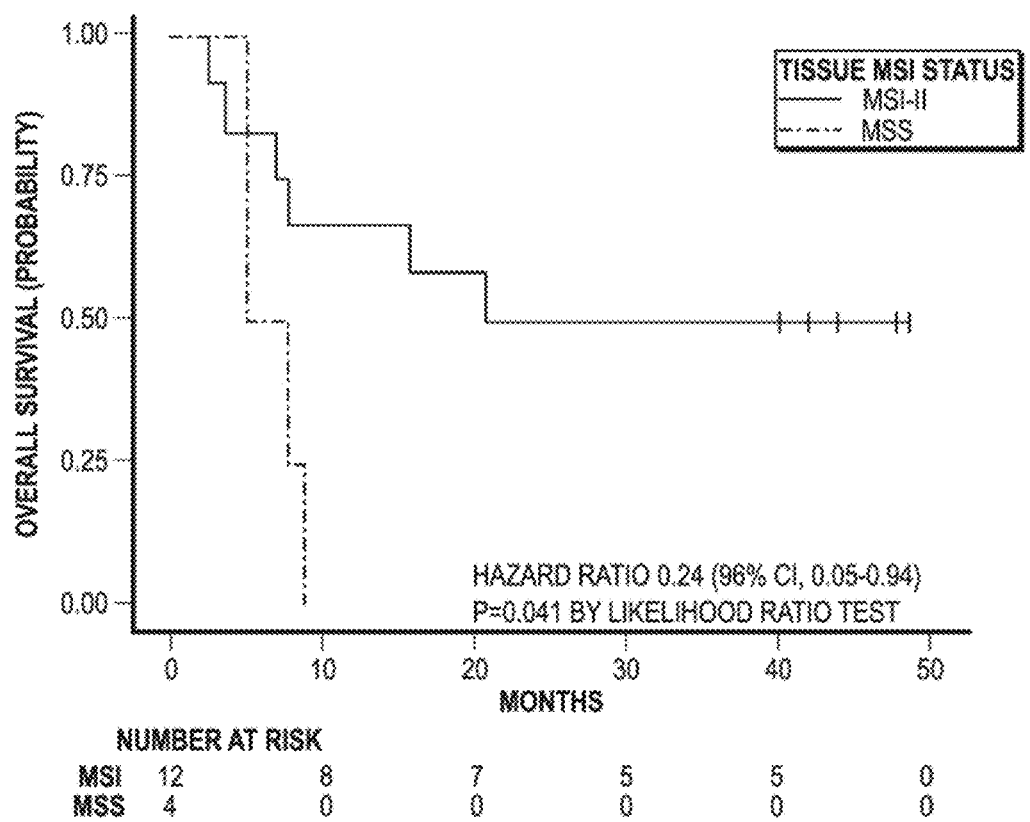

Patients with MSI tumors as determined by archival tissue analyses had improved progression-free survival (hazard ratio, 0.25; p=0.05, likelihood ratio test) and overall survival (hazard ratio, 0.24; p=0.041, likelihood ratio test) (FIGS. 9A and 9B and Table 8). In cfDNA, we could detect MSI in 75% (9/12) of the previously characterized MSI-H patients, and correctly identified 100% (4/4) of the MSS patients (Table 6). Of the three cases that were MSI in the tumor tissue and MSS in the cfDNA, one was a colorectal tumor (patient exhibited progressive disease) and two were small intestinal tumors (one patient exhibited a partial response and one exhibited progressive disease) with relatively low levels of ctDNA with MAF of 0.4%, 1.1%, and no detectable ctDNA in the third case (34) (Table 7).

Figure 5C:
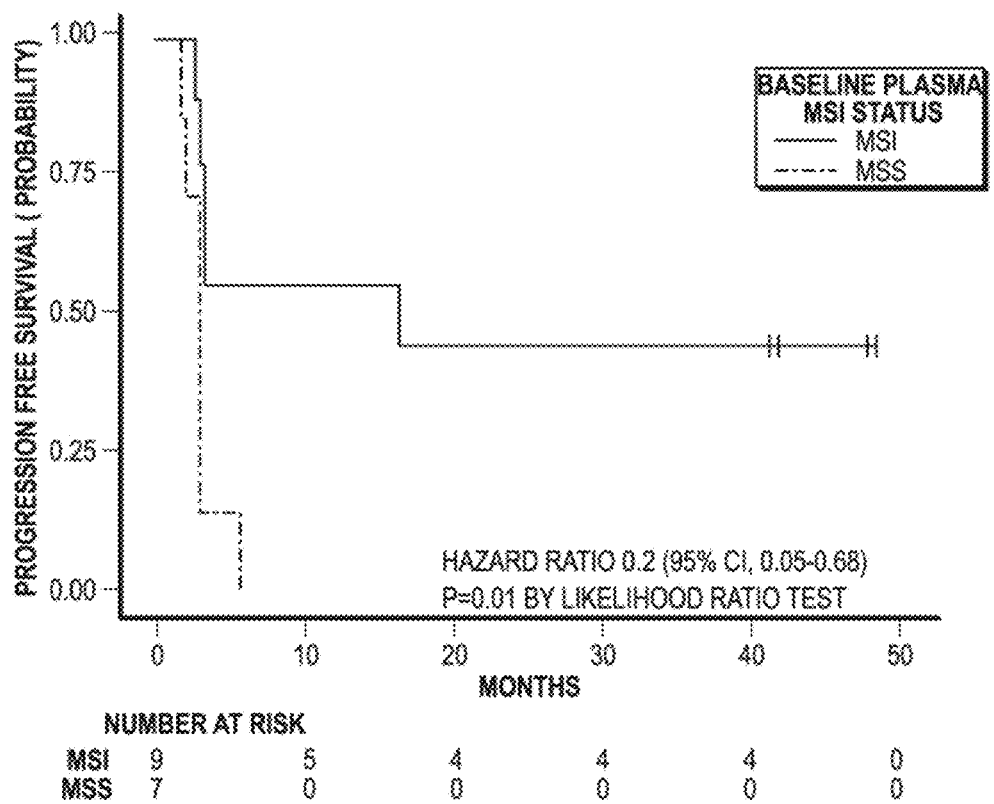
Figure 5D:
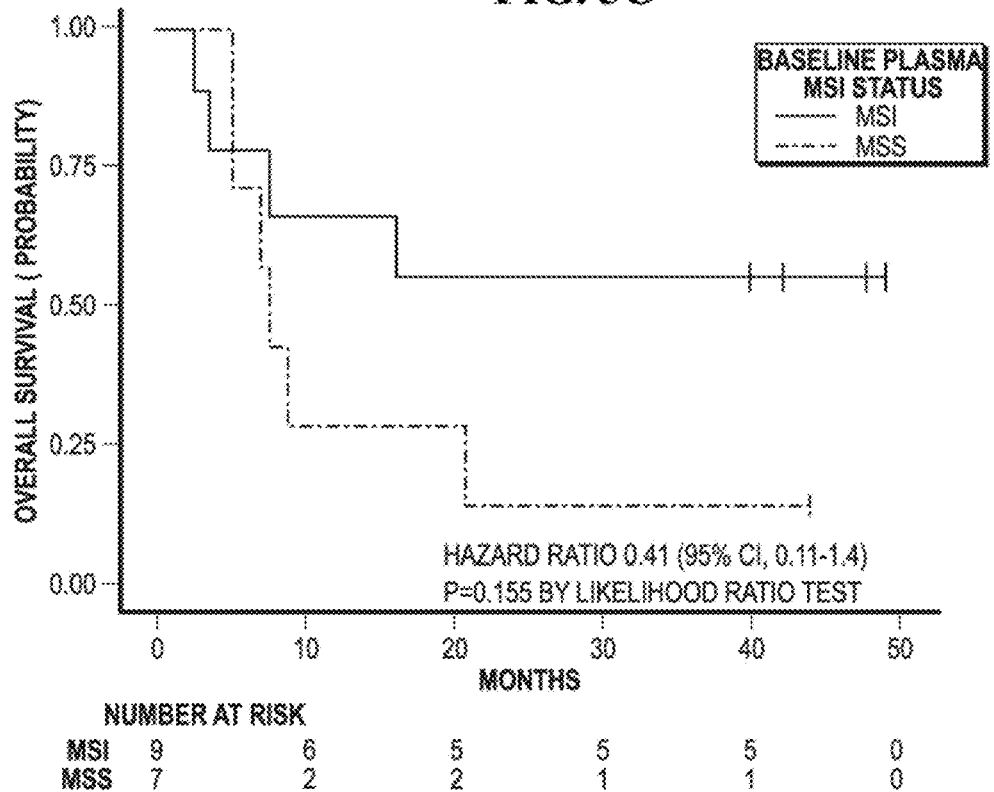

We then evaluated pre-treatment MSI status in ctDNA to predict response and clinical outcome to treatment with PD-1 blockade. We assessed radiographic response, progression-free and overall survival to predict clinical outcome. When compared to progression free survival, direct detection of MSI in baseline cfDNA could be used to predict response to immune checkpoint blockade (hazard ratio, 0.2; p=0.01, likelihood ratio test) (FIGS. 5C and 5D).

Estimating Tumor Mutation Burden in ctDNA

Figure 6A:
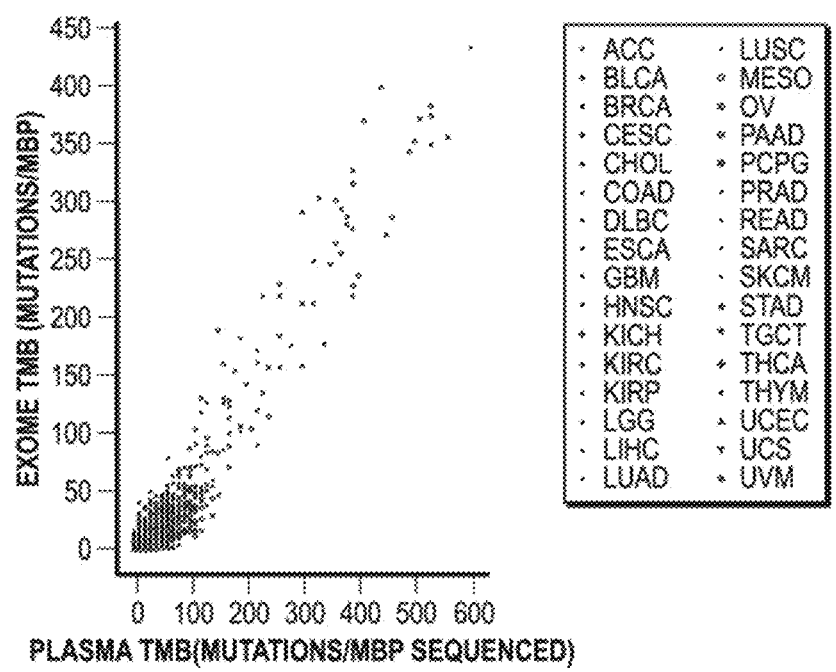
FIGS. 6A-6E Plasma-Based Detection of High Tumor Mutation Burden. (A) Using whole exome sequencing data derived from The Cancer Genome Atlas (TCGA), a significant positive correlation between the tumor mutation burden (TMB) evaluated in the 98 kb targeted regions compared to the whole exome analyses was observed (r=0.91, p<0.0001; Pearson correlation). (B) Comparison of the accuracy for determination of the TMB derived from the targeted panel in plasma compared to whole-exome analyses of matched archival tissue samples in 13 patients yielded a significant positive correlation (r=0.693, p=0.007; Pearson correlation). (C) The overall TMB status at baseline was assigned as TMB-High or TMB-Low using a cutoff of 50.8 mutations/Mbp sequenced. In total, six patients were categorized as TMB-High and ten patients as TMB-Low, with a median load of 132 mutations/Mbp sequenced and 15.2 mutations/Mbp sequenced, respectively. Additionally, 163 healthy donor cases were evaluated, all of which were determined to be TMB-Low, with a median load of 0 mutations/Mbp sequenced across the panel. Kaplan-Meier curves for progression free survival (D) and overall survival (E) among this same cohort of patients were determined using TMB status from pre-treatment plasma specimens with a cutoff of 50.8 mutations/Mbp sequenced. In TMB-High patients (n=6), median progression free survival and median overall survival were not reached. In TMB-Low patients (n=10), median progression free survival and median overall survival were 2.84 and 7.62 months, respectively.

In addition to MSI status, we also evaluated the ability of our cfDNA panel to predict TMB across a range of tumor types, using whole exome sequencing data derived from The Cancer Genome Atlas (TCGA)(35). We considered synonymous and nonsynonymous alterations identified by TCGA and excluded known hotspot mutations which may not be representative of TMB in the tumor. These analyses demonstrated a positive correlation between predicted TMB from our targeted 58 gene plasma panel compared to the TCGA whole exome analyses (r=0.91, p<0.0001; Pearson correlation) (FIG. 6A). We determined that a cutoff of five mutations (50.8 mutations/Mbp sequenced) in the targeted plasma panel could be used to identify tumors with exceptionally high TMB related to MMR deficiency (>36 mutations/Mbp) at >95% accuracy.

Figure 6B:
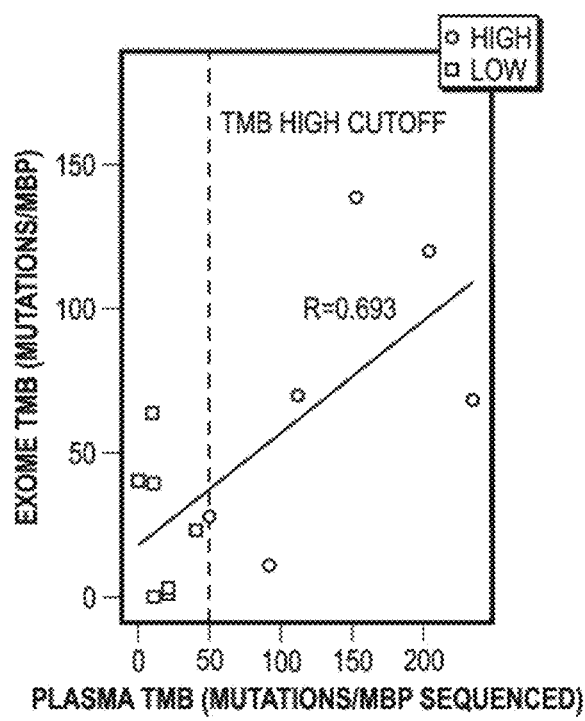
Figure 6C:
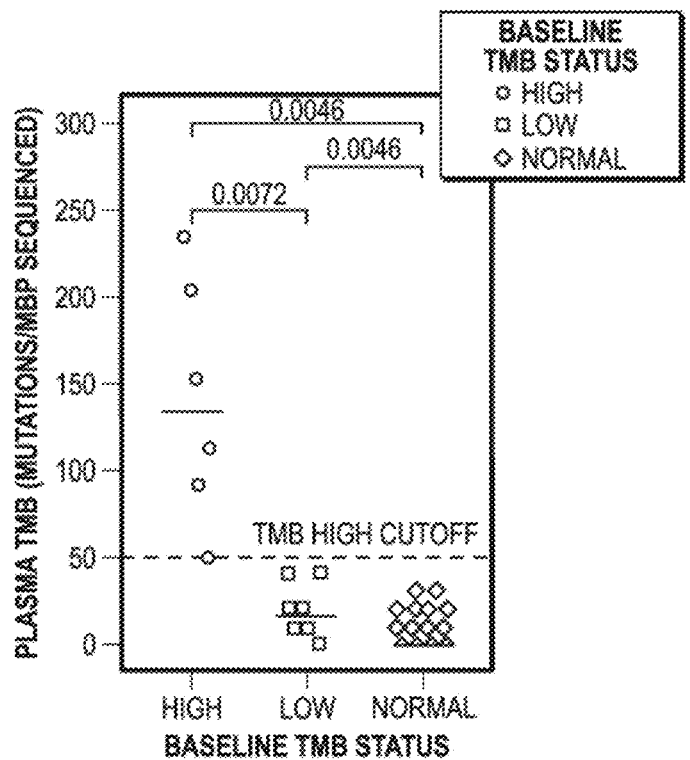
Figure 6D:
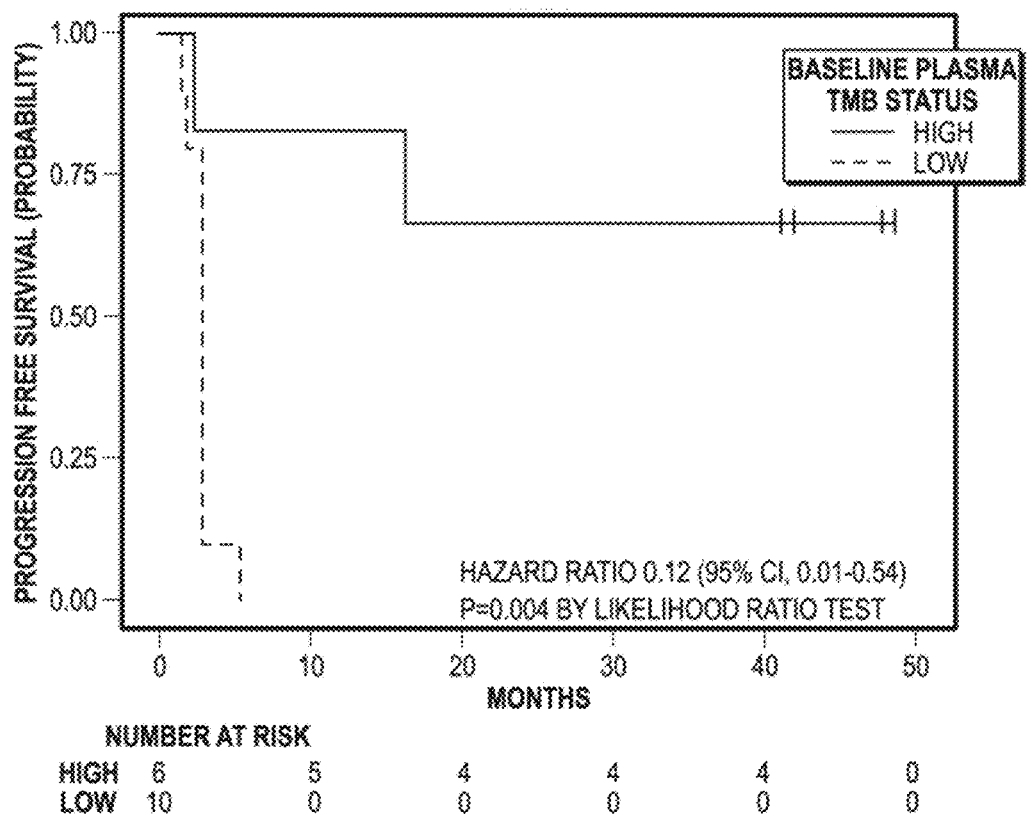
Figure 6E:
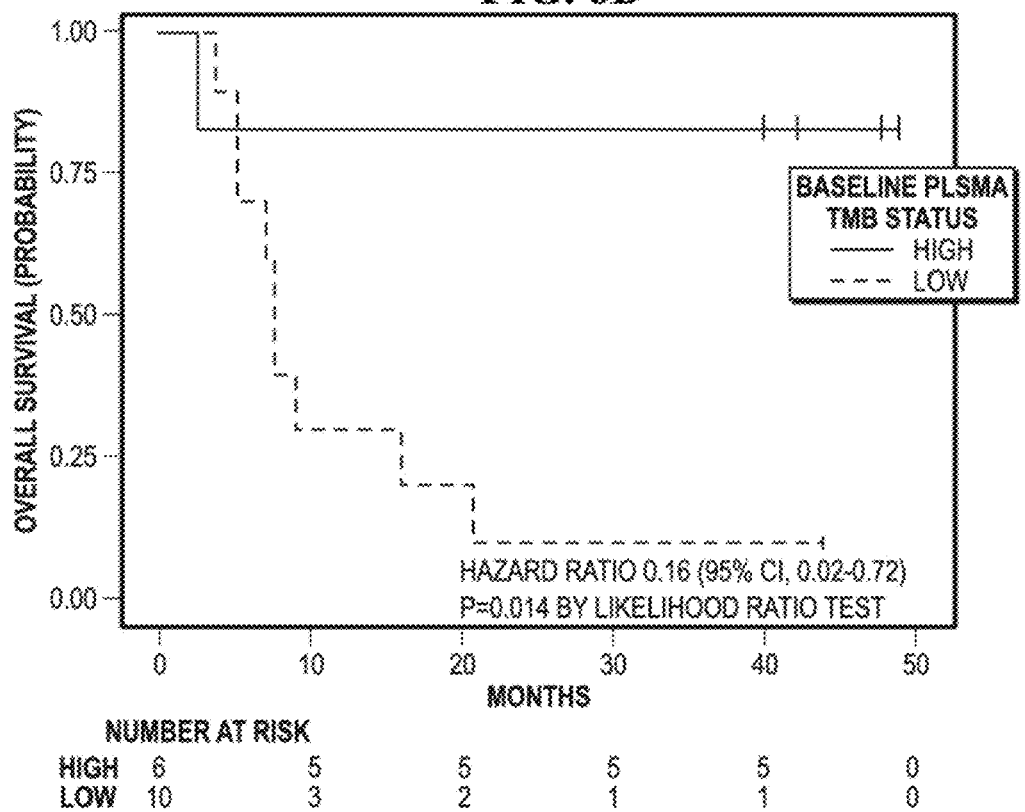
Figure 9C:
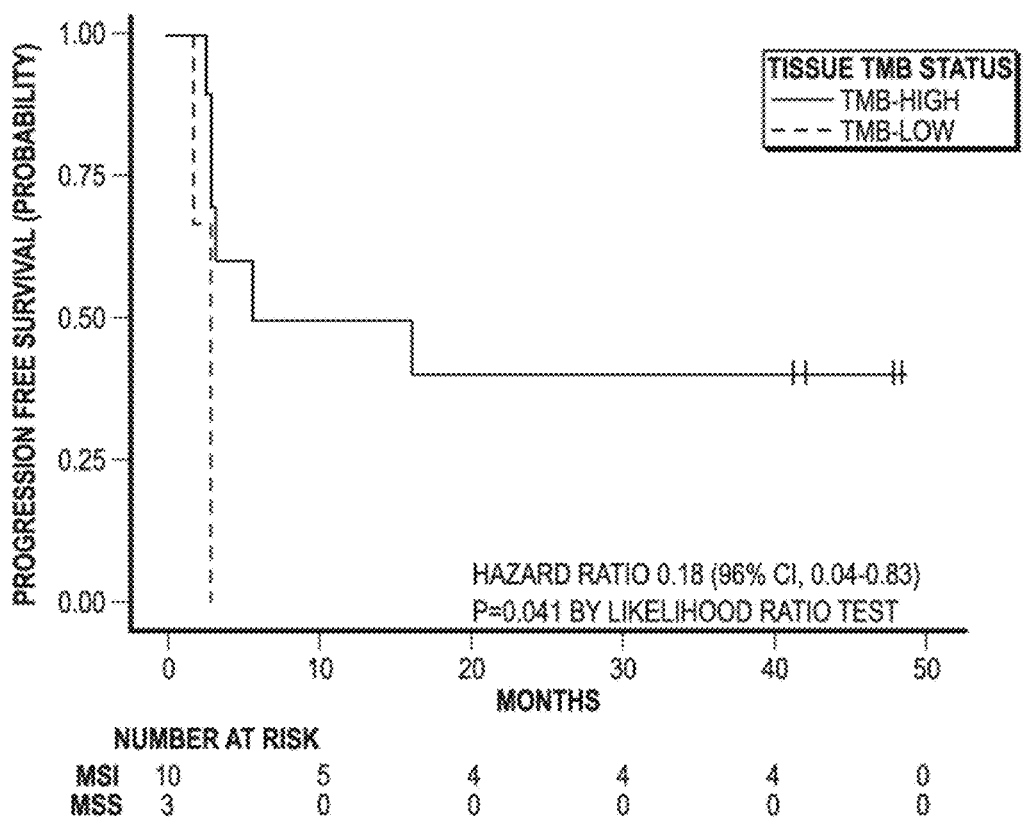
Figure 9D:
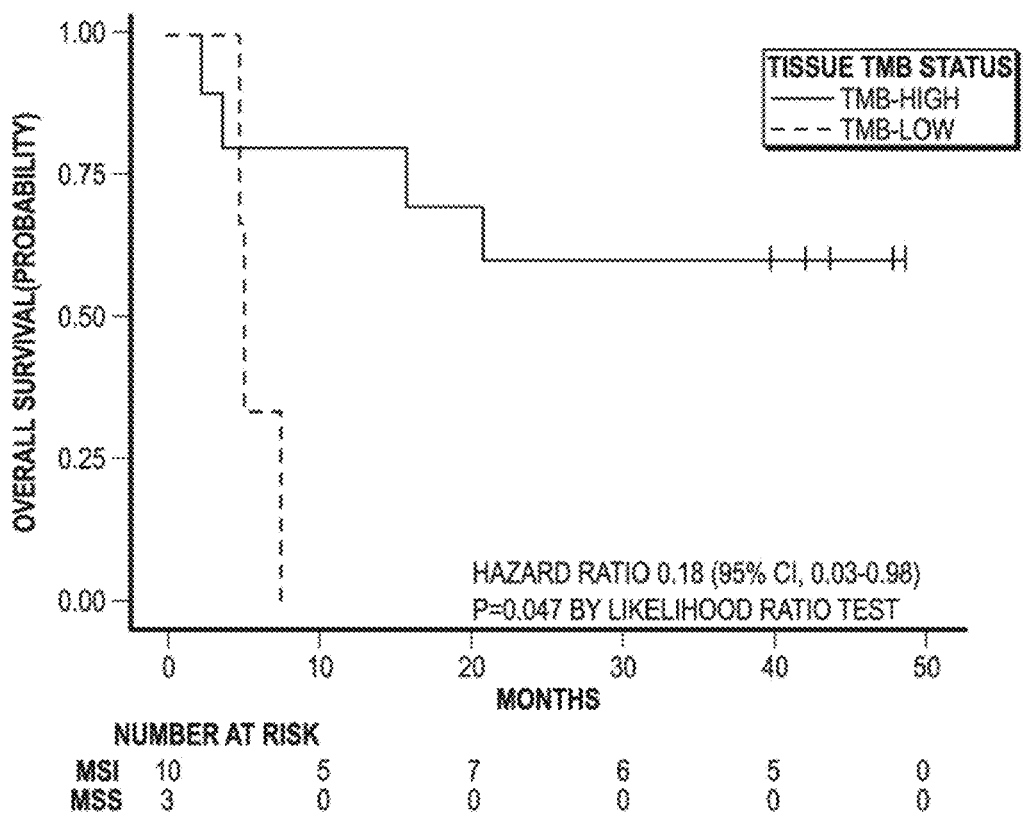

Patients with TMB-High tumors as determined by archival tissue analyses (≥10 mutations/Mbp) had improved progression-free survival (hazard ratio, 0.19; p=0.041, likelihood ratio test) and overall survival (hazard ratio, 0.18; p=0.047, likelihood ratio test) (FIGS. 9C and 9D). We also evaluated the accuracy of TMB derived from the targeted panel in 13 baseline plasma cases, compared to whole-exome analyses of tumor and matched normal tissue in the same patients (1,2), and a similar correlation was identified (r=0.69, p=0.007; Pearson correlation) (FIG. 6B). These patients were classified as either TMB-High or TMB-Low using a cutoff of 50.8 mutations/Mbp sequenced, which captured six of the ten tumors categorized as TMB-High by archival tissue and provided a statistically significant difference in the TMB classification (p=0.0072, t-test) (FIG. 6C). This algorithm was applied to the same 163 healthy donor plasma samples and 100% (163/163) were determined to be TMB-Low (FIG. 6C). When considering TMB classification as a predictor of clinical outcome from the same phase 2 study cohort, TMB-High status was associated with favorable progression free survival (hazard ratio, 0.12; p=0.004 likelihood ratio test) and overall survival (hazard ratio, 0.16; p=0.014, likelihood ratio test) (FIGS. 6D and 6E). Interestingly, all four MSI-H enrolled patients exhibiting a complete response were classified as TMB-High, and all five enrolled MSI-H patients with progressive disease were classified as TMB-Low (Table 7).

Example 6

Figure 7A:
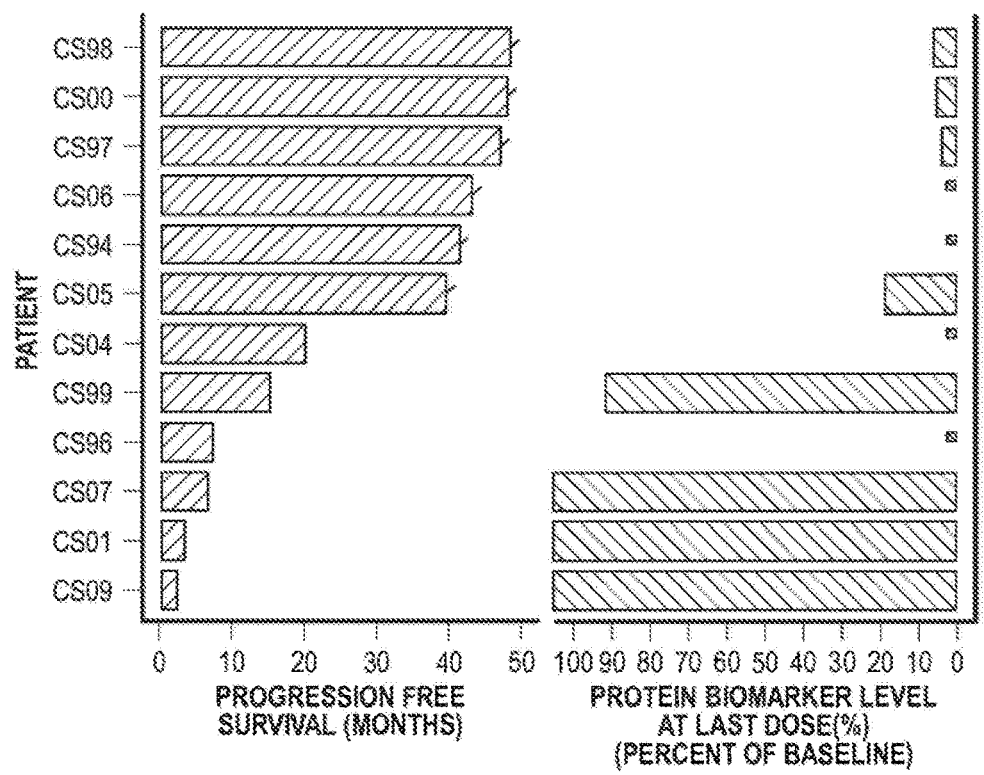
FIGS. 7A-7F Serial Plasma-Based Overall Survival Analysis for Patients Treated with Immune Checkpoint Blockade. (A) Evaluation of overall survival with the protein biomarker level at last dose (CEA or CA19-9). A significant inverse correlation was observed between the overall survival in months when compared to the residual protein biomarker (r=−0.99, p=<0.001; Pearson correlation). (B) Kaplan-Meier curves for overall survival among patients with tissue enrollment status of MSI and detectable protein biomarker levels (n=8). For patients with >80% reduction in protein biomarker levels (n=4), median overall survival was not reached. For patients with ≤80% reduction in protein biomarker levels (n=4), median overall survival was 5.26 months. (C) Evaluation of overall survival compared to residual MSI allele levels at last dose. A significant inverse correlation was observed between the overall survival when compared to the residual MSI allele levels (r=−0.70, p=0.034; Pearson correlation). (D) Kaplan-Meier curves for overall survival among patients with tissue enrollment status of MSI and detectable MSI status at baseline (n=9). For patients with two consecutive timepoints displaying no residual MSI alleles (n=4) median overall survival was not reached. For patients with multiple timepoints containing residual MSI alleles (n=5) median overall survival was 7.64 months. (E) Evaluation of overall survival compared to residual TMB levels at last dose. A significant inverse correlation was observed between the overall survival in months when compared to the residual TMB levels (r=−0.95, p=<0.001; Pearson correlation). (F) Kaplan-Meier curves for overall survival among patients with tissue enrollment status of MSI and detectable TMB levels at baseline (n=11). For patients with >90% reduction in TMB levels (n=4), median overall survival was not reached. For patients with ≤90% reduction in TMB levels (n=7), median overall survival was 7.64 months. "/" indicates a censored datapoint; "*" indicates cases where baseline protein biomarker, MSI or TMB was not detected and were not included in the subsequent analyses; In cases where residual protein biomarker, MSI or TMB levels increased when compared to baseline, values of greater than 100% are indicated.
Figure 7B:
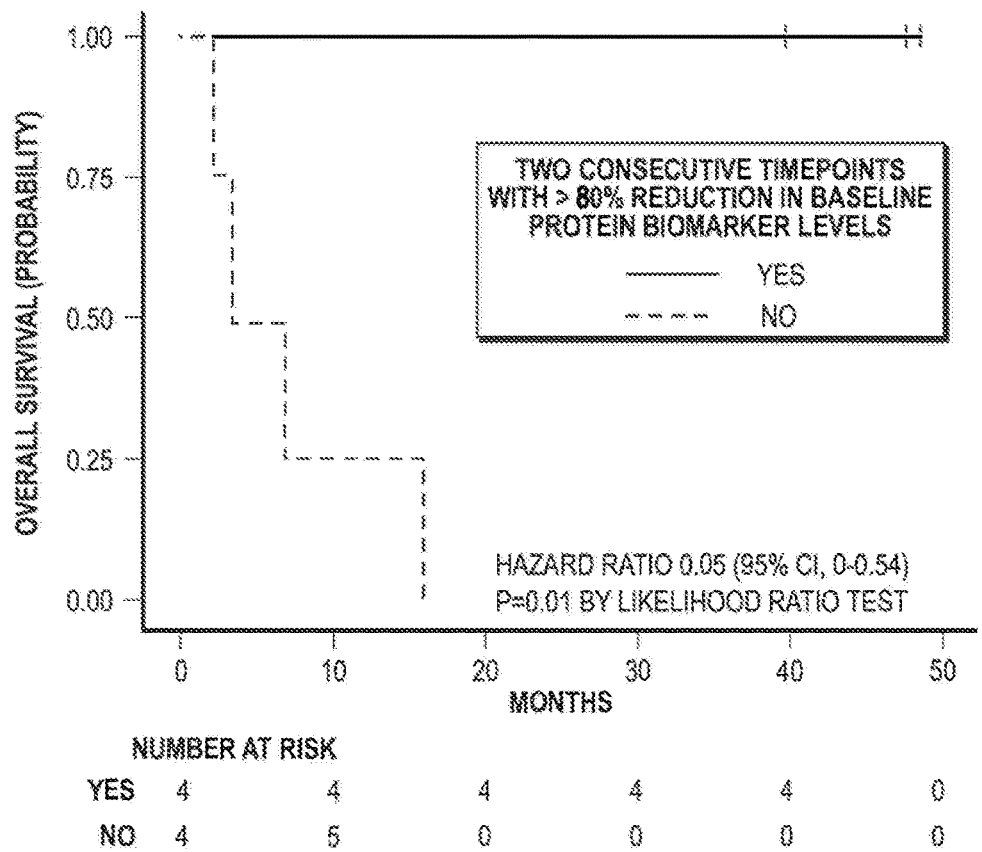
Figure 7C:
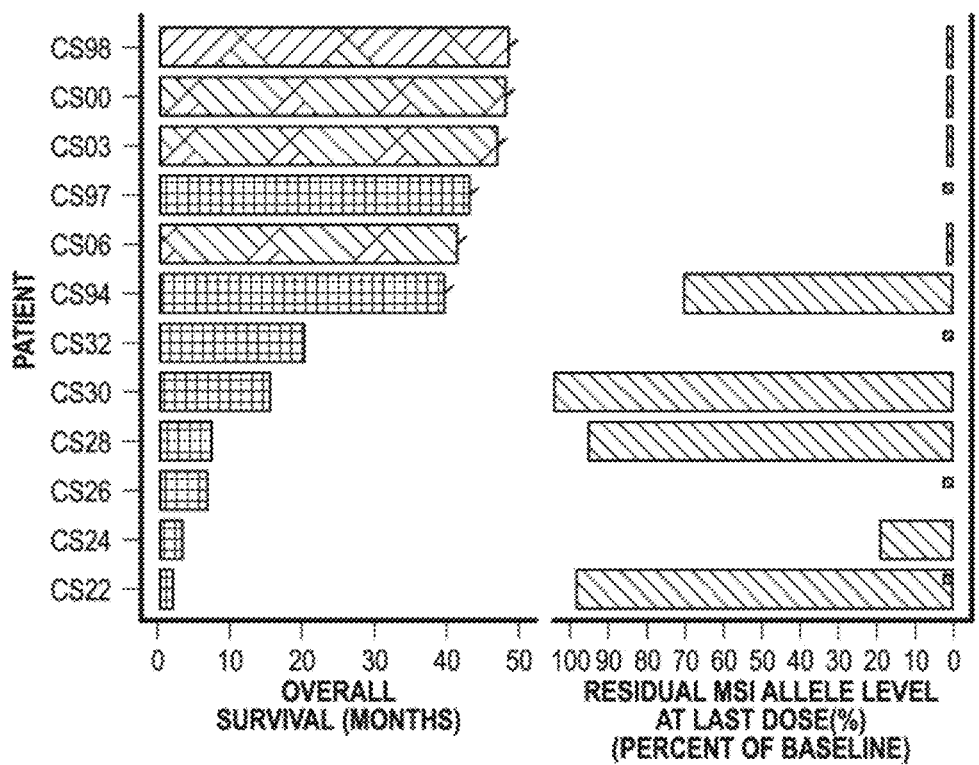
Figure 7D:
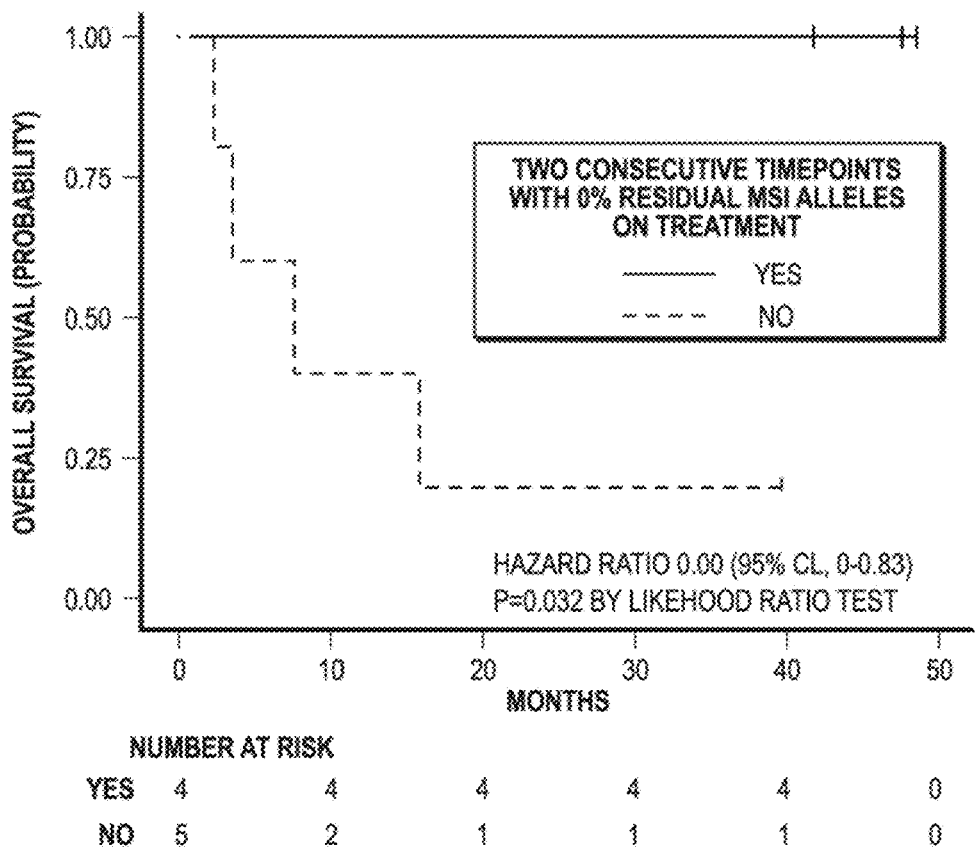
Figure 7E:
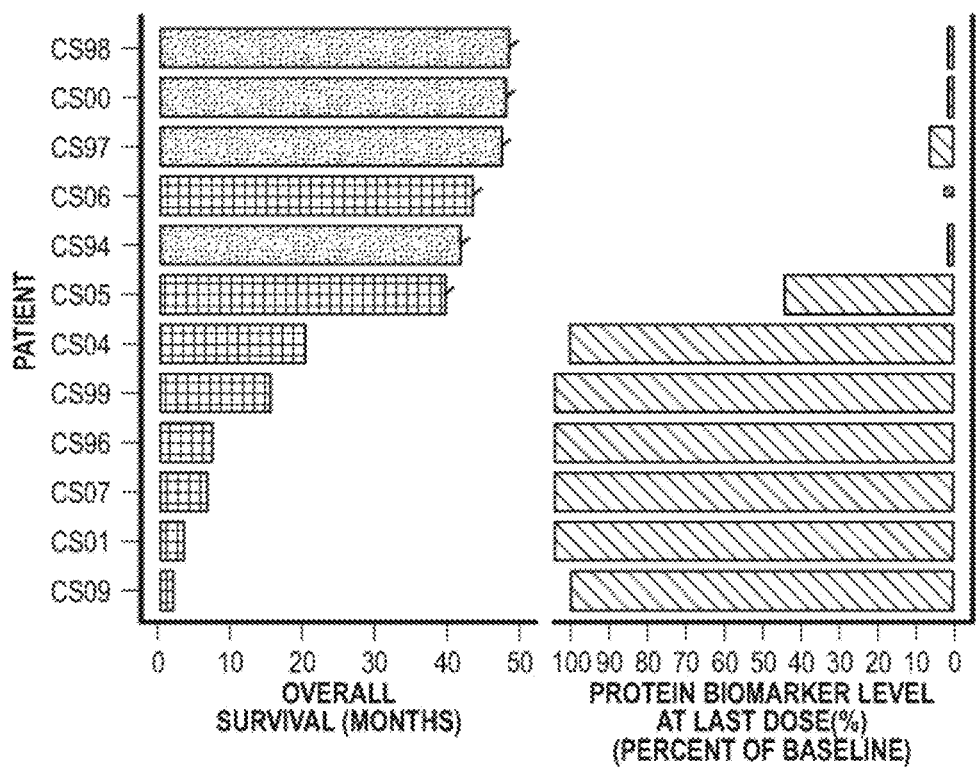
Figure 7F:
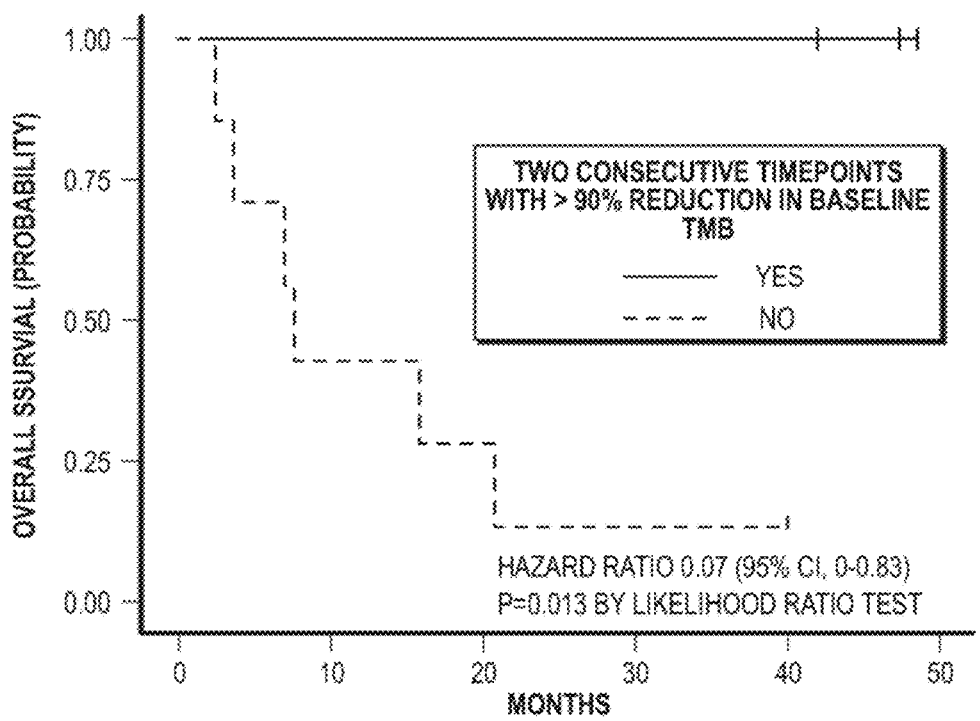
Figure 8A:
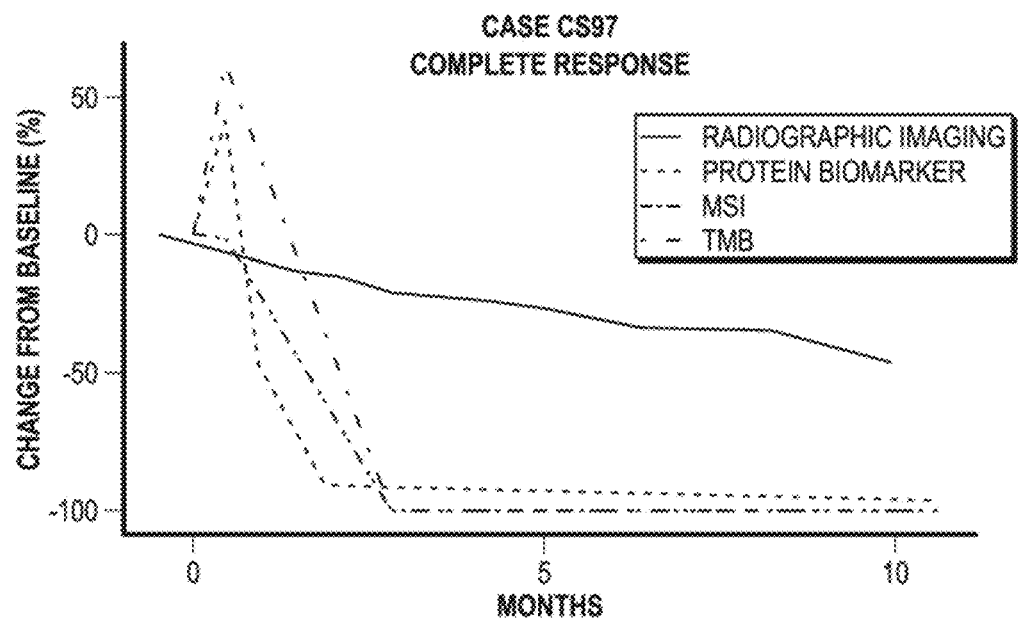
FIGS. 8A-8D Monitoring of Patients During Immune Checkpoint Blockade. For three patients with a complete response to immune checkpoint blockade (CS97 (A), CS98 (B), and CS00 (C) and one patient with progressive disease (CS05 (D)), circulating protein biomarkers (CEA, ng/mL and CA19-9, units/mL), residual alleles exhibiting MSI, and TMB levels were evaluated over time during treatment. In each case exhibiting a complete response, residual MSI and TMB alleles were reduced to 0% mutant allele fraction (MAF) between 0.6 and 4.8 months after first dose.
Figure 8B:
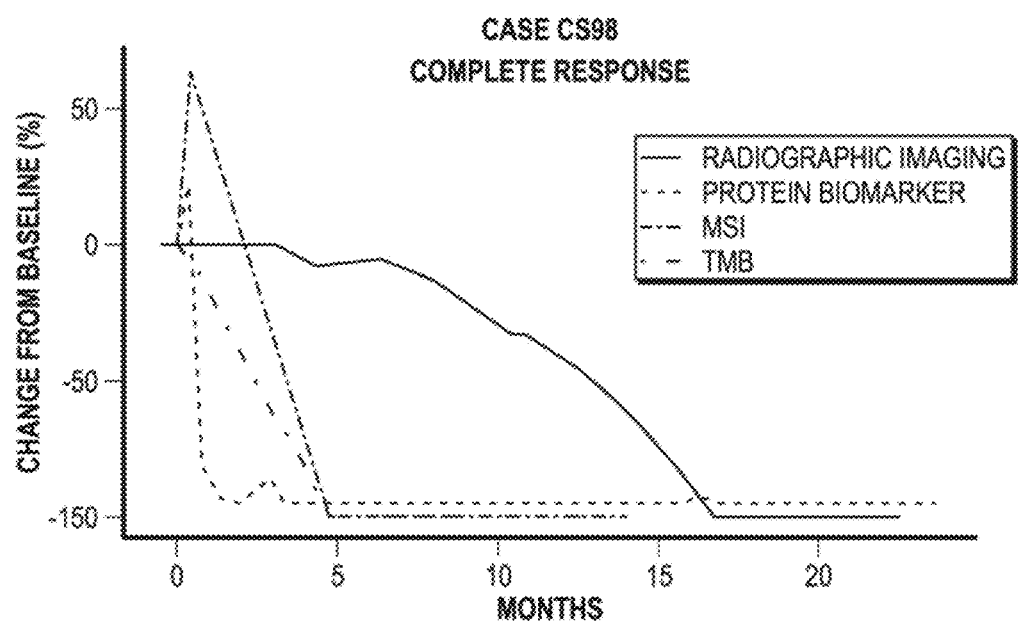
Figure 8C:
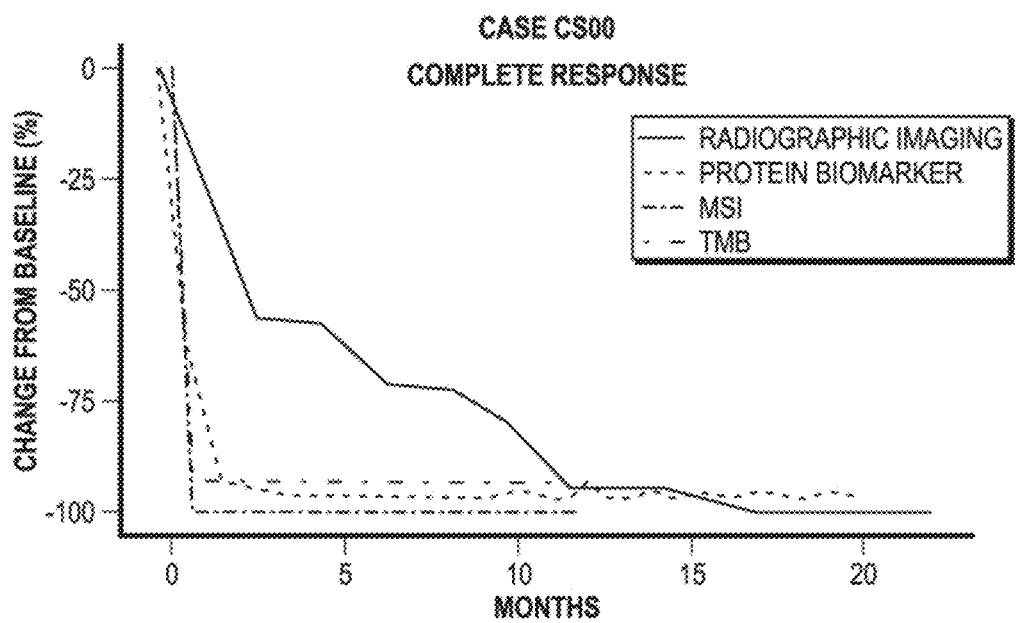
Figure 8D:
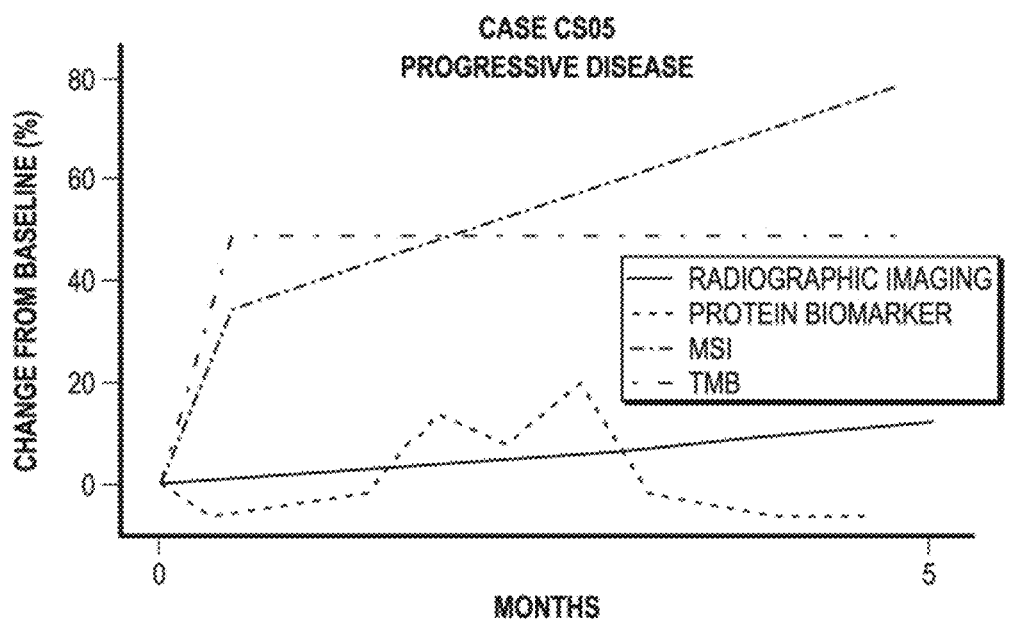
Figure 10A:
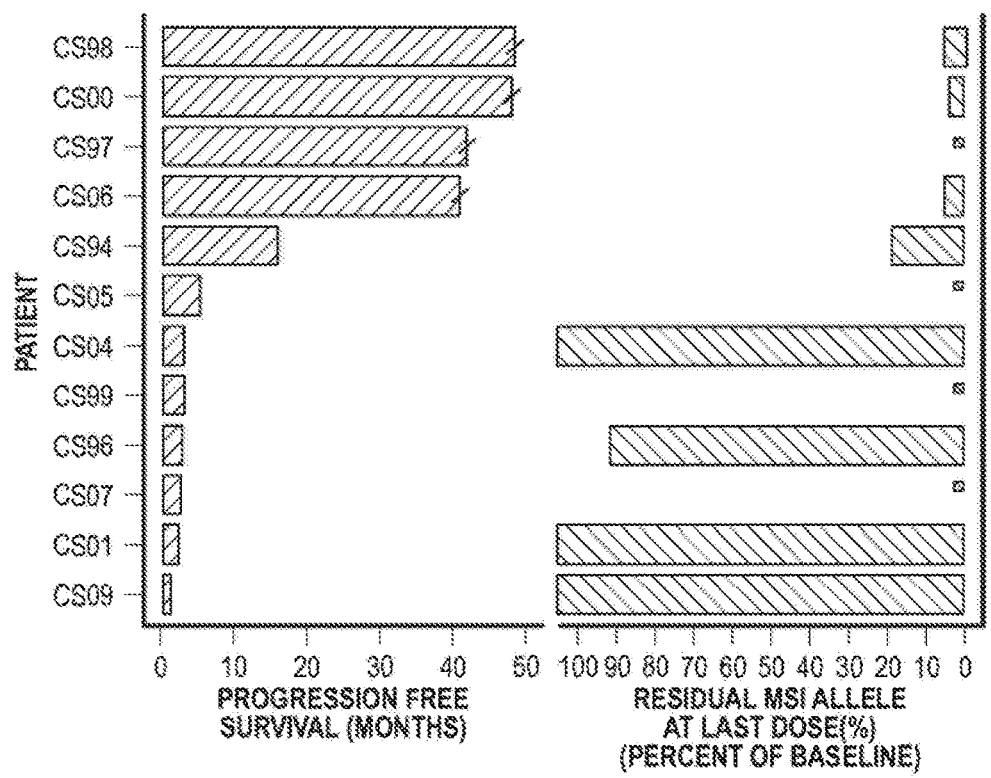
FIGS. 10A-10F Plasma-Based Progression Free Survival Analysis for Patients Treated with Immune Checkpoint Blockade. (A) Evaluation of progression free survival with the protein biomarker level at last dose (CEA or CA19-9). An inverse correlation was observed between the progression free survival in months when compared to the residual protein biomarker (r=−0.92, p=0.001; Pearson correlation). (B) Kaplan-Meier curves for progression free survival among patients with tissue enrollment status of MSI and detectable protein biomarker levels (n=8). For patients with >80% reduction in protein biomarker levels (n=4), median progression free survival was not reached. For patients with ≤80% reduction in protein biomarker levels (n=4), median progression free survival was 2.63 months. (C) Evaluation of progression free survival compared to residual MSI allele levels at last dose. A significant inverse correlation was observed between the progression free survival in months when compared to the residual MSI allele levels (r=−0.84, p=0.004; Pearson correlation). (D) Kaplan-Meier curves for progression free survival among patients with tissue enrollment status of MSI and detectable MSI status at baseline (n=9). For patients with two consecutive timepoints displaying no residual MSI alleles (n=4) median progression free survival was not reached. For patients with multiple timepoints containing residual MSI alleles (n=5) median progression free survival was 3.01 months. (E) Evaluation of progression free survival compared to residual TMB levels at last dose. A significant inverse correlation was observed between the progression free survival in months when compared to the residual TMB levels (r=−0.98, p=<0.001; Pearson correlation). (F) Kaplan-Meier curves for progression free survival among patients with tissue enrollment status of MSI and detectable TMB levels at baseline (n=11). For patients with >90% reduction in TMB levels (n=4), median progression free survival was not reached. For patients with ≤90% reduction in TMB levels (n=7), median progression free survival was 2.88 months. "/" indicates a censored datapoint; "*" indicates cases where baseline protein biomarker, MSI or TMB was not detected and were not included in the subsequent analyses; In cases where residual protein biomarker, MSI or TMB levels increased when compared to baseline, values of greater than 100% are indicated.
Figure 10B:
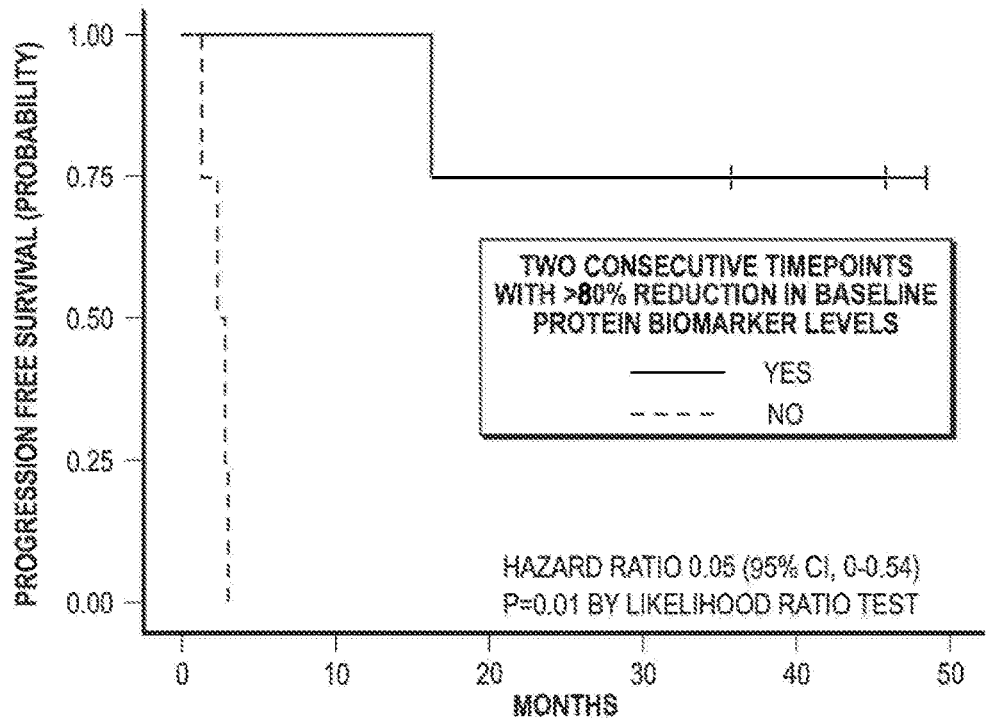
Figure 10C:
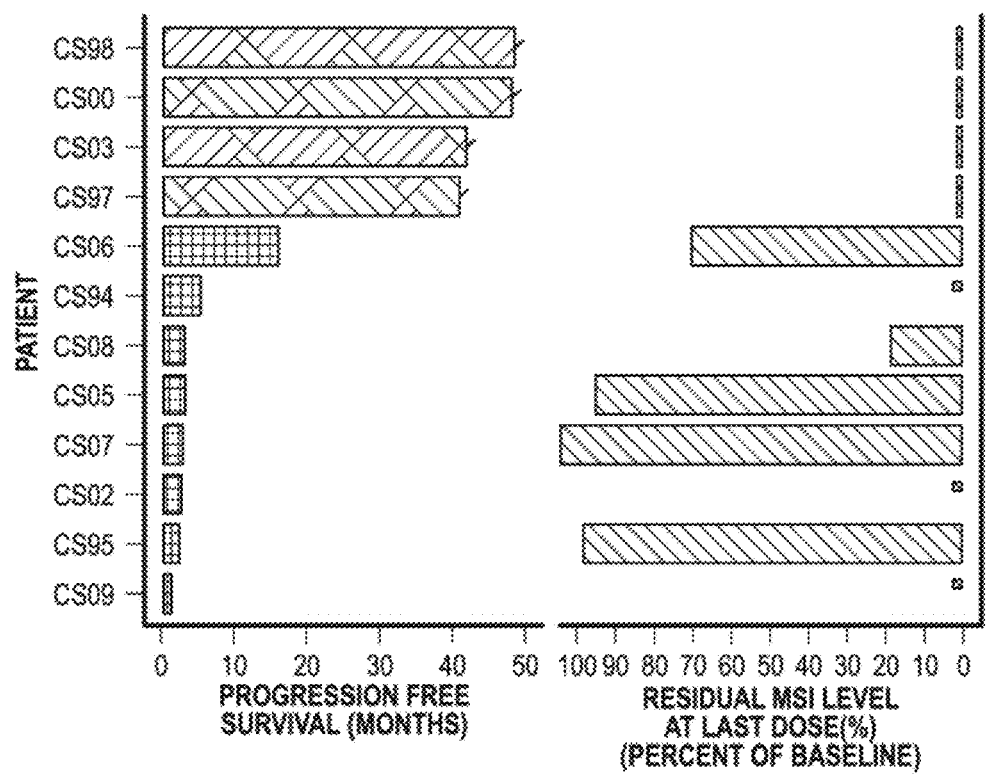
Figure 10D:
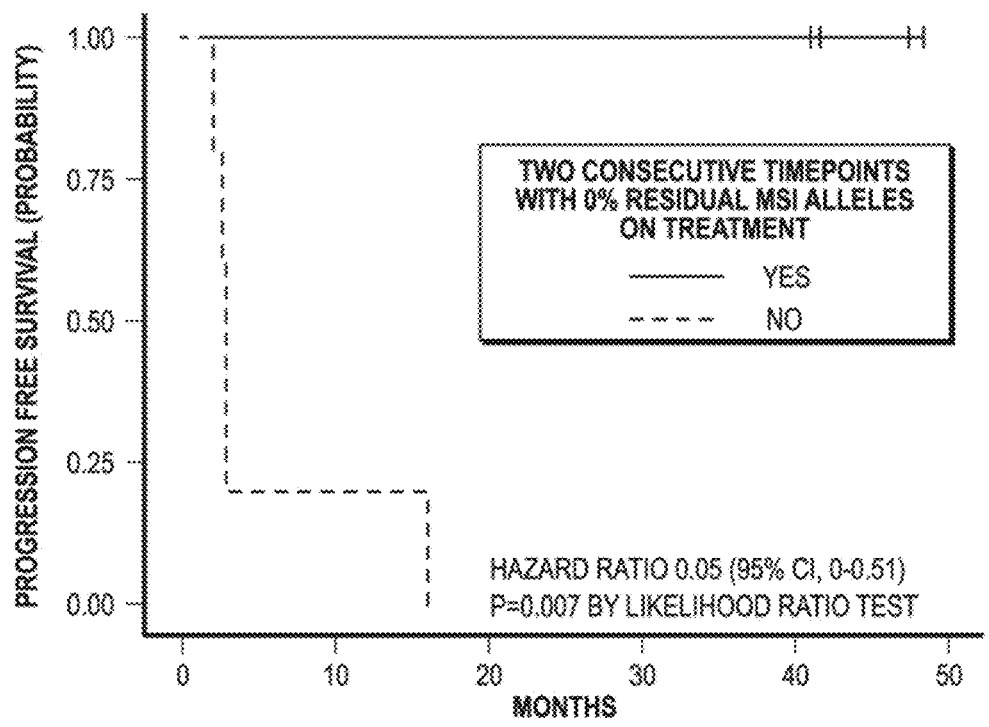
Figure 10E:
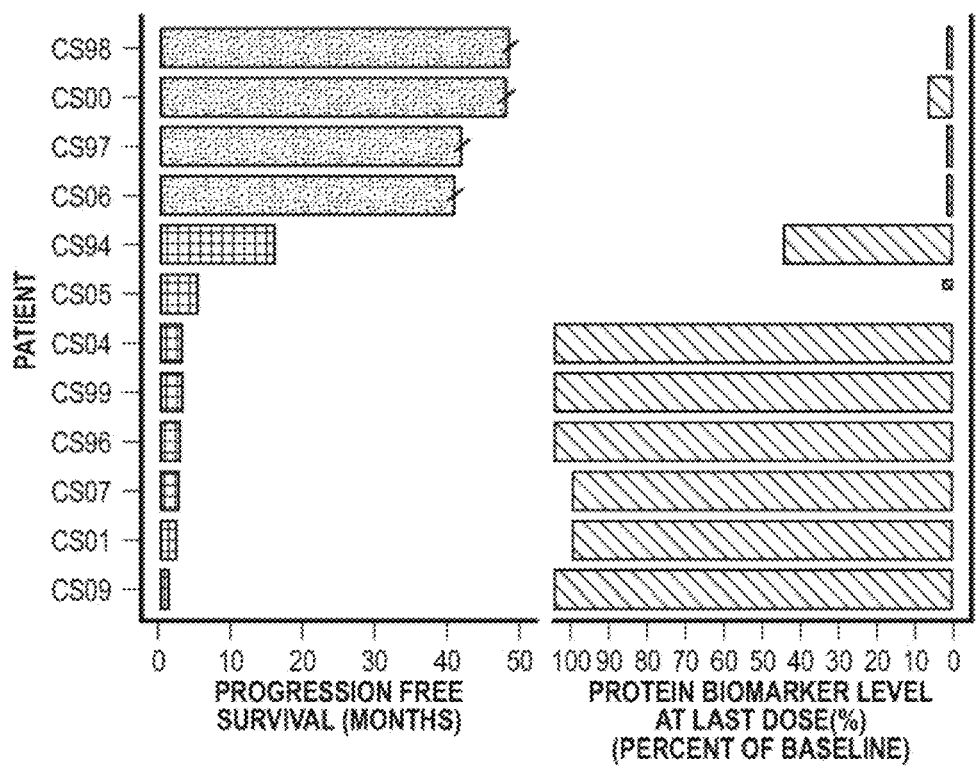
Figure 10F:
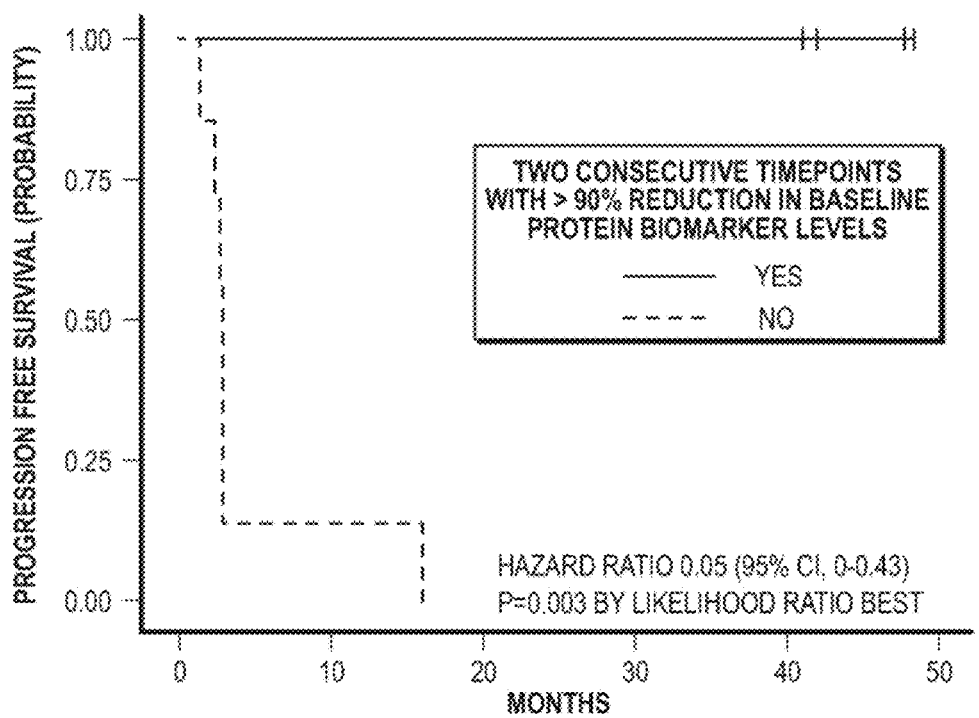

Assessment of Molecular Remission and Biomarker Dynamics in Patients Treated with PD-1 Blockade In addition to baseline plasma analyses, we also hypothesized that the molecular remission, as measured by ctDNA during treatment, would be predictive of long term durable response to immune checkpoint blockade. We first evaluated the utility of monitoring serum tumor protein biomarkers CEA or CA19-9 for determination of response and found that multiple consecutive timepoints with a >80% reduction in the baseline protein biomarker level resulted in improved overall and progression free survival (hazard ratio, 0.05; p=0.01 and hazard ratio, 0.05; p=0.01, likelihood ratio test, respectively) (FIGS. 7A and 7B and FIGS. 10A and 10B). When evaluating the on-treatment serial plasma samples for residual ctDNA levels, there was a significant inverse correlation between the overall and progression free survival when compared to the residual MSI allele levels at last dose (r=−0.70, p=0.034 and r=−0.84, p=0.004, respectively; Pearson correlation) (FIG. 7C and FIG. 10C). We were able to correctly identify four of the six MSI patients who would achieve a long term durable clinical response requiring multiple consecutive on-treatment time points with 0% residual alleles displaying MSI, all four of which displayed a complete response (hazard ratio, 0.09; p=0.032, likelihood ratio test for overall survival) (FIG. 7D and FIG. 10D). A similar trend was observed when considering patients with a >90% decrease in overall TMB across two timepoints when compared to baseline (hazard ratio, 0.07; p=0.013, likelihood ratio test for overall survival) (FIGS. 7E and 7F and FIGS. 10E and 10F).

Additionally, for three patients (CS97, CS98, and CS00) with a complete response to immune checkpoint blockade, and one patient (CS05) without a response to immune checkpoint blockade, circulating protein biomarkers (CEA, ng/mL or CA19-9, units/mL) and residual alleles exhibiting MSI and TMB were evaluated over time during treatment (FIG. 8). In each of the patients exhibiting a complete response, there was a concurrent decrease in the circulating protein biomarker levels, the residual MSI alleles, and TMB levels, which correlated with reduced overall tumor volume as assessed by radiographic imaging. Protein biomarker levels decreased by more than 80% between 1.3 to 2.3 months after first dose. Residual MSI alleles and TMB levels were reduced by >90% between 0.6 and 4.8 months after first dose for these three cases. However, for patient CS05 with progressive disease, the protein biomarker levels remained relatively constant, but there was an increase in residual alleles exhibiting MSI and TMB of 78% and 50%, respectively, at 4.8 months. This correlated with a 13% increase in tumor volume as assessed by radiographic imaging at 5 months.

Figure 11:
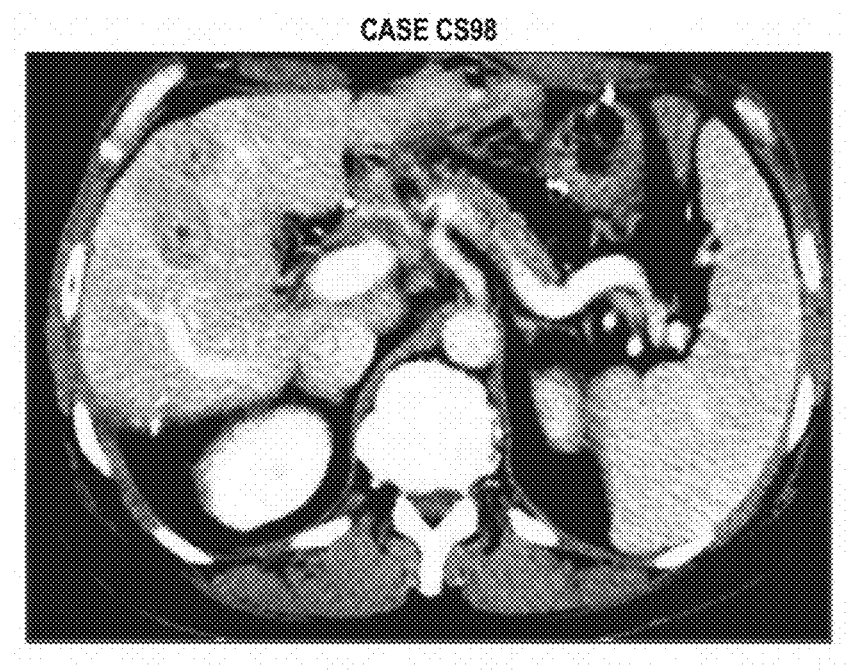
FIG. 11 Radiographic Imaging of Case CS98 Displaying a Complete Response to Immune Checkpoint Blockade. After 20 weeks of treatment with immune checkpoint blockade, radiographic imaging was performed and revealed potential lesions in the liver, but later disappeared, so likely instead represented inflammatory liver nodules.

Patient CS97 demonstrated a partial radiographic response at 10.6 months, however, achieved a 100% reduction in residual MSI and TMB levels at 2.8 months. CS97 then went on to a complete radiographic response at 20.2 months (Table 7). A different patient, CS98, appeared to develop new liver lesions at 20 weeks suggestive of progressive disease (FIG. 11). However, following an initial spike, protein biomarkers and residual MSI and TMB levels demonstrated a biochemical tumor response at 1.3 and 4.8 months. A liver biopsy demonstrated only inflammatory changes in the location where new lesions were noted, suggesting checkpoint therapy induced inflammation. Radiographic imaging finally demonstrated resolution of any hepatic lesions and a 100% reduction in tumor volume at 16.8 months. A similar pattern was observed for patient CS00 where significant reduction in protein biomarker and residual MSI and TMB levels occurred at 1.5 and 0.6 months, respectively, however, radiographic imaging did not demonstrate a 100% reduction in tumor volume until 17 months. These data suggest that the residual MSI allele burden and TMB prognostic signature are indicative of overall tumor response to immune checkpoint blockade.

Discussion

The checkpoint inhibitor pembrolizumab is now indicated for the treatment of adult and pediatric patients with unresectable or metastatic solid tumors identified as having MSI or MMR deficiency (1,2). This represents the first pan-cancer biomarker indication, and now covers patients with solid tumors that have progressed following prior treatment and have no satisfactory alternative treatment options, as well as patients with colorectal cancer that have progressed following treatment with certain chemotherapy drugs. However, it is often not possible to readily obtain biopsy or resection tissue for genetic testing due to insufficient material, exhaustion of the limited material available after prior therapeutic stratification, logistical considerations for tumor and normal sample acquisition after initial diagnosis, or safety concerns related to additional tissue biopsy interventions (26).

We have described the development of a method for simultaneous detection of MSI and TMB-High directly from cfDNA and demonstrated proof of concept for the clinical utility afforded through these analyses for the prediction of response to immune checkpoint blockade. Additionally, given the concordance with circulating protein biomarker data while these patients were on treatment, these data suggest that the residual MSI allele burden and TMB prognostic signature could be applied to other tumor types where standardized protein biomarkers do not exist and may be an earlier predictor of response than radiographic imaging.

These methods described herein provide feasibility for a viable diagnostic approach for screening and monitoring of patients who exhibit MSI or TMB-High and may respond to immune checkpoint blockade.

TABLE 1

125 Gene List for FFPE Tissue Analyses

| Gene (n = 125) | Sequence Mutations (n = 117) | Translocations (n = 29) | Amplifications (n = 41) |
| --- | --- | --- | --- |
| ABL1 | Yes | — | — |
| AKT1 | Yes | — | Yes |
| ALK | Yes | Yes | Yes |
| AR | Yes | — | Yes |
| ATM | Yes | — | — |
| ATRX | Yes | — | — |
| AXL | Yes | Yes | Yes |
| BCL2 | Yes | Yes | Yes |
| BCR | — | Yes | — |

TABLE 1-continued

125 Gene List for FFPE Tissue Analyses

| Gene (n = 125) | Sequence Mutations (n = 117) | Translocations (n = 29) | Amplifications (n = 41) |
| --- | --- | --- | --- |
| BRAF | Yes | Yes | Yes |
| BRCA1 | Yes | Yes | — |
| BRCA2 | Yes | Yes | — |
| CBFB | — | Yes | — |
| CCND1 | Yes | — | Yes |
| CCND2 | Yes | — | Yes |
| CCND3 | Yes | — | Yes |
| CDK4 | Yes | — | Yes |
| CDK6 | Yes | — | Yes |
| CDKN2A | Yes | — | — |
| CHEK2 | Yes | — | — |
| CREBBP | Yes | — | — |
| CSF1R | Yes | — | Yes |
| CTNNB1 | Yes | — | — |
| DDR2 | Yes | — | — |
| DNMT3A | Yes | — | — |
| EGFR | Yes | Yes | Yes |
| EP300 | Yes | — | — |
| EPHA2 | Yes | — | — |
| ERBB2 | Yes | — | Yes |
| ERBB3 | Yes | — | Yes |
| ERBB4 | Yes | — | — |
| ERCC3 | Yes | — | — |
| ERG | Yes | Yes | — |
| ESR1 | Yes | — | — |
| ETV1 | — | Yes | — |
| ETV4 | — | Yes | — |
| ETV5 | — | Yes | — |
| ETV6 | — | Yes | — |
| EWSR1 | — | Yes | — |
| EZH2 | Yes | — | — |
| FANCA | Yes | — | — |
| FANCD2 | Yes | — | — |
| FANCG | Yes | — | — |
| FBXW7 | Yes | — | — |
| FGFR1 | Yes | Yes | Yes |
| FGFR2 | Yes | Yes | Yes |
| FGFR3 | Yes | Yes | Yes |
| FGFR4 | Yes | — | Yes |
| FLT1 | Yes | — | Yes |
| FLT3 | Yes | — | Yes |
| FLT4 | Yes | — | Yes |
| FOXL2 | Yes | — | — |
| GNA11 | Yes | — | — |
| GNAQ | Yes | — | — |
| GNAS | Yes | — | — |
| HDAC2 | Yes | — | — |
| HNF1A | Yes | — | — |
| HRAS | Yes | — | — |
| IDH1 | Yes | — | — |
| IDH2 | Yes | — | — |
| JAK1 | Yes | — | — |
| JAK2 | Yes | — | Yes |
| JAK3 | Yes | — | — |
| KDR | Yes | — | Yes |
| KEAP1 | Yes | — | — |
| KIT | Yes | — | Yes |
| KMT2A | Yes | — | — |
| KRAS | Yes | — | Yes |
| MAP2K1 | Yes | — | — |
| MAP2K2 | Yes | — | — |
| MEN1 | Yes | — | — |
| MET | Yes | — | Yes |
| MLH1 | Yes | — | — |
| MLH3 | Yes | — | — |
| MPL | Yes | — | — |
| MRE11A | Yes | — | — |
| MSH2 | Yes | — | — |
| MSH6 | Yes | — | — |
| MST1R | Yes | — | Yes |
| MTOR | Yes | — | — |
| MYC | Yes | Yes | Yes |
| MYCN | Yes | — | Yes |
| MYD88 | Yes | — | — |
| NBN | Yes | — | — |

TABLE 1-continued

125 Gene List for FFPE Tissue Analyses

| Gene (n = 125) | Sequence Mutations (n = 117) | Translocations (n = 29) | Amplifications (n = 41) |
|---|---|---|---|
| NF1 | Yes | — | — |
| NOTCH1 | Yes | — | — |
| NPM1 | Yes | — | — |
| NRAS | Yes | — | — |
| NTRK1 | Yes | Yes | Yes |
| NTRK2 | Yes | Yes | Yes |
| NTRK3 | Yes | Yes | Yes |
| PALB2 | Yes | — | — |
| PDGFRA | Yes | Yes | Yes |
| PDGFRB | Yes | Yes | Yes |
| PIK3CA | Yes | — | Yes |
| PIK3CB | Yes | — | Yes |
| PIK3R1 | Yes | — | — |
| PMS2 | Yes | — | — |
| POLD1 | Yes | — | — |
| POLE | Yes | — | — |
| PTCH1 | Yes | — | — |
| PTEN | Yes | — | — |
| PTPN11 | Yes | — | — |
| RAD51 | Yes | — | — |
| RAF1 | Yes | Yes | — |
| RARA | Yes | Yes | — |
| RB1 | Yes | — | — |
| RET | Yes | Yes | Yes |
| RNF43 | Yes | — | — |
| ROS1 | Yes | Yes | Yes |
| RUNX1 | Yes | — | Yes |
| SDHB | Yes | — | — |
| SMAD4 | Yes | — | — |
| SMARCB1 | Yes | — | — |
| SMO | Yes | — | — |
| SRC | Yes | — | — |
| STK11 | Yes | — | — |
| TERT | Yes | — | — |
| TET2 | Yes | — | — |
| TMPRSS2 | — | Yes | — |
| TP53 | Yes | — | — |
| TSC1 | Yes | — | — |
| TSC2 | Yes | — | — |
| VEGFA | Yes | — | Yes |
| VHL | Yes | — | — |

TABLE 2

Summary of Next Generation Sequencing Statistics for FFPE Tumor and Matched Normal Samples

| Case ID | Sample Type | Tumor Type | Tumor Purity | Bases Sequenced | Bases Mapped to Genome | Bases Mapped to Targeted Regions of Interest | Average Total Coverage (Fold) | Average Distinct Coverage (Fold) | Orthogonal Promega MSI Analysis System Result | DPF Matched Tumor and Normal Analysis Result | DPF Tumor Only Analysis Result |
|---|---|---|---|---|---|---|---|---|---|---|---|
| T1 | Tumor | Colorectal Cancer | 40% | 3,166,928,200 | 2,938,394,500 | 1,273,077,559 | 1,158 | 927 | MSI-H | MSI-H | MSI-H |
| T2 | Tumor | Colorectal Cancer | 40% | 2,956,194,800 | 2,731,020,900 | 1,118,791,878 | 1,102 | 769 | MSI-H | MSI-H | MSI-H |
| T2 | Tumor | Colorectal Cancer | 80% | 4,620,105,200 | 4,266,153,700 | 1,719,208,838 | 1,705 | 1,151 | MSI-H | MSI-H | MSI-H |
| T4 | Tumor | Colorectal Cancer | 60% | 3,830,551,400 | 3,577,875,700 | 1,587,036,697 | 1,584 | 1,047 | MSI-H | MSI-H | MSI-H |
| T5 | Tumor | Colorectal Cancer | 60% | 3,694,440,800 | 3,417,070,000 | 1,421,110,311 | 1,423 | 1,021 | MSI-H | MSI-H | MSI-H |
| T6 | Tumor | Colorectal Cancer | 70% | 2,781,902,600 | 2,581,541,800 | 1,314,484,935 | 1,308 | 509 | MSI-H | MSI-H | MSI-H |
| T7 | Tumor | Colorectal Cancer | 50% | 2,946,039,800 | 2,766,061,900 | 1,287,341,543 | 1,287 | 870 | MSI-H | MSI-H | MSI-H |
| T8 | Tumor | Colorectal Cancer | 40% | 3,418,941,400 | 3,141,032,200 | 1,134,791,347 | 1,128 | 699 | MSI-H | MSI-H | MSI-H |
| T9 | Tumor | Colorectal Cancer | 60% | 2,554,068,000 | 2,397,514,900 | 1,059,806,697 | 1,065 | 789 | MSI-H | MSI-H | MSI-H |
| T10 | Tumor | Colorectal Cancer | 70% | 2,490,357,800 | 2,325,119,000 | 1,041,133,466 | 1,045 | 577 | MSI-H | MSI-H | MSI-H |
| T11 | Tumor | Colorectal Cancer | 70% | 2,802,989,100 | 2,574,326,700 | 1,021,889,116 | 1,028 | 611 | MSI-H | MSI-H | MSI-H |
| T12 | Tumor | Colorectal Cancer | 60% | 2,732,188,800 | 2,532,625,600 | 1,102,256,555 | 1,106 | 809 | MSS | MSS | MSS |
| T13 | Tumor | Colorectal Cancer | 60% | 3,374,700,400 | 3,160,846,000 | 1,444,383,958 | 1,452 | 856 | MSS | MSS | MSS |
| T14 | Tumor | Colorectal Cancer | 30% | 4,449,316,000 | 4,158,857,900 | 1,912,478,277 | 1,908 | 1,254 | MSS | MSS | MSS |
| T15 | Tumor | Colorectal Cancer | 40% | 3,221,878,600 | 2,990,670,400 | 1,289,363,891 | 1,297 | 984 | MSS | MSS | MSS |
| T16 | Tumor | Colorectal Cancer | 30% | 2,706,508,600 | 2,523,131,100 | 1,106,624,877 | 1,112 | 859 | MSS | MSS | MSS |
| T17 | Tumor | Colorectal Cancer | 25% | 3,251,114,200 | 2,856,483,800 | 961,918,119 | 966 | 736 | MSS | MSS | MSS |
| T18 | Tumor | Colorectal Cancer | 30% | 3,231,913,800 | 3,009,768,900 | 1,360,021,648 | 1,348 | 991 | MSS | MSS | MSS |
| T19 | Tumor | Colorectal Cancer | 25% | 3,363,033,600 | 3,113,118,000 | 1,384,620,931 | 1,376 | 997 | MSS | MSS | MSS |
| T20 | Tumor | Colorectal Cancer | 15% | 2,438,680,600 | 2,276,538,900 | 1,062,441,883 | 1,068 | 664 | MSS | MSS | MSS |
| T21 | Tumor | Colorectal Cancer | 50% | 3,835,047,200 | 3,616,937,100 | 1,599,268,481 | 1,585 | 1,070 | MSS | MSS | MSS |
| T22 | Tumor | Colorectal Cancer | 50% | 3,571,104,800 | 3,364,850,000 | 1,560,304,548 | 1,549 | 1,027 | MSS | MSS | MSS |
| T23 | Tumor | Colorectal Cancer | 50% | 3,358,858,000 | 3,148,152,000 | 1,543,361,455 | 1,531 | 381 | MSS | MSS | MSS |
| T24 | Tumor | Colorectal Cancer | 30% | 3,800,714,600 | 3,454,271,300 | 1,451,100,665 | 1,437 | 1,021 | MSS | MSS | MSS |
| T25 | Tumor | Colorectal Cancer | 70% | 2,786,623,600 | 2,616,808,300 | 1,300,533,976 | 1,308 | 839 | MSS | MSS | MSS |
| T26 | Tumor | Colorectal Cancer | 70% | 2,745,441,000 | 2,560,749,200 | 1,144,854,802 | 1,150 | 831 | MSS | MSS | MSS |
| T27 | Tumor | Colorectal Cancer | 50% | 2,718,178,000 | 2,492,681,200 | 1,007,856,362 | 1,009 | 772 | MSS | MSS | MSS |
| T28 | Tumor | Colorectal Cancer | 50% | 3,811,856,800 | 3,469,104,100 | 1,178,261,647 | 1,164 | 881 | MSS | MSS | MSS |
| T29 | Tumor | Colorectal Cancer | 60% | 2,836,284,200 | 2,619,980,200 | 1,070,525,027 | 1,076 | 803 | MSS | MSS | MSS |
| T30 | Tumor | Colorectal Cancer | 60% | 3,054,498,800 | 2,864,552,700 | 1,219,192,787 | 1,225 | 918 | MSS | MSS | MSS |
| T31 | Tumor | Colorectal Cancer | 80% | 2,580,688,000 | 2,400,044,300 | 974,909,901 | 980 | 778 | MSS | MSS | MSS |
| T32 | Tumor | Colorectal Cancer | 15% | 2,794,799,600 | 2,572,462,100 | 1,100,684,869 | 1,106 | 852 | MSS | MSS | MSS |
| T33 | Tumor | Colorectal Cancer | 25% | 4,145,168,800 | 3,782,601,800 | 1,600,830,943 | 1,581 | 1,023 | MSS | MSS | MSS |
| T34 | Tumor | Colorectal Cancer | 30% | 2,805,656,200 | 2,574,761,000 | 1,165,019,629 | 1,164 | 830 | MSS | MSS | MSS |
| T35 | Tumor | Colorectal Cancer | 25% | 3,314,533,600 | 3,084,210,800 | 1,337,527,973 | 1,324 | 978 | MSS | MSS | MSS |
| T36 | Tumor | Colorectal Cancer | 40% | 3,083,111,800 | 2,855,861,400 | 1,234,493,152 | 1,237 | 871 | MSS | MSS | MSS |
| T37 | Tumor | Colorectal Cancer | 50% | 2,944,656,600 | 2,738,021,600 | 1,185,096,762 | 1,184 | 871 | MSI-H | MSI-H | MSI-H |
| T38 | Tumor | Colorectal Cancer | 50% | 2,753,927,200 | 2,556,267,100 | 1,111,967,617 | 1,107 | 826 | MSI-H | MSI-H | MSI-H |
| T39 | Tumor | Colorectal Cancer | 50% | 2,909,479,000 | 2,736,312,200 | 1,240,864,480 | 1,245 | 880 | MSI-H | MSI-H | MSI-H |

TABLE 2-continued

Summary of Next Generation Sequencing Statistics for FFPE Tumor and Matched Normal Samples

| Case ID | Sample Type | Tumor Type | Tumor Purity | Bases Sequenced | Bases Mapped to Genome | Bases Mapped to Targeted Regions of Interest | Average Total Coverage (Fold) | Average Distinct Coverage (Fold) | Orthogonal Promega MSI Analysis System Result | DPF Matched Tumor and Normal Analysis Result | DPF Tumor Only Analysis Result |
|---|---|---|---|---|---|---|---|---|---|---|---|
| T40 | Tumor | Colorectal Cancer | 50% | 2,861,106,600 | 2,664,312,500 | 1,238,921,489 | 1,135 | 816 | MSI-H | MSI-H | MSI-H |
| T41 | Tumor | Colorectal Cancer | 50% | 3,067,986,400 | 2,803,426,000 | 1,187,719,134 | 1,191 | 807 | MSI-H | MSI-H | MSI-H |
| T42 | Tumor | Colorectal Cancer | 50% | 2,575,126,400 | 2,352,723,700 | 985,780,477 | 986 | 729 | MSI-H | MSI-H | MSI-H |
| T43 | Tumor | Colorectal Cancer | 50% | 3,553,245,200 | 3,291,761,000 | 1,519,022,764 | 1,520 | 569 | MSI-H | MSI-H | MSI-H |
| T44 | Tumor | Colorectal Cancer | 50% | 3,879,433,600 | 3,543,367,700 | 1,412,136,767 | 1,401 | 951 | MSI-H | MSI-H | MSI-H |
| T45 | Tumor | Colorectal Cancer | 50% | 2,906,836,200 | 2,640,548,900 | 1,084,265,479 | 1,083 | 708 | MSI-H | MSI-H | MSI-H |
| T46 | Tumor | Colorectal Cancer | 50% | 3,691,316,800 | 3,373,293,300 | 1,490,830,422 | 1,477 | 633 | MSI-H | MSI-H | MSI-H |
| T47 | Tumor | Colorectal Cancer | 50% | 3,682,074,800 | 3,431,016,500 | 1,578,799,330 | 1,565 | 1,099 | MSI-H | MSI-H | MSI-H |
| T48 | Tumor | Colorectal Cancer | 50% | 3,219,857,800 | 2,968,614,400 | 1,345,719,299 | 1,346 | 953 | MSI-H | MSI-H | MSI-H |
| T49 | Tumor | Colorectal Cancer | 50% | 3,682,200,200 | 3,314,391,200 | 1,446,490,248 | 1,448 | 827 | MSI-H | MSI-H | MSI-H |
| T50 | Tumor | Colorectal Cancer | 50% | 2,698,383,600 | 2,488,106,900 | 1,176,178,010 | 1,178 | 824 | MSI-H | MSI-H | MSI-H |
| T51 | Tumor | Colorectal Cancer | 50% | 3319,692,800 | 2,956,351,200 | 1,252,235,401 | 1,242 | 798 | MSI-H | MSI-H | MSI-H |
| T52 | Tumor | Colorectal Cancer | 50% | 3360,317,400 | 3,095,067,800 | 1,411,042,834 | 1,410 | 1,024 | MSI-H | MSI-H | MSI-H |
| T53 | Tumor | Colorectal Cancer | 25% | 2,961,110,600 | 2,731,451,400 | 1,142,603,080 | 1,149 | 597 | MSI-H | MSI-H | MSI-H |
| T54 | Tumor | Colorectal Cancer | 25% | 2,777,509,400 | 2,589,331,600 | 1,149,189,533 | 1,155 | 769 | MSI-H | MSI-H | MSI-H |
| T53 | Tumor | Colorectal Cancer | 25% | 2,639,198,800 | 2,442,326,100 | 911,827,087 | 916 | 617 | MSS | MSS | MSS |
| T56 | Tumor | Colorectal Cancer | 20% | 2,755,033,400 | 2,531,769,000 | 1,000,935,424 | 1,007 | 681 | MSI-H | MSI-H | MSI-H |
| T57 | Tumor | Colorectal Cancer | 20% | 2,447,814,600 | 2,287,722,900 | 1,015,055,726 | 1,020 | 696 | MSS | MSS | MSS |
| T58 | Tumor | Colorectal Cancer | 20% | 3,286,553,600 | 3,057,086,600 | 1,307,312,335 | 1,314 | 961 | MSS | MSS | MSS |
| T59 | Tumor | Colorectal Cancer | 25% | 2,903,957,600 | 2,684,504,100 | 1,230,635,449 | 1,238 | 569 | MSS | MSS | MSS |
| T60 | Tumor | Colorectal Cancer | 30% | 3,057,011,000 | 2,834,612,800 | 1,299,500,617 | 1,298 | 678 | MSS | MSS | MSS |
| T61 | Tumor | Colorectal Cancer | 30% | 3,524,443,800 | 3,332,286,300 | 1,616,082,336 | 1,617 | 890 | MSI-H | MSI-H | MSI-H |
| N1 | Normal | NA | NA | 1,544,823,000 | 1,450,418,000 | 585,339,892 | 586 | 521 | NA | NA | NA |
| N2 | Normal | NA | NA | 1,902,151,400 | 1,773,538,400 | 686,222,130 | 686 | 604 | NA | NA | NA |
| N3 | Normal | NA | NA | 1,845,286,600 | 1,717,939,600 | 660,169,442 | 663 | 574 | NA | NA | NA |
| N4 | Normal | NA | NA | 1,747,777,400 | 1,604,382,200 | 578,803,459 | 581 | 507 | NA | NA | NA |
| N5 | Normal | NA | NA | 1,358,892,200 | 1,270,257,700 | 532,386,922 | 536 | 466 | NA | NA | NA |
| N6 | Normal | NA | NA | 1,403,909,400 | 1,328,105,100 | 603,030,506 | 606 | 525 | NA | NA | NA |
| N7 | Normal | NA | NA | 1,477,544,600 | 1,386,426,800 | 600,947,522 | 604 | 517 | NA | NA | NA |
| N8 | Normal | NA | NA | 1,922,041,400 | 1,784,316,400 | 701,537,824 | 704 | 613 | NA | NA | NA |
| N9 | Normal | NA | NA | 1,389,792,400 | 1,302,753,500 | 551,063,430 | 556 | 478 | NA | NA | NA |
| N10 | Normal | NA | NA | 1,368,669,200 | 1,282,523,900 | 527,619,827 | 533 | 468 | NA | NA | NA |
| N11 | Normal | NA | NA | 1,124,099,400 | 1,056,703,600 | 434,115,592 | 439 | 390 | NA | NA | NA |
| N12 | Normal | NA | NA | 1,297,100,600 | 1,221,405,100 | 504,944,038 | 510 | 450 | NA | NA | NA |
| N13 | Normal | NA | NA | 1,320,243,600 | 1,222,723,200 | 477,732,672 | 482 | 362 | NA | NA | NA |
| N14 | Normal | NA | NA | 2,096,304,800 | 1,924,550,100 | 629,989,948 | 634 | 563 | NA | NA | NA |
| N15 | Normal | NA | NA | 1,857,918,400 | 1,749,514,000 | 741,540,523 | 745 | 637 | NA | NA | NA |
| N16 | Normal | NA | NA | 1,296,158,400 | 1,225,401,300 | 539,144,010 | 545 | 481 | NA | NA | NA |
| N17 | Normal | NA | NA | 1,172,080,200 | 1,072,384,000 | 351,008,283 | 354 | 321 | NA | NA | NA |
| N18 | Normal | NA | NA | 2,197,386,400 | 2,043,193,200 | 792,440,480 | 793 | 683 | NA | NA | NA |
| N19 | Normal | NA | NA | 1,126,031,600 | 1,057,174,000 | 429,799,839 | 435 | 388 | NA | NA | NA |
| N20 | Normal | NA | NA | 2,203,340,000 | 2,079,985,600 | 923,434,168 | 927 | 780 | NA | NA | NA |
| N21 | Normal | NA | NA | 1,999,881,200 | 1,849,375,700 | 663,902,271 | 666 | 578 | NA | NA | NA |
| N22 | Normal | NA | NA | 1,919,525,200 | 1,795,389,600 | 721,484,943 | 723 | 621 | NA | NA | NA |
| N23 | Normal | NA | NA | 1,331,809,200 | 1,260,705,600 | 596,587,867 | 602 | 517 | NA | NA | NA |
| N24 | Normal | NA | NA | 1,903,783,600 | 1,792,126,800 | 790,507,492 | 792 | 691 | NA | NA | NA |
| N25 | Normal | NA | NA | 1,386,758,000 | 1,304,498,200 | 573,306,885 | 579 | 511 | NA | NA | NA |
| N26 | Normal | NA | NA | 1,288,502,200 | 1,211,465,700 | 518,972,645 | 524 | 465 | NA | NA | NA |
| N27 | Normal | NA | NA | 2,531,366,000 | 2,385,834,400 | 1,019,543,903 | 1,027 | 883 | NA | NA | NA |
| N28 | Normal | NA | NA | 1,992,785,000 | 1,873,292,800 | 802,670,846 | 804 | 687 | NA | NA | NA |
| N29 | Normal | NA | NA | 1,455,104,600 | 1,366,776,900 | 575,386,950 | 581 | 510 | NA | NA | NA |
| N30 | Normal | NA | NA | 1,664,936,200 | 1,561,641,100 | 646,468,058 | 652 | 572 | NA | NA | NA |
| N31 | Normal | NA | NA | 1,200,639,800 | 1,128,641,800 | 463,140,630 | 467 | 416 | NA | NA | NA |
| N32 | Normal | NA | NA | 1,167,761,400 | 1,092,348,500 | 438,958,934 | 442 | 396 | NA | NA | NA |
| N33 | Normal | NA | NA | 1,665,825,400 | 1,541,475,700 | 609,072,888 | 612 | 544 | NA | NA | NA |
| N34 | Normal | NA | NA | 1,367,489,200 | 1,290,133,900 | 556,470,787 | 563 | 499 | NA | NA | NA |
| N35 | Normal | NA | NA | 1,503,631,400 | 1,412,540,500 | 580,358,931 | 585 | 509 | NA | NA | NA |
| N36 | Normal | NA | NA | 1,549,988,400 | 1,458,406,100 | 628,637,957 | 634 | 560 | NA | NA | NA |
| N37 | Normal | NA | NA | 1,568,304,000 | 1,468,430,300 | 616,176,975 | 620 | 519 | NA | NA | NA |
| N38 | Normal | NA | NA | 1,701,739,600 | 1,592,992,100 | 659,495,963 | 662 | 556 | NA | NA | NA |
| N39 | Normal | NA | NA | 1,309,687,400 | 1,234,750,100 | 546,420,462 | 551 | 464 | NA | NA | NA |
| N40 | Normal | NA | NA | 1,712,442,800 | 1,608,493,700 | 702,640,817 | 705 | 588 | NA | NA | NA |
| N41 | Normal | NA | NA | 1,191,012,000 | 1,122,882,200 | 485,771,595 | 491 | 415 | NA | NA | NA |
| N42 | Normal | NA | NA | 2,147,527,600 | 2,012,745,300 | 865,817,634 | 870 | 721 | NA | NA | NA |
| N43 | Normal | NA | NA | 2,632,733,800 | 2,480,587,000 | 1,109,697,317 | 1,120 | 878 | NA | NA | NA |
| N44 | Normal | NA | NA | 1,425,864,600 | 1,323,295,400 | 519,416,405 | 524 | 445 | NA | NA | NA |
| N45 | Normal | NA | NA | 1,155,307,800 | 1,076,440,400 | 436,138,888 | 439 | 377 | NA | NA | NA |
| N46 | Normal | NA | NA | 1,221,955,800 | 1,150,302,700 | 518,176,709 | 523 | 444 | NA | NA | NA |
| N47 | Normal | NA | NA | 1,869,437,000 | 1,735,921,400 | 728,621,647 | 732 | 602 | NA | NA | NA |
| N48 | Normal | NA | NA | 1,587,657,000 | 1,487,987,900 | 631,794,049 | 637 | 537 | NA | NA | NA |

TABLE 2-continued

Summary of Next Generation Sequencing Statistics for FFPE Tumor and Matched Normal Samples

| Case ID | Sample Type | Tumor Type | Tumor Purity | Bases Sequenced | Bases Mapped to Genome | Bases Mapped to Targeted Regions of Interest | Average Total Coverage (Fold) | Average Distinct Coverage (Fold) | Orthogonal Promega MSI Analysis System Result | DPF Matched and Tumor Normal Analysis Result | DPF Tumor Only Analysis Result |
|---|---|---|---|---|---|---|---|---|---|---|---|
| N49 | Normal | NA | NA | 1,781,366,200 | 1,673,812,500 | 729,333,555 | 734 | 619 | NA | NA | NA |
| N50 | Normal | NA | NA | 1,148,277,400 | 1,076,124,300 | 342,181,739 | 346 | 294 | NA | NA | NA |
| N51 | Normal | NA | NA | 1,904,405,800 | 1,764,410,700 | 680,778,768 | 687 | 576 | NA | NA | NA |
| N52 | Normal | NA | NA | 1,640,495,200 | 1,534,588,100 | 662,986,346 | 669 | 549 | NA | NA | NA |
| N53 | Normal | NA | NA | 1,495,963,000 | 1,388,748,600 | 604,616,038 | 612 | 448 | NA | NA | NA |
| N54 | Normal | NA | NA | 1,411,743,800 | 1,318,632,100 | 570,759,302 | 578 | 432 | NA | NA | NA |
| N55 | Normal | NA | NA | 1,254,353,600 | 1,146,429,600 | 439,784,552 | 445 | 346 | NA | NA | NA |
| N56 | Normal | NA | NA | 1,358,890,600 | 1,256,167,000 | 500,055,838 | 506 | 375 | NA | NA | NA |
| N57 | Normal | NA | NA | 1,257,193,000 | 1,177,020,700 | 528,523,113 | 535 | 410 | NA | NA | NA |
| NS8 | Normal | NA | NA | 1,315,380,800 | 1,233,333,300 | 528,722,180 | 535 | 432 | NA | NA | NA |
| N59 | Normal | NA | NA | 1,275,383,800 | 1,172,703,600 | 504,548,697 | 511 | 383 | NA | NA | NA |
| N60 | Normal | NA | NA | 2,296,267,800 | 2,109,785,900 | 916,969,966 | 925 | 645 | NA | NA | NA |
| N61 | Normal | NA | NA | 1,433,371,200 | 1,350,514,800 | 632,414,511 | 639 | 475 | NA | NA | NA |

TABLE 3

Comparison of Microsatellite Status Determined through FFPE Tissue Analyses

| | | Promega MSI Analysis System | |
|---|---|---|---|
| FFPE Tissue Analysis | | MSI-H | MSS |
| 125 Gene Targeted Panel | MSI | 31 | 0 |
| | MSS | 0 | 30 |

TABLE 4

58 Gene List for Plasma Analyses

| Gene (n = 58) | Sequence Region Covered |
|---|---|
| AKT1 | Hot Exon Analysis |
| ALK | Full RefSeq/CCDS Coding Sequence |
| AR | Full RefSeq/CCDS Coding Sequence |
| ATM | Hot Exon Analysis |
| BRAF | Full RefSeq/CCDS Coding Sequence |
| BRCA1 | Hot Exon Analysis |
| BRCA2 | Hot Exon Analysis |
| CCND1 | Hot Exon Analysis |
| CCND2 | Hot Exon Analysis |
| CCND3 | Hot Exon Analysis |
| CD274 | Full RefSeq/CCDS Coding Sequence |
| CDK4 | Full RefSeq/CCDS Coding Sequence |
| CDK6 | Full RefSeq/CCDS Coding Sequence |
| CDKN2A | Hot Exon Analysis |
| CTNNB1 | Hot Exon Analysis |
| DNMT3A | Hot Exon Analysis |
| EGFR | Full RefSeq/CCDS Coding Sequence |
| ERBB2 | Full RefSeq/CCDS Coding Sequence |
| ESR1 | Hot Exon Analysis |
| EZH2 | Hot Exon Analysis |
| FGFR1 | Hot Exon Analysis |
| FGFR2 | Hot Exon Analysis |
| FGFR3 | Hot Exon Analysis |
| FLT3 | Hot Exon Analysis |
| GNAS | Hot Exon Analysis |
| HRAS | Hot Exon Analysis |
| IDH1 | Hot Exon Analysis |
| IDH2 | Hot Exon Analysis |
| JAK2 | Hot Exon Analysis |
| KIT | Full RefSeq/CCDS Coding Sequence |
| KRAS | Full RefSeq/CCDS Coding Sequence |
| MAP2K1 | Kinase Domain |
| MET | Hot Exon Analysis + Adjacent Exon 14 Introns |
| MTOR | Hot Exon Analysis |
| MYC | Hot Exon Analysis |
| MYCN | Hot Exon Analysis |
| NPM1 | Hot Exon Analysis |
| NRAS | Hot Exon Analysis |
| NTRK1 | Hot Exon Analysis |
| NTRK2 | Hot Exon Analysis |
| NTRK3 | Hot Exon Analysis |
| PALB2 | Hot Exon Analysis |
| PIK3CA | Hot Exon Analysis |
| PIK3CB | Hot Exon Analysis |
| PIK3R1 | Hot Exon Analysis |
| POLD1 | Exonuclease Domain |
| POLE | Exonuclease Domain |
| PTCH1 | Hot Exon Analysis |
| PTEN | Hot Exon Analysis |
| RB1 | Hot Exon Analysis |
| RET | Full RefSeq/CCDS Coding Sequence |
| RNF43 | Hot Exon Analysis |
| ROS1 | Kinase and Catalytic Domain |
| TERT | Hot Exon Analysis + Promoter |
| TP53 | Full RefSeq/CCDS Coding Sequence |
| TSC1 | Hot Exon Analysis |
| TSC2 | Hot Exon Analysis |
| VHL | Hot Exon Analysis |

TABLE 5

Summary of Next Generation Sequencing Statistics for Healthy Donor Samples, Contrived Samples, and Clinical Plasma Samples

| Case ID | Sample Type | Bases Sequenced | Bases Mapped to Genome | Bases Mapped to Targeted Regions of Interest | Average Total Coverage (Fold) | Average Distinct Coverage (Fold) | Clinical Tissue Trial Enrollment MSI Status | Plasma MSI Analysis Result | Plasma TMB Analysis Result |
|---|---|---|---|---|---|---|---|---|---|
| HD1 | Healthy Donor | 4,610,602,000 | 4,591,372,800 | 2,313,780,895 | 23,135 | 1,326 | NA | MSS | TMB-Low |
| HD2 | Healthy Donor | 8,891,644,000 | 8,866,148,100 | 4,437,521,303 | 44,386 | 2,567 | NA | MSS | TMB-Low |
| HD3 | Healthy Donor | 5,591,552,000 | 5,569,655,300 | 2,532,932,984 | 25,273 | 1,413 | NA | MSS | TMB-Low |
| HD4 | Healthy Donor | 5,573,545,400 | 5,543,102,100 | 2,255,758,545 | 22,481 | 1,654 | NA | MSS | TMB-Low |
| HD5 | Healthy Donor | 5,207,559,600 | 5,185,499,400 | 2,470,481,571 | 24,671 | 1,860 | NA | MSS | TMB-Low |
| HD6 | Healthy Donor | 6,388,732,200 | 6,377,549,900 | 3,432,543,524 | 34,319 | 3,762 | NA | MSS | TMB-Low |
| HD7 | Healthy Donor | 4,734,677,000 | 4,712,020,800 | 2,345,085,749 | 23,450 | 1,514 | NA | MSS | TMB-Low |
| HD8 | Healthy Donor | 5,302,549,600 | 5,278,776,000 | 2,691,437,847 | 26,923 | 1,141 | NA | MSS | TMB-Low |
| HD9 | Healthy Donor | 7,465,978,000 | 7,443,127,900 | 3,937,377,476 | 39,278 | 2,632 | NA | MSS | TMB-Low |
| HD10 | Healthy Donor | 6,074,039,400 | 6,052,256,300 | 3,176,126,200 | 31,723 | 1,707 | NA | MSS | TMB-Low |
| HD11 | Healthy Donor | 6,213,183,600 | 6,193,263,500 | 3,215,135,348 | 31,924 | 1,629 | NA | MSS | TMB-Low |
| HD12 | Healthy Donor | 7,312,985,200 | 7,287,955,400 | 3,361,626,922 | 33,392 | 2,219 | NA | MSS | TMB-Low |
| HD13 | Healthy Donor | 6,510,483,400 | 6,494,893,800 | 2,976,435,079 | 29,539 | 4,803 | NA | MSS | TMB-Low |
| HD14 | Healthy Donor | 8,627,645,800 | 8,610,309,100 | 4,370,055,158 | 43,159 | 4,240 | NA | MSS | TMB-Low |
| HD15 | Healthy Donor | 8,091,438,800 | 8,070,832,700 | 4,064,773,281 | 40,137 | 2,755 | NA | MSS | TMB-Low |
| HD16 | Healthy Donor | 8,479,048,000 | 8,460,878,600 | 4,274,823,876 | 42,218 | 2,387 | NA | MSS | TMB-Low |
| HD17 | Healthy Donor | 9,956,617,400 | 9,928,487,500 | 4,056,620,966 | 40,013 | 6,204 | NA | MSS | TMB-Low |
| HD18 | Healthy Donor | 8,764,661,800 | 8,741,658,300 | 4,365,489,881 | 43,257 | 1,659 | NA | MSS | TMB-Low |
| HD19 | Healthy Donor | 7,889,783,000 | 7,869,480,500 | 3,564,990,160 | 35,371 | 3,264 | NA | MSS | TMB-Low |
| HD20 | Healthy Donor | 7,633,405,000 | 7,615,920,000 | 3,881,573,734 | 38,491 | 1,890 | NA | MSS | TMB-Low |
| HD21 | Healthy Donor | 7,861,255,200 | 7,840,463,800 | 3,898,962,179 | 38,636 | 1,558 | NA | MSS | TMB-Low |
| HD22 | Healthy Donor | 4,781,596,200 | 4,700,767,800 | 2,047,246,059 | 20,023 | 914 | NA | MSS | TMB-Low |
| HD23 | Healthy Donor | 6,681,047,200 | 6,637,094,200 | 3,496,324,530 | 34,651 | 1,777 | NA | MSS | TMB-Low |
| HD24 | Healthy Donor | 7,177,461,600 | 7,153,542,900 | 3,634,434,110 | 36,048 | 1,926 | NA | MSS | TMB-Low |
| HD25 | Healthy Donor | 7,434,671,400 | 7,407,050,700 | 3,898,804,784 | 38,653 | 2,302 | NA | MSS | TMB-Low |
| HD26 | Healthy Donor | 7,429,101,000 | 7,401,652,100 | 3,673,202,567 | 36,392 | 2,038 | NA | MSS | TMB-Low |
| HD27 | Healthy Donor | 8,503,220,200 | 8,481,220,900 | 4,481,836,913 | 44,189 | 4,007 | NA | MSS | TMB-Low |
| HD28 | Healthy Donor | 7,913,436,400 | 7,891,591,400 | 3,999,331,489 | 39,604 | 6,476 | NA | MSS | TMB-Low |
| HD29 | Healthy Donor | 4,614,537,000 | 4,554,941,500 | 2,105,579,210 | 20,597 | 697 | NA | MSS | TMB-Low |
| HD30 | Healthy Donor | 7,492,256,600 | 7,465,117,200 | 3,476,188,532 | 34,328 | 2,857 | NA | MSS | TMB-Low |
| HD31 | Healthy Donor | 8,328,282,600 | 8,286,892,200 | 4,210,419,884 | 41,650 | 3,095 | NA | MSS | TMB-Low |
| HD32 | Healthy Donor | 7,016,633,400 | 6,995,998,500 | 3,531,038,365 | 34,933 | 1,236 | NA | MSS | TMB-Low |
| HD33 | Healthy Donor | 8,194,639,600 | 8,172,001,600 | 4,176,117,225 | 41,166 | 2,952 | NA | MSS | TMB-Low |
| HD34 | Healthy Donor | 6,007,170,600 | 5,988,709,000 | 2,841,711,258 | 28,277 | 3,526 | NA | MSS | TMB-Low |
| HD35 | Healthy Donor | 7,712,474,800 | 7,687,926,200 | 3,538,858,830 | 34,870 | 3,962 | NA | MSS | TMB-Low |
| HD36 | Healthy Donor | 6,447,382,600 | 6,427,425,700 | 3,393,662,901 | 33,415 | 2,859 | NA | MSS | TMB-Low |

TABLE 5-continued

Summary of Next Generation Sequencing Statistics for Healthy Donor Samples, Contrived Samples, and Clinical Plasma Samples

| Case ID | Sample Type | Bases Sequenced | Bases Mapped to Genome | Bases Mapped to Targeted Regions of Interest | Average Total Coverage (Fold) | Average Distinct Coverage (Fold) | Clinical Tissue Trial Enrollment MSI Status | Plasma MSI Analysis Result | Plasma TMB Analysis Result |
|---|---|---|---|---|---|---|---|---|---|
| HD37 | Healthy Donor | 8,134,672,200 | 8,105,317,200 | 4,054,212,131 | 39,967 | 1,544 | NA | MSS | TMB-Low |
| HD38 | Healthy Donor | 5,535,483,200 | 5,524,427,300 | 2,816,615,357 | 28,054 | 1,983 | NA | MSS | TMB-Low |
| HD39 | Healthy Donor | 7,564,324,200 | 7,546,630,900 | 3,764,230,400 | 37,490 | 4,300 | NA | MSS | TMB-Low |
| HD40 | Healthy Donor | 8,036,286,000 | 8,014,954,300 | 4,048,484,998 | 40,197 | 3,096 | NA | MSS | TMB-Low |
| HD41 | Healthy Donor | 7,640,735,400 | 7,622,537,500 | 3,929,173,586 | 39,049 | 1,971 | NA | MSS | TMB-Low |
| HD42 | Healthy Donor | 6,677,376,600 | 6,656,214,200 | 2,797,826,119 | 27,836 | 1,938 | NA | MSS | TMB-Low |
| HD43 | Healthy Donor | 8,409,420,800 | 8,391,690,200 | 4,451,721,807 | 43,978 | 3,316 | NA | MSS | TMB-Low |
| HD44 | Healthy Donor | 8,467,700,000 | 8,440,226,300 | 3,675,196,602 | 36,497 | 5,083 | NA | MSS | TMB-Low |
| HD45 | Healthy Donor | 7,197,353,200 | 7,170,267,700 | 3,698,926,248 | 36,497 | 1,831 | NA | MSS | TMB-Low |
| HD46 | Healthy Donor | 8,318,236,800 | 8,281,776,900 | 4,148,545,120 | 40,815 | 1,773 | NA | MSS | TMB-Low |
| HD47 | Healthy Donor | 9,006,412,400 | 8,978,934,000 | 4,760,007,319 | 46,907 | 2,891 | NA | MSS | TMB-Low |
| HD48 | Healthy Donor | 7,344,659,400 | 7,321,998,700 | 3,843,864,822 | 37,828 | 1,883 | NA | MSS | TMB-Low |
| HD49 | Healthy Donor | 8,288,914,400 | 8,270,435,900 | 4,445,831,613 | 43,940 | 3,272 | NA | MSS | TMB-Low |
| HD50 | Healthy Donor | 8,639,110,000 | 8,615,224,600 | 4,502,933,702 | 44,423 | 2,244 | NA | MSS | TMB-Low |
| HD51 | Healthy Donor | 7,575,511,200 | 7,555,273,900 | 3,939,210,286 | 39,053 | 3,320 | NA | MSS | TMB-Low |
| HD52 | Healthy Donor | 8,427,667,800 | 8,400,593,500 | 4,420,970,865 | 43,296 | 3,497 | NA | MSS | TMB-Low |
| HD53 | Healthy Donor | 8,542,647,000 | 8,516,087,000 | 4,385,330,122 | 42,944 | 3,771 | NA | MSS | TMB-Low |
| HD54 | Healthy Donor | 8,453,014,000 | 8,428,500,700 | 4,387,819,781 | 43,296 | 2,325 | NA | MSS | TMB-Low |
| HD55 | Healthy Donor | 9,298,955,400 | 9,271,088,500 | 4,819,496,438 | 47,546 | 2,341 | NA | MSS | TMB-Low |
| HD56 | Healthy Donor | 8,478,268,200 | 8,444,312,700 | 4,094,638,378 | 40,360 | 2,050 | NA | MSS | TMB-Low |
| HD57 | Healthy Donor | 8,199,783,400 | 8,170,058,600 | 3,957,778,287 | 39,001 | 2,457 | NA | MSS | TMB-Low |
| HD58 | Healthy Donor | 9,346,566,000 | 9,314,731,900 | 4,924,333,229 | 48,509 | 1,727 | NA | MSS | TMB-Low |
| HD59 | Healthy Donor | 8,919,385,800 | 8,892,662,500 | 4,390,523,968 | 43,293 | 3,513 | NA | MSS | TMB-Low |
| HD60 | Healthy Donor | 8,389,446,000 | 8,370,187,100 | 4,369,738,805 | 43,148 | 1,477 | NA | MSS | TMB-Low |
| HD61 | Healthy Donor | 9,905,663,600 | 9,881,313,200 | 4,974,727,427 | 49,048 | 6,168 | NA | MSS | TMB-Low |
| HD62 | Healthy Donor | 9,174,224,000 | 9,148,992,500 | 4,535,168,624 | 44,655 | 2,138 | NA | MSS | TMB-Low |
| HD63 | Healthy Donor | 8,084,463,600 | 8,057,658,800 | 3,968,831,440 | 38,915 | 1,992 | NA | MSS | TMB-Low |
| HD64 | Healthy Donor | 8,983,082,400 | 8,950,678,700 | 3,826,555,016 | 37,464 | 3,223 | NA | MSS | TMB-Low |
| HD65 | Healthy Donor | 7,442,509,800 | 7,422,697,300 | 3,854,553,775 | 38,261 | 2,341 | NA | MSS | TMB-Low |
| HD66 | Healthy Donor | 8,337,674,200 | 8,316,432,900 | 4,007,211,501 | 39,529 | 2,369 | NA | MSS | TMB-Low |
| HD67 | Healthy Donor | 7,154,104,000 | 7,129,207,200 | 3,440,461,741 | 34,040 | 2,871 | NA | MSS | TMB-Low |
| HD68 | Healthy Donor | 8,659,740,200 | 8,618,184,400 | 4,184,609,095 | 41,321 | 3,957 | NA | MSS | TMB-Low |
| HD69 | Healthy Donor | 7,771,232,400 | 7,753,568,600 | 3,681,096,130 | 36,485 | 3,124 | NA | MSS | TMB-Low |
| HD70 | Healthy Donor | 4,405,077,200 | 4,384,751,000 | 1,552,688,622 | 15,295 | 2,094 | NA | MSS | TMB-Low |
| HD71 | Healthy Donor | 5,920,713,000 | 5,898,405,200 | 2,633,560,458 | 26,073 | 1,061 | NA | MSS | TMB-Low |
| HD72 | Healthy Donor | 7,579,429,200 | 7,554,654,800 | 2,748,860,562 | 27,222 | 2,043 | NA | MSS | TMB-Low |

TABLE 5-continued

Summary of Next Generation Sequencing Statistics for Healthy Donor Samples, Contrived Samples, and Clinical Plasma Samples

| Case ID | Sample Type | Bases Sequenced | Bases Mapped to Genome | Bases Mapped to Targeted Regions of Interest | Average Total Coverage (Fold) | Average Distinct Coverage (Fold) | Clinical Tissue Trial Enrollment MSI Status | Plasma MSI Analysis Result | Plasma TMB Analysis Result |
|---|---|---|---|---|---|---|---|---|---|
| HD73 | Healthy Donor | 8,631,626,800 | 8,607,231,300 | 3,343,564,755 | 33,121 | 3,291 | NA | MSS | TMB-Low |
| HD74 | Healthy Donor | 6,949,033,000 | 6,931,273,900 | 3,127,174,082 | 30,958 | 3,031 | NA | MSS | TMB-Low |
| HD75 | Healthy Donor | 5,875,099,600 | 5,864,389,100 | 2,962,088,150 | 29,390 | 4,277 | NA | MSS | TMB-Low |
| HD76 | Healthy Donor | 6,626,185,400 | 6,609,772,800 | 3,084,072,011 | 30,517 | 2,136 | NA | MSS | TMB-Low |
| HD77 | Healthy Donor | 11,291,302,400 | 11,238,394,500 | 5,110,554,826 | 49,923 | 3,453 | NA | MSS | TMB-Low |
| HD78 | Healthy Donor | 5,515,433,800 | 5,483,434,100 | 1,965,775,908 | 19,120 | 834 | NA | MSS | TMB-Low |
| HD79 | Healthy Donor | 6,954,396,400 | 6,931,242,800 | 3,311,490,206 | 32,327 | 3,145 | NA | MSS | TMB-Low |
| HD80 | Healthy Donor | 6,152,936,200 | 6,131,263,700 | 2,720,849,245 | 26,546 | 2,270 | NA | MSS | TMB-Low |
| HD81 | Healthy Donor | 8,733,434,600 | 8,702,900,400 | 4,271,410,537 | 41,795 | 3,890 | NA | MSS | TMB-Low |
| HD82 | Healthy Donor | 6,720,050,800 | 6,692,163,400 | 2,871,213,549 | 28,127 | 2,200 | NA | MSS | TMB-Low |
| HD83 | Healthy Donor | 7,729,687,400 | 7,705,631,600 | 3,769,457,577 | 37,031 | 3,098 | NA | MSS | TMB-Low |
| HD84 | Healthy Donor | 8,665,550,000 | 8,633,041,400 | 4,135,285,473 | 40,550 | 2,542 | NA | MSS | TMB-Low |
| HD85 | Healthy Donor | 7,972,481,400 | 7,950,462,100 | 3,776,002,282 | 37,290 | 3,000 | NA | MSS | TMB-Low |
| HD86 | Healthy Donor | 8,250,349,800 | 8,215,560,400 | 4,149,026,011 | 40,906 | 2,274 | NA | MSS | TMB-Low |
| HD87 | Healthy Donor | 7,218,789,600 | 7,194,779,100 | 3,266,906,096 | 32,493 | 3,137 | NA | MSS | TMB-Low |
| HD88 | Healthy Donor | 6,682,720,200 | 6,654,240,600 | 3,392,475,194 | 33,738 | 2,498 | NA | MSS | TMB-Low |
| HD89 | Healthy Donor | 6,871,691,000 | 6,856,541,800 | 3,521,282,340 | 34,894 | 2,744 | NA | MSS | TMB-Low |
| HD90 | Healthy Donor | 8,772,448,000 | 8,749,280,600 | 4,178,273,953 | 41,258 | 1,494 | NA | MSS | TMB-Low |
| HD91 | Healthy Donor | 7,480,832,800 | 7,457,217,500 | 3,595,805,873 | 35,471 | 2,266 | NA | MSS | TMB-Low |
| HD92 | Healthy Donor | 5,975,083,600 | 5,958,618,100 | 2,873,989,002 | 28,615 | 1,701 | NA | MSS | TMB-Low |
| HD93 | Healthy Donor | 5,375,821,400 | 5,360,555,500 | 2,567,619,902 | 25,583 | 2,090 | NA | MSS | TMB-Low |
| HD94 | Healthy Donor | 6,280,445,200 | 6,260,287,600 | 3,139,767,399 | 31,191 | 2,533 | NA | MSS | TMB-Low |
| HD95 | Healthy Donor | 8,135,958,600 | 8,115,624,700 | 4,130,225,448 | 40,731 | 2,317 | NA | MSS | TMB-Low |
| HD96 | Healthy Donor | 7,017,152,200 | 7,000,775,900 | 3,355,455,453 | 33,091 | 2,169 | NA | MSS | TMB-Low |
| HD97 | Healthy Donor | 7,423,045,000 | 7,401,835,700 | 3,612,561,174 | 35,619 | 1,489 | NA | MSS | TMB-Low |
| HD98 | Healthy Donor | 7,575,649,400 | 7,542,405,300 | 3,306,732,212 | 32,637 | 1,985 | NA | MSS | TMB-Low |
| HD99 | Healthy Donor | 8,101,683,000 | 8,073,383,300 | 3,916,838,207 | 38,584 | 2,250 | NA | MSS | TMB-Low |
| HD100 | Healthy Donor | 8,227,634,200 | 8,195,376,800 | 3,707,557,242 | 36,571 | 1,908 | NA | MSS | TMB-Low |
| HD101 | Healthy Donor | 7,409,985,800 | 7,378,039,500 | 2,943,037,267 | 29,002 | 1,815 | NA | MSS | TMB-Low |
| HD102 | Healthy Donor | 7,813,906,600 | 7,786,978,900 | 3,615,038,253 | 35,836 | 3,086 | NA | MSS | TMB-Low |
| HD103 | Healthy Donor | 7,127,926,200 | 7,092,785,200 | 2,681,989,940 | 26,428 | 1,720 | NA | MSS | TMB-Low |
| HD104 | Healthy Donor | 7,010,324,000 | 6,980,650,200 | 2,688,769,169 | 26,520 | 1,612 | NA | MSS | TMB-Low |
| HD105 | Healthy Donor | 7,822,779,200 | 7,785,449,900 | 3,212,888,783 | 31,319 | 1,715 | NA | MSS | TMB-Low |
| HD106 | Healthy Donor | 7,364,897,200 | 7,339,416,100 | 3,586,900,299 | 35,320 | 2,452 | NA | MSS | TMB-Low |
| HD107 | Healthy Donor | 8,493,402,800 | 8,458,319,500 | 3,260,053,476 | 32,076 | 3,556 | NA | MSS | TMB-Low |
| HD108 | Healthy Donor | 9,834,233,000 | 9,805,201,200 | 4,706,975,042 | 46,015 | 2,353 | NA | MSS | TMB-Low |

TABLE 5-continued

Summary of Next Generation Sequencing Statistics for Healthy Donor Samples, Contrived Samples, and Clinical Plasma Samples

| Case ID | Sample Type | Bases Sequenced | Bases Mapped to Genome | Bases Mapped to Targeted Regions of Interest | Average Total Coverage (Fold) | Average Distinct Coverage (Fold) | Clinical Tissue Trial Enrollment MSI Status | Plasma MSI Analysis Result | Plasma TMB Analysis Result |
|---|---|---|---|---|---|---|---|---|---|
| HD109 | Healthy Donor | 6,747,679,000 | 6,733,999,600 | 3,110,916,970 | 30,972 | 1,938 | NA | MSS | TMB-Low |
| HD110 | Healthy Donor | 7,069,059,200 | 7,054,426,600 | 3,473,558,000 | 34,223 | 2,862 | NA | MSS | TMB-Low |
| HD111 | Healthy Donor | 10,374,032,800 | 10,334,762,500 | 5,226,977,407 | 51,127 | 3,737 | NA | MSS | TMB-Low |
| HD112 | Healthy Donor | 9,373,668,400 | 9,330,427,800 | 3,826,086,189 | 37,392 | 2,960 | NA | MSS | TMB-Low |
| HD113 | Healthy Donor | 6,510,073,600 | 6,495,529,700 | 3,083,434,125 | 30,646 | 2,714 | NA | MSS | TMB-Low |
| HD114 | Healthy Donor | 5,788,275,000 | 5,775,686,700 | 2,790,114,913 | 27,752 | 1,891 | NA | MSS | TMB-Low |
| HD115 | Healthy Donor | 5,628,781,800 | 5,608,788,400 | 2,324,130,331 | 23,040 | 1,336 | NA | MSS | TMB-Low |
| HD116 | Healthy Donor | 6,622,736,800 | 6,595,711,900 | 2,853,684,669 | 28,019 | 1,732 | NA | MSS | TMB-Low |
| HD117 | Healthy Donor | 8,235,416,200 | 8,206,562,800 | 4,066,198,888 | 40,037 | 2,147 | NA | MSS | TMB-Low |
| HD118 | Healthy Donor | 8,142,539,800 | 8,113,673,000 | 3,498,426,122 | 34,518 | 2,319 | NA | MSS | TMB-Low |
| HD119 | Healthy Donor | 6,567,610,600 | 6,552,480,100 | 3,520,404,897 | 35,102 | 1,423 | NA | MSS | TMB-Low |
| HD120 | Healthy Donor | 8,172,503,000 | 8,146,438,000 | 3,738,973,301 | 36,834 | 2,391 | NA | MSS | TMB-Low |
| HD121 | Healthy Donor | 7,086,855,800 | 7,066,717,300 | 3,531,225,022 | 35,183 | 2,010 | NA | MSS | TMB-Low |
| HD122 | Healthy Donor | 6,632,081,800 | 6,613,761,500 | 2,824,890,605 | 28,087 | 4,498 | NA | MSS | TMB-Low |
| HD123 | Healthy Donor | 8,716,718,200 | 8,692,336,500 | 4,249,954,641 | 42,108 | 2,897 | NA | MSS | TMB-Low |
| HD124 | Healthy Donor | 5,846,065,600 | 5,827,023,000 | 2,398,968,620 | 23,846 | 1,985 | NA | MSS | TMB-Low |
| HD125 | Healthy Donor | 5,987,677,000 | 5,975,740,400 | 3,037,726,557 | 30,200 | 1,896 | NA | MSS | TMB-Low |
| HD126 | Healthy Donor | 6,450,910,600 | 6,433,946,800 | 2,901,586,776 | 28,839 | 1,732 | NA | MSS | TMB-Low |
| HD127 | Healthy Donor | 6,521,277,600 | 6,505,071,200 | 3,237,555,270 | 32,254 | 1,946 | NA | MSS | TMB-Low |
| HD128 | Healthy Donor | 5,183,805,800 | 5,174,096,900 | 2,624,001,866 | 26,114 | 1,626 | NA | MSS | TMB-Low |
| HD129 | Healthy Donor | 6,060,923,800 | 6,032,344,900 | 3,294,503,839 | 33,028 | 2,041 | NA | MSS | TMB-Low |
| HD130 | Healthy Donor | 6,931,215,400 | 6,664,206,100 | 2,861,090,396 | 27,128 | 2,616 | NA | MSS | TMB-Low |
| HD131 | Healthy Donor | 6,881,530,800 | 6,868,642,100 | 3,207,081,669 | 31,800 | 5,415 | NA | MSS | TMB-Low |
| HD132 | Healthy Donor | 8,447,741,200 | 8,422,297,100 | 4,171,378,734 | 41,085 | 2,511 | NA | MSS | TMB-Low |
| HD133 | Healthy Donor | 6,647,519,000 | 6,618,288,100 | 3,015,315,572 | 29,699 | 974 | NA | MSI | TMB-Low |
| HD134 | Healthy Donor | 9,017,435,200 | 8,992,906,300 | 4,677,984,882 | 46,146 | 3,595 | NA | MSS | TMB-Low |
| HD135 | Healthy Donor | 6,184,647,200 | 6,158,774,700 | 2,847,813,354 | 28,060 | 1,659 | NA | MSS | TMB-Low |
| HD136 | Healthy Donor | 7,819,615,400 | 7,794,596,100 | 3,895,863,689 | 38,457 | 2,214 | NA | MSS | TMB-Low |
| HD137 | Healthy Donor | 9,297,185,200 | 9,266,997,400 | 4,986,929,926 | 49,160 | 3,316 | NA | MSS | TMB-Low |
| HD138 | Healthy Donor | 6,088,725,600 | 6,071,004,400 | 2,871,318,994 | 28,468 | 1,376 | NA | MSS | TMB-Low |
| HD139 | Healthy Donor | 7,078,148,600 | 7,064,739,600 | 3,681,471,294 | 36,397 | 3,204 | NA | MSS | TMB-Low |
| HD140 | Healthy Donor | 7,991,284,600 | 7,973,783,500 | 3,998,658,283 | 39,667 | 3,312 | NA | MSS | TMB-Low |
| HD141 | Healthy Donor | 8,078,032,000 | 8,054,876,800 | 4,060,189,135 | 40,087 | 1,762 | NA | MSS | TMB-Low |
| HD142 | Healthy Donor | 7,768,653,400 | 7,744,059,500 | 3,415,300,515 | 33,884 | 1,990 | NA | MSS | TMB-Low |
| HD143 | Healthy Donor | 6,099,199,600 | 6,080,885,000 | 2,775,841,946 | 27,543 | 3,106 | NA | MSS | TMB-Low |
| HD144 | Healthy Donor | 7,710,555,200 | 7,694,753,100 | 3,714,118,122 | 36,768 | 3,794 | NA | MSS | TMB-Low |

TABLE 5-continued

Summary of Next Generation Sequencing Statistics for Healthy Donor Samples, Contrived Samples, and Clinical Plasma Samples

| Case ID | Sample Type | Bases Sequenced | Bases Mapped to Genome | Bases Mapped to Targeted Regions of Interest | Average Total Coverage (Fold) | Average Distinct Coverage (Fold) | Clinical Tissue Trial Enrollment MSI Status | Plasma MSI Analysis Result | Plasma TMB Analysis Result |
|---|---|---|---|---|---|---|---|---|---|
| HD145 | Healthy Donor | 7,799,141,400 | 7,769,239,200 | 3,941,900,921 | 38,944 | 2,524 | NA | MSS | TMB-Low |
| HD146 | Healthy Donor | 6,726,282,600 | 6,712,047,100 | 3,413,345,451 | 33,896 | 2,071 | NA | MSS | TMB-Low |
| HD147 | Healthy Donor | 7,976,941,800 | 7,958,488,700 | 3,953,916,025 | 39,148 | 3,075 | NA | MSS | TMB-Low |
| HD148 | Healthy Donor | 6,773,777,600 | 6,756,376,400 | 3,398,770,425 | 33,685 | 1,878 | NA | MSS | TMB-Low |
| HD149 | Healthy Donor | 7,241,584,800 | 7,214,148,600 | 3,197,797,413 | 31,671 | 1,957 | NA | MSS | TMB-Low |
| HD150 | Healthy Donor | 8,772,019,000 | 8,744,087,400 | 4,198,896,205 | 41,505 | 2,404 | NA | MSS | TMB-Low |
| HD151 | Healthy Donor | 9,597,923,600 | 9,554,309,500 | 4,304,212,463 | 42,013 | 1,918 | NA | MSS | TMB-Low |
| HD152 | Healthy Donor | 9,766,675,200 | 9,730,121,800 | 4,232,551,267 | 41,381 | 2,131 | NA | MSS | TMB-Low |
| HD153 | Healthy Donor | 7,964,424,400 | 7,902,830,700 | 3,958,568,012 | 38,872 | 2,430 | NA | MSS | TMB-Low |
| HD154 | Healthy Donor | 8,703,468,000 | 8,679,744,500 | 4,526,278,703 | 44,722 | 5,251 | NA | MSS | TMB-Low |
| HD155 | Healthy Donor | 7,877,226,800 | 7,859,052,900 | 3,985,810,986 | 39,418 | 3,773 | NA | MSS | TMB-Low |
| HD156 | Healthy Donor | 7,747,095,200 | 7,729,059,800 | 3,978,272,416 | 39,396 | 3,948 | NA | MSS | TMB-Low |
| HD157 | Healthy Donor | 7,689,538,200 | 7,670,324,700 | 3,678,385,491 | 36,403 | 2,146 | NA | MSS | TMB-Low |
| HD158 | Healthy Donor | 6,036,060,400 | 6,021,050,700 | 2,871,615,508 | 28,452 | 1,793 | NA | MSS | TMB-Low |
| HD159 | Healthy Donor | 9,284,331,400 | 9,261,722,300 | 4,572,013,112 | 45,219 | 4,489 | NA | MSS | TMB-Low |
| HD160 | Healthy Donor | 8,039,083,200 | 8,017,829,900 | 3,668,403,298 | 36,433 | 2,958 | NA | MSS | TMB-Low |
| HD161 | Healthy Donor | 6,337,931,000 | 6,315,879,600 | 2,863,889,709 | 28,364 | 1,286 | NA | MSS | TMB-Low |
| HD162 | Healthy Donor | 10,292,765,800 | 10,260,537,400 | 5,291,273,703 | 51,768 | 3,546 | NA | MSS | TMB-Low |
| HD163 | Healthy Donor | 9,258,149,800 | 9,233,715,900 | 4,485,768,075 | 43,995 | 4,143 | NA | MSS | TMB-Low |
| CL1 | LS180 | 7,612,745,000 | 7,589,215,100 | 3,392,459,288 | 33,523 | 2,083 | MSI | MSI | N/A |
| CL2 | LS411N | 7,678,713,000 | 7,654,819,800 | 3,291,800,936 | 32,532 | 2,149 | MSI | MSI | N/A |
| CL3 | SNU-C2B | 6,256,132,400 | 6,240,909,800 | 2,807,306,207 | 27,761 | 2,420 | MSI | MSI | N/A |
| CL4 | RKO | 7,066,840,000 | 7,048,897,500 | 3,177,373,078 | 31,421 | 2,085 | MSI | MSS | N/A |
| CL5 | SNU-C2A | 7,669,517,600 | 7,650,812,200 | 3,439,833,485 | 34,079 | 3,069 | MSI | MSI | N/A |
| CL6 | LS180 | 8,691,502,000 | 8,658,803,000 | 3,445,624,572 | 33,838 | 2,426 | MSI | MSI | N/A |
| CL7 | LS180 | 8,535,101,200 | 8,503,984,000 | 3,893,865,285 | 38,211 | 2,595 | MSI | MSI | N/A |
| CL8 | LS180 | 8,083,764,400 | 8,056,986,800 | 3,780,724,828 | 37,152 | 2,455 | MSI | MSI | N/A |
| CL9 | LS180 | 7,904,478,600 | 7,881,702,700 | 3,696,511,241 | 36,324 | 2,407 | MSI | MSI | N/A |
| CL10 | LS180 | 7,764,828,000 | 7,737,044,900 | 3,531,063,394 | 34,455 | 2,138 | MSI | MSI | N/A |
| CL11 | LS411N | 8,245,419,000 | 8,222,207,200 | 3,748,315,492 | 36,967 | 2,471 | MSI | MSI | N/A |
| CL12 | LS411N | 6,575,842,800 | 6,554,550,700 | 3,030,898,415 | 29,795 | 2,430 | MSI | MSS | N/A |
| CL13 | LS411N | 8,271,559,000 | 8,245,273,600 | 3,762,761,032 | 36,919 | 2,295 | MSI | MSI | N/A |
| CL14 | LS411N | 7,934,153,000 | 7,905,178,000 | 3,458,080,463 | 33,948 | 2,451 | MSI | MSI | N/A |
| CL15 | LS411N | 7,108,328,800 | 7,085,747,100 | 3,057,622,227 | 30,157 | 2,159 | MSI | MSI | N/A |
| CL16 | SNU-C2B | 8,456,505,800 | 8,424,591,600 | 3,925,699,391 | 38,462 | 2,482 | MSI | MSI | N/A |
| CL17 | SNU-C2B | 7,577,529,000 | 7,556,499,800 | 3,380,433,809 | 33,424 | 2,261 | MSI | MSI | N/A |
| CL18 | SNU-C2B | 6,993,859,200 | 6,976,543,600 | 3,225,795,617 | 31,918 | 2,171 | MSI | MSI | N/A |
| CL19 | SNU-C2B | 5,882,123,600 | 5,860,372,800 | 2,447,923,970 | 24,221 | 2,066 | MSI | MSI | N/A |
| CL20 | SNU-C2B | 7,878,616,400 | 7,858,594,100 | 3,506,238,369 | 34,685 | 2,058 | MSI | MSI | N/A |
| CS94P1 | Clinical | 9,263,762,400 | 9,244,770,800 | 3,825,312,992 | 37,868 | 8,416 | MSI | MSI | TMB-Low |
| CS94P2 | Clinical | 8,813,423,000 | 8,792,480,600 | 3,978,488,566 | 39,021 | 8,506 | Timepoint Sample | MSI | N/A |
| CS94P3 | Clinical | 8,964,792,200 | 8,937,833,100 | 3,676,739,247 | 36,159 | 9,963 | Timepoint Sample | MSS | N/A |

TABLE 5-continued

Summary of Next Generation Sequencing Statistics for Healthy Donor Samples, Contrived Samples, and Clinical Plasma Samples

| Case ID | Sample Type | Bases Sequenced | Bases Mapped to Genome | Bases Mapped to Targeted Regions of Interest | Average Total Coverage (Fold) | Average Distinct Coverage (Fold) | Clinical Tissue Trial Enrollment MSI Status | Plasma MSI Analysis Result | Plasma TMB Analysis Result |
|---|---|---|---|---|---|---|---|---|---|
| CS95P1 | Clinical | 7,636,898,200 | 7,570,902,200 | 2,114,468,194 | 20,804 | 2,175 | MSI | MSS | TMB-Low |
| CS95P2 | Clinical | 8,719,884,400 | 8,686,639,300 | 3,776,909,959 | 37,371 | 3,279 | Timepoint Sample | MSS | N/A |
| CS95P3 | Clinical | 7,946,606,600 | 7,923,725,300 | 3,681,799,356 | 36,417 | 3,069 | Timepoint Sample | MSI | N/A |
| CS96P1 | Clinical | 8,340,755,000 | 8,311,711,700 | 3,710,084,604 | 36,690 | 5,686 | MSS | MSS | TMB-Low |
| CS96P2 | Clinical | 6,198,454,200 | 6,168,225,100 | 2,565,799,692 | 24,735 | 5,781 | Timepoint Sample | MSS | N/A |
| CS96P3 | Clinical | 5,912,813,200 | 5,893,031,300 | 2,980,746,401 | 28,844 | 7,161 | Timepoint Sample | MSS | N/A |
| CS97P1 | Clinical | 7,017,701,200 | 6,998,604,600 | 3,287,599,575 | 31,839 | 8,100 | MSI | MSI | TMB-High |
| CS97P2 | Clinical | 7,308,707,000 | 7,285,576,000 | 3,660,108,635 | 35,033 | 8,563 | Timepoint Sample | MSI | N/A |
| CS97P3 | Clinical | 5,469,610,600 | 5,445,096,000 | 2,704,635,549 | 25,902 | 4,807 | Timepoint Sample | MSS | N/A |
| CS97P4 | Clinical | 6,624,844,800 | 6,602,615,600 | 3,295,259,498 | 31,752 | 5,692 | Timepoint Sample | MSS | N/A |
| CS97P5 | Clinical | 7,934,394,400 | 7,916,551,300 | 3,787,601,674 | 36,642 | 7,400 | Timepoint Sample | MSS | N/A |
| CS97P6 | Clinical | 5,527,711,600 | 5,504,889,500 | 2,466,586,812 | 23,568 | 3,104 | Timepoint Sample | MSS | N/A |
| CS98P1 | Clinical | 6,412,760,400 | 6,389,582,100 | 3,056,873,694 | 29,246 | 6,535 | MSI | MSI | TMB-High |
| CS98P2 | Clinical | 6,672,529,200 | 6,656,140,900 | 3,244,885,418 | 31,287 | 6,232 | Timepoint Sample | MSI | N/A |
| CS98P3 | Clinical | 7,239,611,200 | 7,210,354,900 | 3,337,128,346 | 31,960 | 4,571 | Timepoint Sample | MSS | N/A |
| CS98P4 | Clinical | 4,884,469,600 | 4,870,410,300 | 2,398,774,907 | 23,146 | 3,886 | Timepoint Sample | MSS | N/A |
| CS98P5 | Clinical | 6,684,455,800 | 6,629,107,600 | 3,043,981,443 | 29,758 | 2,048 | Timepoint Sample | MSS | N/A |
| CS99P1 | Clinical | 7,515,207,800 | 7,492,829,500 | 3,558,158,353 | 35,107 | 3,567 | MSS | MSS | TMB-Low |
| CS99P2 | Clinical | 7,295,781,200 | 7,266,983,100 | 3,137,279,510 | 30,900 | 2,698 | Timepoint Sample | MSS | N/A |
| CS99P3 | Clinical | 8,069,010,600 | 8,015,635,800 | 3,679,851,982 | 36,047 | 4,776 | Timepoint Sample | MSS | N/A |
| CS99P4 | Clinical | 7,293,700,400 | 7,259,226,900 | 3,264,415,728 | 32,140 | 2,399 | Timepoint Sample | MSS | N/A |
| CS00P1 | Clinical | 6,374,270,600 | 6,354,057,400 | 3,037,772,591 | 29,333 | 4,464 | MSI | MSS | TMB-High |
| CS00P2 | Clinical | 7,800,574,000 | 7,772,352,900 | 3,639,270,013 | 35,789 | 7,769 | Timepoint Sample | MSS | N/A |
| CS00P3 | Clinical | 8,999,308,800 | 8,975,347,800 | 4,386,806,111 | 43,097 | 7,970 | Timepoint Sample | MSS | N/A |
| CS00P4 | Clinical | 8,380,704,400 | 8,356,079,400 | 4,080,252,921 | 40,115 | 6,470 | Timepoint Sample | MSS | N/A |
| CS00P5 | Clinical | 9,582,201,400 | 9,546,328,100 | 3,353,260,614 | 32,916 | 6,017 | Timepoint Sample | MSS | N/A |
| CS00P6 | Clinical | 10,156,844,200 | 10,115,758,100 | 4,837,193,865 | 47,487 | 3,644 | Timepoint Sample | MSS | N/A |
| CS01P1 | Clinical | 8,967,808,600 | 8,936,498,200 | 2,764,042,296 | 27,189 | 7,682 | MSS | MSS | TMB-Low |
| CS01P2 | Clinical | 7,912,113,000 | 7,890,663,500 | 4,022,370,530 | 38,855 | 8,822 | Timepoint Sample | MSS | N/A |
| CS01P3 | Clinical | 6,484,354,600 | 6,455,565,800 | 3,188,722,876 | 30,729 | 7,517 | Timepoint Sample | MSS | N/A |
| CS02P1 | Clinical | 4,189,797,200 | 4,152,277,300 | 1,904,218,928 | 18,244 | 1,223 | MSI | MSS | TMB-Low |
| CS02P2 | Clinical | 10,780,428,800 | 10,746,068,700 | 5,446,642,208 | 52,607 | 4,747 | Timepoint Sample | MSS | N/A |
| CS03P1 | Clinical | 7,050,276,200 | 7,025,996,100 | 3,272,196,914 | 31,585 | 4,411 | MSI | MSI | TMB-High |
| CS03P2 | Clinical | 7,863,350,800 | 7,834,129,600 | 3,881,768,067 | 37,547 | 4,004 | Timepoint Sample | MSS | N/A |
| CS03P3 | Clinical | 5,886,551,400 | 5,855,839,700 | 2,592,954,330 | 25,054 | 1,821 | Timepoint Sample | MSS | N/A |
| CS03P4 | Clinical | 5,120,290,200 | 5,089,916,800 | 2,462,851,445 | 23,841 | 1,370 | Timepoint Sample | MSS | N/A |
| CS04P1 | Clinical | 7,761,417,200 | 7,737,522,100 | 3,680,626,639 | 35,734 | 5,451 | MSS | MSS | TMB-Low |
| CS04P2 | Clinical | 7,248,720,000 | 7,230,958,400 | 3,711,116,296 | 36,019 | 5,988 | Timepoint Sample | MSS | N/A |
| CS04P3 | Clinical | 6,981,545,200 | 6,963,312,600 | 3,392,271,571 | 32,934 | 6,670 | Timepoint Sample | MSS | N/A |
| CS04P4 | Clinical | 8,074,351,200 | 8,052,943,600 | 3,852,185,218 | 37,331 | 8,083 | Timepoint Sample | MSS | N/A |
| CS04P5 | Clinical | 5,970,210,800 | 5,949,218,300 | 2,795,371,329 | 27,047 | 8,641 | Timepoint Sample | MSS | N/A |

TABLE 5-continued

Summary of Next Generation Sequencing Statistics for Healthy Donor Samples, Contrived Samples, and Clinical Plasma Samples

| Case ID | Sample Type | Bases Sequenced | Bases Mapped to Genome | Bases Mapped to Targeted Regions of Interest | Average Total Coverage (Fold) | Average Distinct Coverage (Fold) | Clinical Tissue Trial Enrollment MSI Status | Plasma MSI Analysis Result | Plasma TMB Analysis Result |
|---|---|---|---|---|---|---|---|---|---|
| CS05P1 | Clinical | 5,968,039,800 | 5,946,488,700 | 2,729,734,351 | 26,410 | 5,574 | MSI | MSI | TMB-Low |
| CS05P2 | Clinical | 6,623,933,000 | 6,600,539,800 | 3,226,910,099 | 31,277 | 6,687 | Timepoint Sample | MSI | N/A |
| CS05P3 | Clinical | 4,496,120,400 | 4,477,585,500 | 2,194,338,785 | 21,245 | 3,297 | Timepoint Sample | MSI | N/A |
| CS06P1 | Clinical | 8,211,159,400 | 8,186,988,800 | 4,156,128,019 | 40,389 | 8,002 | MSI | MSI | TMB-High |
| CS06P2 | Clinical | 6,178,650,200 | 6,150,639,400 | 2,894,449,740 | 27,945 | 6,038 | Timepoint Sample | MSI | N/A |
| CS06P3 | Clinical | 6,478,543,800 | 6,455,283,900 | 3,163,299,171 | 30,602 | 4,990 | Timepoint Sample | MSS | N/A |
| CS06P4 | Clinical | 6,548,847,200 | 6,526,980,300 | 3,098,470,879 | 30,056 | 6,184 | Timepoint Sample | MSI | N/A |
| CS06P5 | Clinical | 5,595,054,000 | 5,528,052,700 | 2,505,771,405 | 23,684 | 3,530 | Timepoint Sample | MSI | N/A |
| CS07P1 | Clinical | 10,952,067,600 | 10,913,583,200 | 2,792,942,847 | 27,492 | 8,179 | MSI | MSI | TMB-High |
| CS07P2 | Clinical | 10,529,570,200 | 10,492,696,000 | 4,154,390,112 | 40,862 | 7,298 | Timepoint Sample | MSI | N/A |
| CS07P3 | Clinical | 9,716,580,000 | 9,688,288,100 | 4,626,575,627 | 45,358 | 9,111 | Timepoint Sample | MSI | N/A |
| CS08P1 | Clinical | 6,015,494,400 | 5,979,103,500 | 2,862,781,196 | 27,006 | 7,909 | MSI | MSI | TMB-Low |
| CS08P2 | Clinical | 6,132,402,200 | 6,089,687,400 | 3,043,241,991 | 28,664 | 9,537 | Timepoint Sample | MSI | N/A |
| CS08P3 | Clinical | 6,909,139,800 | 6,867,393,100 | 3,360,042,873 | 31,839 | 7,216 | Timepoint Sample | MSI | N/A |
| CS09P1 | Clinical | 5,711,066,800 | 5,673,140,500 | 2,598,635,892 | 24,508 | 4,781 | MSI | MSS | TMB-Low |
| CS09P2 | Clinical | 6,038,788,400 | 6,017,962,600 | 2,867,990,049 | 27,725 | 6,346 | Timepoint Sample | MSS | N/A |

TABLE 6

Comparison of Microsatellite Status Determined through Healthy Donor, Contrived, and Clinical Plasma Analyses

| Healthy Donors and Contrived Sample Analysis | | Expected Status | |
|---|---|---|---|
| | | MSI-H | MSS |
| 58 Gene Targeted Panel | MSI | 18 | 1 |
| | MSS | 2 | 162 |

| Clinical Plasma Analysis | | Tissue MSI Status | |
|---|---|---|---|
| | | MSI-H | MSS |
| 58 Gene Targeted Panel | MSI | 9 | 0 |
| | MSS | 3 | 4 |

TABLE 7

Summary of Clinical Information for 16 Patients Evaluated for Response to Immune Checkpoint Blockade

| Case ID | Tissue Enrollment MSI Status | Tumor Type | Stage (On Study) | Metastases Detected At Baseline | Lynch Syndrome (Medical History) | Best Response | Time to Best Response (Months) | Time to ORR (Months) | Time to CR (Months) | Duration of Response (Months) |
|---|---|---|---|---|---|---|---|---|---|---|
| CS94 | MSI-H | Ampulla of Vater | IV | Y | Lynch syndrome | PD | N/A | N/A | N/A | N/A |
| CS95 | MSI-H | Small Intestine | IV | Y | Lynch syndrome | PD | N/A | N/A | N/A | N/A |
| CS96 | MSS | Colorectal | IV | Y | No | PD | N/A | N/A | N/A | N/A |
| CS97 | MSI-H | Colorectal | IV | Y | Lynch syndrome | CR | 20.2 | 6.5 | 20.2 | 34.7 |
| CS98 | MSI-H | Colorectal | IV | Y | Lynch syndrome | CR | 16.9 | 12.4 | 16.9 | 36.2 |
| CS99 | MSS | Colorectal | IV | Y | No | PD | N/A | N/A | N/A | N/A |
| CS00 | MSI-H | Ampulla of Vater | IV | Y | Lynch syndrome | CR | 17.1 | 2.4 | 17.0 | 45.4 |
| CS01 | MSS | Colorectal | IV | Y | No | PD | N/A | N/A | N/A | N/A |
| CS02 | MSI-H | Small Intestine | IV | Y | No | PR | 15.2 | 2.6 | N/A | 4.8 |
| CS03 | MSI-H | Colorectal | IV | Y | Lynch syndrome | CR | N/A | 2.9 | 15.2 | 39.1 |
| CS04 | MSS | Colorectal | IV | Y | No | PD | N/A | N/A | N/A | N/A |
| CS05 | MSI-H | Colorectal | IV | Y | Lynch syndrome | PD | N/A | N/A | N/A | N/A |
| CS06 | MSI-H | Colorectal | IV | Y | Lynch syndrome | PR | 2.6 | 2.6 | N/A | 13.6 |
| CS07 | MSI-H | Ampulla of Vater | IV | Y | Lynch syndrome | NE | N/A | N/A | N/A | N/A |
| CS08 | MSI-H | Colorectal | IV | Y | No | PD | N/A | N/A | N/A | N/A |
| CS09 | MSI-H | Colorectal | IV | Y | Unknown | PD | N/A | N/A | N/A | N/A |

| Case ID | Progression Free Survival (Months) | Overall Survival (Months) | Last Dose (Months) | Censored (Progression) | Censored (Overall) | Protein Biomarkers Evaluated | Two Consecutive Timepoints with >80% Reduction in Baseline Protein Biomarker Levels |
|---|---|---|---|---|---|---|---|
| CS94 | 3.0 | 3.6 | 3.0 | 1 | 1 | CEA | No |
| CS95 | 2.8 | 20.7 | 5.6 | 1 | 1 | CEA | N/A - Baseline Normal Reference Range |
| CS96 | 2.8 | 5.0 | 2.4 | 1 | 1 | CEA | No |
| CS97 | 41.2 | 48.8 | 10.6 | 0 | 0 | CEA | Yes |
| CS98 | 48.6 | 48.8 | 23.8 | 0 | 0 | CEA | Yes |
| CS99 | 2.8 | 8.8 | 2.3 | 1 | 1 | CEA | No |
| CS00 | 47.8 | 47.8 | 23.9 | 0 | 0 | CEA; CA19-9 | CEA: N/A - Baseline Normal Reference Range CA19-9: Yes |
| CS01 | 1.7 | 4.9 | 1.8 | 1 | 1 | CEA | No |
| CS02 | 5.5 | 43.9 | 23.6 | 1 | 0 | CEA; CA19-9 | CEA: N/A - Baseline Normal Reference Range CA19-9: N/A - Baseline Normal Reference Range |
| CS03 | 42.0 | 42.0 | 23.8 | 0 | 0 | CEA | N/A - Baseline Normal Reference Range |

TABLE 7-continued

Summary of Clinical Information for 16 Patients Evaluated for Response to Immune Checkpoint Blockade

| | | | | | | | | | |
|---|---|---|---|---|---|---|---|---|---|
| CS04 | 2.9 | 7.6 | 3.8 | | | 1 | | CEA | No |
| CS05 | 2.9 | 15.9 | 4.8 | | | 1 | | CEA | No |
| CS06 | 16.2 | 40.0 | 23.7 | | | 1 | 0 | CEA | No |
| CS07 | 2.4 | 2.4 | 1.4 | | | 1 | | CEA | No |
| CS08 | 3.0 | 7.6 | 3.4 | | | 1 | | CEA | No |
| CS09 | 1.4 | 6.9 | 4.5 | | | 1 | | CEA | N/A - Baseline Normal Reference Range |
| | | | | | | | | | No |

| Case ID | Total Plasma Samples Evaluated | Plasma Time Point 1 (Months) | Plasma Time Point 2 (Months) | Plasma Time Point 3 (Months) | Plasma Time Point 4 (Months) | Plasma Time Point 5 (Months) | Plasma Time Point 6 (Months) | Exome Mutation Load (mutations/Mbp) | Plasma Mutation Load (mutations/Mbp Sequenced) |
|---|---|---|---|---|---|---|---|---|---|
| CS94 | 3 | 0.1 | 0.5 | 3.0 | N/A | N/A | N/A | 23.1 | 40.6 |
| CS95 | 3 | 0.0 | 0.5 | 6.5 | N/A | N/A | N/A | 64.0 | 10.2 |
| CS96 | 3 | 0.0 | 0.5 | 2.8 | N/A | N/A | N/A | 0.1 | 10.2 |
| CS97 | 6 | 0.0 | 0.5 | 2.8 | 10.6 | 12.5 | 22.8 | 70.2 | 111.7 |
| CS98 | 5 | 0.0 | 0.5 | 4.8 | 14.0 | 28.7 | N/A | 120.5 | 203.2 |
| CS99 | 4 | 0.0 | 0.5 | 0.9 | 2.8 | N/A | N/A | N/A | 10.2 |
| CS00 | 6 | 0.0 | 0.6 | 2.9 | 4.4 | 11.7 | 25.9 | 139.2 | 152.4 |
| CS01 | 3 | 0.0 | 0.5 | 0.9 | N/A | N/A | N/A | 2.3 | 20.3 |
| CS02 | 2 | 0.0 | 0.6 | N/A | N/A | N/A | N/A | 40.8 | 0.0 |
| CS03 | 4 | 0.0 | 0.6 | 12.8 | 27.3 | N/A | N/A | 28.2 | 50.8 |
| CS04 | 5 | 0.0 | 0.6 | 1.3 | 2.9 | 4.5 | N/A | 0.8 | 20.3 |
| CS05 | 3 | 0.0 | 0.5 | 4.8 | N/A | N/A | N/A | 39.8 | 10.2 |
| CS06 | 5 | 0.0 | 0.5 | 5.1 | 11.1 | 23.7 | N/A | 11.0 | 91.4 |
| CS07 | 3 | 0.0 | 0.4 | 0.9 | N/A | N/A | N/A | 68.7 | 233.6 |
| CS08 | 3 | 0.0 | 0.7 | 3.0 | N/A | N/A | N/A | N/A | 40.6 |
| CS09 | 2 | 0.0 | 0.7 | N/A | N/A | N/A | N/A | N/A | 20.3 |

TABLE 7-continued

Summary of Clinical Information for 16 Patients Evaluated for Response to Immune Checkpoint Blockade

| Case ID | Time Difference Between Tissue and Plasma Collection (Months) | Average ctDNA Level at Baseline | Baseline Plasma Tumor Mutation Burden Status | Two Consecutive Timepoints with >90% Reduction in TMB Levels on Treatment | Baseline Plasma MSI Status | Two Consecutive Timepoints with 0% Residual MSI Alleles on Treatment |
|---|---|---|---|---|---|---|
| CS94 | 10.6 | 1.3% | TMB-Low | No | MSI-H | No |
| CS95 | 54.0 | 0.4% | TMB-Low | No | MSS | N/A |
| CS96 | 25.3 | 2.3% | TMB-Low | No | MSS | N/A |
| CS97 | 4.9 | 7.1% | TMB-High | Yes | MSI-H | Yes |
| CS98 | 30.3 | 5.5% | TMB-High | Yes | MSI-H | Yes |
| CS99 | N/A | 15.0% | TMB-Low | No | MSS | N/A |
| CS00 | 13.7 | 2.3% | TMB-High | Yes | MSI-H | Yes |
| CS01 | 76.2 | 0.8% | TMB-Low | No | MSS | N/A |
| CS02 | 0.0 | 0.0% | TMB-Low | N/A | MSS | N/A |
| CS03 | 18.5 | 0.5% | TMB-High | Yes | MSI-H | Yes |
| CS04 | 48.8 | 2.3% | TMB-Low | No | MSS | N/A |
| CS05 | 6.2 | 0.7% | TMB-Low | No | MSI-H | No |
| CS06 | 16.3 | 4.6% | TMB-High | No | MSI-H | No |
| CS07 | 16.3 | 7.9% | TMB-High | No | MSI-H | No |
| CS08 | N/A | 7.2% | TMB-Low | No | MSI-H | No |
| CS09 | N/A | 1.1% | TMB-Low | No | MSS | N/A |

TABLE 8

Comparison of Tumor Mutation Burden and Microsatellite Status for Patients Evaluated for Response to Immune Checkpoint Blockade

|  | Tissue | | Plasma | |
| --- | --- | --- | --- | --- |
| Response | MSI-H | MSS | MSI | MSS |
| Complete Response | 4 | 0 | 4 | 0 |
| Partial Response | 2 | 0 | 1 | 1 |
| Progressive Disease | 5 | 4 | 3 | 6 |
| Not Evaluable | 1 | 0 | 1 | 0 |

|  | Tissue | | Plasma | |
| --- | --- | --- | --- | --- |
| Response | TMB-High | TMB-Low | TMB-High | TMB-Low |
| Complete Response | 4 | 0 | 4 | 0 |
| Partial Response | 2 | 0 | 1 | 1 |
| Progressive Disease | 3 | 3 | 0 | 9 |
| Not Evaluable | 1 | 0 | 1 | 0 |

TMB-H is classified as ≥10 mutations/Mbp sequenced for tissue and ≥50.8 mutations/Mbp sequenced for plasma

REFERENCES

1. Le D T, Durham J N, Smith K N, Wang H, Bartlett B R, Aulakh L K, et al. Mismatch repair deficiency predicts response of solid tumors to PD-1 blockade. Science 2017; 357(6349):409-13 doi 10.1126/science.aan6733.
2. Le DT, Uram J N, Wang H, Bartlett B R, Kemberling H, Eyring A D, et al. PD-1 Blockade in Tumors with Mismatch-Repair Deficiency. The New England journal of medicine 2015; 372(26):2509-20 doi 10.1056/NEJMoa1500596.
3. Vogelstein B, Papadopoulos N, Velculescu V E, Zhou S, Diaz L A, Jr., Kinzler K W. Cancer genome landscapes. Science 2013; 339(6127):1546-58 doi 10.1126/science.1235122.
4. Schumacher T N, Schreiber R D. Neoantigens in cancer immunotherapy. Science 2015; 348(6230):69-74 doi 10.1126/science.aaa4971.
5. Segal N H, Parsons D W, Peggs K S, Velculescu V, Kinzler K W, Vogelstein B, et al. Epitope landscape in breast and colorectal cancer. Cancer research 2008; 68(3): 889-92 doi 10.1158/0008-5472.CAN-07-3095.
6. Warthin A. Heredity with reference to carcinoma: As shown by the study of the cases examined in the pathological laboratory of the university of michigan, 1895-1913. Archives of internal medicine 1913; XII (5):546-55 doi 10.100¹/archinte.1913.00070050063006.
7. Lynch H T, Shaw M W, Magnuson C W, Larsen A L, Krush A J. Hereditary factors in cancer. Study of two large midwestern kindreds. Archives of internal medicine 1966; 117(2):206-12.
8. Nicolaides N C, Papadopoulos N, Liu B, Wei Y F, Carter K C, Ruben S M, et al. Mutations of two PMS homologues in hereditary nonpolyposis colon cancer. Nature 1994; 371(6492):75-80 doi 10.1038/371075a0.
9. Hendriks Y M, Wagner A, Morreau H, Menko F, Stormorken A, Quehenberger F, et al. Cancer risk in hereditary nonpolyposis colorectal cancer due to MSH6 mutations: impact on counseling and surveillance. Gastroenterology 2004; 127(1):17-25.
10. Papadopoulos N, Nicolaides N C, Wei Y F, Ruben S M, Carter K C, Rosen C A, et al. Mutation of a mutL homolog in hereditary colon cancer. Science 1994; 263(5153): 1625-9.
11. Bronner C E, Baker S M, Morrison P T, Warren G, Smith L G, Lescoe M K, et al. Mutation in the DNA mismatch repair gene homologue hMLH1 is associated with hereditary non-polyposis colon cancer. Nature 1994; 368(6468): 258-61 doi 10.1038/368258a0.
12. Leach F S, Nicolaides N C, Papadopoulos N, Liu B, Jen J, Parsons R, et al. Mutations of a mutS homolog in hereditary nonpolyposis colorectal cancer. Cell 1993; 75(6):1215-25.
13. Fishel R, Lescoe M K, Rao M R, Copeland N G, Jenkins N A, Garber J, et al. The human mutator gene homolog MSH2 and its association with hereditary nonpolyposis colon cancer. Cell 1993; 75(5):1027-38.
14. Lindblom A, Tannergard P, Werelius B, Nordenskjold M. Genetic mapping of a second locus predisposing to hereditary non-polyposis colon cancer. Nature genetics 1993; 5(3):279-82 doi 10.1038/ng1193-279.
15. Peltomaki P, Aaltonen L A, Sistonen P, Pylkkanen L, Mecklin J P, Jarvinen H, et al. Genetic mapping of a locus predisposing to human colorectal cancer. Science 1993; 260(5109):810-2.
16. Kempers M J, Kuiper R P, Ockeloen C W, Chappuis P O, Hutter P, Rahner N, et al. Risk of colorectal and endometrial cancers in EPCAM deletion-positive Lynch syndrome: a cohort study. The Lancet Oncology 2011; 12(1):49-55 doi 10.1016/S1470-2045(10)70265-5.
17. Hause R J, Pritchard C C, Shendure J, Salipante S J. Classification and characterization of microsatellite instability across 18 cancer types. Nature medicine 2016; 22(11):1342-50 doi 10.1038/nm.4191.
18. Bonneville R, Krook M A, Kautto E A, Miya J, Wing M R, Chen H-Z, et al. Landscape of Microsatellite Instability Across 39 Cancer Types. JCO Precision Oncology 2017 (1):1-15 doi 10.1200/po.17.00073.
19. Murphy K M, Zhang S, Geiger T, Hafez M J, Bacher J, Berg K D, et al. Comparison of the microsatellite instability analysis system and the Bethesda panel for the determination of microsatellite instability in colorectal cancers. The Journal of molecular diagnostics: JMD 2006; 8(3):305-11 doi 10.2353/jmoldx.2006.050092.
20. Niu B, Ye K, Zhang Q, Lu C, Xie M, McLellan M D, et al. MSIsensor: microsatellite instability detection using paired tumor-normal sequence data. Bioinformatics 2014; 30(7):1015-6 doi 10.1093/bioinformatics/btt755.
21. Foltz S M, Liang W W, Xie M, Ding L. MIRMMR: binary classification of microsatellite instability using methylation and mutations. Bioinformatics 2017; 33(23): 3799-801 doi 10.1093/bioinformatics/btx507.
22. Kautto E A, Bonneville R, Miya J, Yu L, Krook M A, Reeser J W, et al. Performance evaluation for rapid detection of pan-cancer microsatellite instability with MANTIS. Oncotarget 2017; 8(5):7452-63 doi 10.18632/oncotarget.13918.
23. Huang M N, McPherson J R, Cutcutache I, Teh B T, Tan P, Rozen S G. MSIseq: Software for Assessing Microsatellite Instability from Catalogs of Somatic Mutations. Scientific reports 2015; 5:13321 doi 10.1038/srep13321.
24. Salipante S J, Scroggins S M, Hampel H L, Turner E H, Pritchard C C. Microsatellite instability detection by next generation sequencing. Clinical chemistry 2014; 60(9): 1192-9 doi 10.1373/clinchem.2014.223677.
25. Ladas I, Yu F, Leong K W, Fitarelli-Kiehl M, Song C, Ashtaputre R, et al. Enhanced detection of microsatellite instability using pre-PCR elimination of wild-type DNA homo-polymers in tissue and liquid biopsies. Nucleic acids research 2018 doi 10.1093/nar/gky251.

26. Tsai E B, Pomykala K, Ruchalski K, Genshaft S, Abtin F, Gutierrez A, et al. Feasibility and Safety of Intrathoracic Biopsy and Repeat Biopsy for Evaluation of Programmed Cell Death Ligand-1 Expression for Immunotherapy in Non-Small Cell Lung Cancer. Radiology 2018; 287(1):326-32 doi 10.1148/radiol.2017170347.
27. Sausen M, Leary R J, Jones S, Wu J, Reynolds C P, Liu X, et al. Integrated genomic analyses identify ARID1A and ARID1B alterations in the childhood cancer neuroblastoma. Nature genetics 2013; 45(1):12-7 doi 10.1038/ng.2493.
28. Leary R J, Kinde I, Diehl F, Schmidt K, Clouser C, Duncan C, et al. Development of personalized tumor biomarkers using massively parallel sequencing. Science translational medicine 2010; 2(20):20ra14 doi 10.1126/scitranslmed.3000702.
29. Forshew T, Murtaza M, Parkinson C, Gale D, Tsui D W, Kaper F, et al. Noninvasive identification and monitoring of cancer mutations by targeted deep sequencing of plasma DNA. Science translational medicine 2012; 4(136):136ra68 doi 10.1126/scitranslmed.3003726.
30. McBride D J, Orpana A K, Sotiriou C, Joensuu H, Stephens P J, Mudie L J, et al. Use of cancer-specific genomic rearrangements to quantify disease burden in plasma from patients with solid tumors. Genes, chromosomes & cancer 2010; 49(11):1062-9 doi 10.1002/gcc.20815.
31. Diehl F, Schmidt K, Choti M A, Romans K, Goodman S, Li M, et al. Circulating mutant DNA to assess tumor dynamics. Nature medicine 2008; 14(9):985-90 doi 10.1038/nm.1789.
32. Dawson S J, Rosenfeld N, Caldas C. Circulating tumor DNA to monitor metastatic breast cancer. The New England journal of medicine 2013; 369(1):93-4 doi 10.1056/NEJMc1306040.
33. Sausen M, Phallen J, Adleff V, Jones S, Leary R J, Barrett M T, et al. Clinical implications of genomic alterations in the tumour and circulation of pancreatic cancer patients. Nature communications 2015; 6:7686 doi 10.1038/ncomms8686.
34. Phallen J, Sausen M, Adleff V, Leal A, Hruban C, White J, et al. Direct detection of early-stage cancers using circulating tumor DNA. Science translational medicine 2017; 9(403) doi 10.1126/scitranslmed.aan2415.
35. Ellrott K, Bailey M H, Saksena G, Covington K R, Kandoth C, Stewart C, et al. Scalable Open Science Approach for Mutation Calling of Tumor Exomes Using Multiple Genomic Pipelines. Cell systems 2018; 6(3):271-81 e7 doi 10.1016/j.cels.2018.03.002.
36. Jones S, Anagnostou V, Lytle K, Parpart-Li S, Nesselbush M, Riley D R, et al. Personalized genomic analyses for cancer mutation discovery and interpretation. Science translational medicine 2015; 7(283):283ra53 doi 10.1126/scitranslmed.aaa7161.
37. Li H, Durbin R. Fast and accurate short read alignment with Burrows-Wheeler transform. Bioinformatics 2009; 25(14):1754-60 doi 10.1093/bioinformatics/btp324.
38. Li H, Handsaker B, Wysoker A, Fennell T, Ruan J, Homer N, et al. The Sequence Alignment/Map format and SAMtools. Bioinformatics 2009; 25(16):2078-9 doi 10.1093/bioinformatics/btp352.
39. Xie M, Lu C, Wang J, McLellan M D, Johnson K J, Wendl M C, et al. Age-related mutations associated with clonal hematopoietic expansion and malignancies. Nature medicine 2014; 20(12):1472-8 doi 10.1038/nm.3733.

Any and all references and citations to other documents, such as patents, patent applications, patent publications, journals, books, papers, web contents, that have been made throughout this disclosure are hereby incorporated herein by reference in their entirety for all purposes.

Although the present invention has been described with reference to specific details of certain embodiments thereof in the above examples, it will be understood that modifications and variations are encompassed within the spirit and scope of the invention. Accordingly, the invention is limited only by the following claims.

The invention claimed is:

1. A method of determining microsatellite instability (MSI) status comprising:
   (a) capturing target cell free DNA (cfDNA) from a liquid sample from a patient, wherein the liquid sample is from blood, serum, plasma, urine, saliva or other biological fluid;
   (b) attaching a plurality of sets of non-unique exogenous barcodes to the cfDNA so that each cfDNA molecule is attached to a non-unique exogenous barcode;
   (c) amplifying the cfDNA from (b) to produce amplicons that include barcode information and copies of the cfDNA molecules;
   (d) sequencing the amplicons to obtain sequences of a plurality of tracts of nucleotide repeats, wherein the obtained sequences include a plurality of sequence reads;
   (e) identifying groups of sequence reads that originated from each unique cfDNA molecule by means of the barcode information and position or content of the sequence reads;
   (f) performing a first alignment of the plurality of sequence reads from (e) with a reference sequence, wherein the reference sequence comprises a human genome;
   (g) identifying a subset of the sequence reads aligning with microsatellite alleles in the reference sequence;
   (h) performing a second alignment on the subset of sequence reads from (g) with their respective microsatellite alleles in the reference sequence to determine indel length for each sequence read within the subset;
   (i) aggregating groups of sequence reads according to the first and second alignment;
   (j) performing error correction using the non-unique exogenous barcodes on the aggregated groups of sequence reads from (i) which comprise at least 2 sequence reads and wherein more than 50% of those sequence reads comprise identical nucleotide repeat lengths;
   (k) identifying local peaks from a length distribution plot of nucleotide repeat lengths from each aggregated group of corrected sequence reads from (j); and
   (l) determining if the length of a microsatellite allele corresponding to a local peak from (k) is 3 or more base pairs shorter than the length of the corresponding microsatellite allele in the reference sequence, wherein local peaks which are 3 or more base pairs shorter than the length of the corresponding microsatellite allele in the reference sequence are determined to have MSI;
   thereby determining MSI status.

2. The method of claim 1, wherein the reference sequence is from a matched normal DNA sample.

3. The method of claim 1, wherein the microsatellite alleles include one or more of BAT25, BAT26, MONO-27, NR21, NR24, Penta C, and Penta D.

4. The method of claim 1, wherein the microsatellite alleles include BAT25, BAT26, MONO-27, NR21, and NR24.

5. The method of claim 1, further comprising recommending a treatment for the patient based on the MSI status.

6. The method of claim 5, wherein the MSI status indicates that the patient is microsatellite instable and the treatment comprises an immune checkpoint inhibitor.

7. The method of claim 1, further comprising administering an immune checkpoint inhibitor to the patient.

8. The method of claim 7, wherein the immune checkpoint inhibitor comprises an antibody.

9. The method of claim 8, wherein the antibody is selected from the group consisting of: an anti-PD-1 antibody; an anti-IDO antibody; an anti-CTLA-4 antibody; an anti-PD-L1 antibody; and an anti-LAG-3 antibody.

10. The method of claim 1, wherein the sequencing is next-generation, short-read sequencing.

11. The method of claim 1, wherein the liquid sample is from plasma.

12. The method of claim 1, wherein the microsatellite alleles comprise a mononucleotide repeat.

13. The method of claim 1, wherein the method is used in screening for Lynch syndrome.

14. The method of claim 1, wherein the patient has a cancer selected from pancreatic, colon, gastric, endometrial, cholangiocarcinoma, breast, lung, head and neck, kidney, bladder, prostate cancer, or hematopoietic cancers.

15. A method for generating a personalized cancer treatment report for a patient having or suspected of having cancer, the method comprising:
(a) capturing target cell free DNA (cfDNA) from a liquid sample from a patient, wherein the liquid sample is from blood, serum, plasma, urine, saliva or other biological fluid;
(b) attaching a plurality of sets of non-unique exogenous barcodes to the cfDNA so that each cfDNA molecule is attached to a non-unique exogenous barcode;
(c) amplifying the cfDNA from (b) to produce amplicons that include barcode information and copies of the cfDNA molecules;
(d) sequencing the amplicons to obtain sequences of a plurality of tracts of nucleotide repeats, wherein the obtained sequences include a plurality of sequence reads;
(e) identifying groups of sequence reads that originated from each unique cfDNA molecule by means of the barcode information and position or content of the sequence reads;
(f) performing a first alignment of the plurality of sequence reads from (e) with a reference sequence, wherein the reference sequence comprises a human genome;
(g) identifying a subset of the sequence reads aligning with microsatellite alleles in the reference sequence;
(h) performing a secondary alignment on the subset of sequence reads from (g) with their respective microsatellite alleles in the reference sequence, to determine indel length for each sequence read within the subset;
(i) aggregating groups of sequence reads according to the first and second alignment;
(j) performing error correction using the non-unique exogenous barcodes on the aggregated groups of sequence reads from (i) which comprise at least 2 sequence reads and wherein more than 50% of those sequence reads comprise identical nucleotide repeat lengths;
(k) identifying local peaks from a length distribution plot of nucleotide repeat lengths from each aggregated group of corrected sequence reads from (j); and
(l) determining if the length of the microsatellite allele corresponding to a local peak from (k) is 3 or more base pairs shorter than the length of the corresponding microsatellite allele in the reference sequence,
wherein local peaks which are 3 or more base pairs shorter than the length of the corresponding microsatellite allele in the reference sequence are determined to have MSI; and
generating a personalized cancer treatment report.

16. The method of claim 15, wherein the cancer treatment report comprises one or more of the following: (i) information on prognosis, resistance, or potential therapeutic options; (ii) information on the likely effectiveness of a therapeutic option; (iii) the acceptability of a therapeutic option, or the advisability of applying the therapeutic option to the subject; or (iv) information on the administration of a drug.

17. The method of claim 15, wherein the patient has a cancer selected from pancreatic, colon, gastric, endometrial, cholangiocarcinoma, breast, lung, head and neck, kidney, bladder, prostate cancer, or hematopoietic cancers.

18. A method of determining the prognosis or therapeutic regimen for a patient having cancer comprising:
(a) capturing target cell free DNA (cfDNA) from a liquid sample from a patient, wherein the sample is from blood, serum, plasma, urine, saliva or other biological fluid;
(b) attaching a plurality of sets of non-unique exogenous barcodes to the cfDNA so that each cfDNA molecule is attached to a non-unique barcode;
(c) amplifying the cfDNA from (b) to produce amplicons that include barcode information and copies of the cfDNA molecules;
(d) sequencing the amplicons to obtain sequences of a plurality of tracts of nucleotide repeats, wherein the obtained sequences include a plurality of sequence reads;
(e) identifying groups of sequence reads that originated from each unique cfDNA molecule by means of the barcode information and position or content of the sequence reads;
(f) performing a first alignment of the plurality of sequence reads from (e) with a reference sequence, wherein the reference sequence comprises a human genome;
(g) identifying a subset of the sequence reads aligning with microsatellite alleles in the reference sequence;
(h) performing a secondary alignment on the subset of sequence reads from (g) with their respective microsatellite alleles in the reference sequence, to determine indel length for each sequence read within the subset;
(i) aggregating groups of sequence reads according to the first and second alignment;
(j) performing error correction using the non-unique exogenous barcodes on the aggregated groups of sequence reads from (i) which comprise at least 2 sequence reads and wherein more than 50% of those sequence reads comprise identical nucleotide repeat lengths;
(k) identifying local peaks from a length distribution plot of nucleotide repeat lengths from each aggregated group of corrected sequence reads from (j); and
(l) determining if the length of the microsatellite allele corresponding to a local peak from (k) is 3 or more base pairs shorter than the length of the corresponding microsatellite allele in the reference sequence, wherein local peaks which are 3 or more base pairs shorter than the length of the corresponding microsatellite allele in the reference sequence are determined to have MSI; and determining a prognosis or therapeutic regimen for the patient based on the MSI status for each microsatellite allele.

19. The method of claim 18, wherein the reference sequence is from a matched normal DNA sample.

20. The method of claim 18, wherein the microsatellite alleles include one or more of BAT25, BAT26, MONO-27, NR21, NR24, Penta C, and Penta D.

21. The method of claim 18, wherein the microsatellite alleles include BAT25, BAT26, MONO-27, NR21, and NR24.

22. The method of claim 18, further comprising administering an immune checkpoint inhibitor to the patient.

23. The method of claim 22, wherein the immune checkpoint inhibitor is selected from the group consisting of: an anti-PD-1 antibody; an anti-IDO antibody; an anti-CTLA-4 antibody; an anti-PD-L1 antibody; and an anti-LAG-3 antibody.

24. The methods of any one of claim 1, 15 or 18, wherein the MSI status is determined within a specificity of >99% and a sensitivity of 75%.

25. The method of claim 24, wherein the liquid sample has a tumor fraction of <5%.

26. The method of claim 24, wherein the liquid sample has a tumor fraction of 0.5-7.9%.

27. The method of any one of claims 1, 15 or 18, wherein local peaks comprise:

(a) a greater number of sequences reads as compared to the number of sequence reads adjacent to the local peak at each individual length within ±2 bp in the length distribution plot, (b) more than 3 distinct fragments having the same length, and (c) more than 1% absolute coverage of a microsatellite sequence in the reference.

28. The methods of any one of claim 1, 15 or 18, wherein the reference genome is the human genome assembly hg19.

29. A method of determining microsatellite instability (MSI) status comprising:

(a) capturing target cell free DNA (cfDNA) from a liquid sample from a patient, wherein the liquid sample is from blood, serum, plasma, urine, saliva or other biological fluid;

(b) attaching a plurality of sets of non-unique exogenous barcodes to the cfDNA so that each cfDNA molecule is attached to a non-unique exogenous barcode;

(c) amplifying the fragments to produce amplicons that include barcode information and copies of the cfDNA molecules;

(d) sequencing the amplicons to obtain sequences of a plurality of tracts of nucleotide repeats, wherein the obtained sequences include a plurality of sequence reads;

(e) identifying groups of sequence reads that originated from each unique cfDNA molecule by means of the barcode information and position or content of the sequence reads;

(f) performing a first alignment of the plurality of sequence reads from (e) with a reference sequence, wherein the reference sequence comprises a human genome;

(g) identifying a subset of the sequence reads aligning with microsatellite alleles in the reference sequence, and which further comprise:

(i) a nucleotide repeat beginning >8 bp after the start of the sequence read and ending >8 bp from the end of the sequence read, (ii) an insertion or deletion (indel) comprising 12 or less bases compared to the reference, (iii) the absence of a single base change within the nucleotide repeat, and (iv) a mapping score of 60, and (v) 20 or less soft clipped bases;

(h) performing a secondary alignment on the subset of sequence reads from (g) with their respective microsatellite alleles in the reference sequence, to determine indel length for each sequence read within the subset;

(i) aggregating groups of sequence reads within the subset of sequence reads according to the first alignment from (f), the second alignment from (h), and alignment of non-unique exogenous barcodes;

(j) performing error correction using the non-unique exogenous barcodes on the aggregated groups of sequence reads from (i) which comprise at least 2 sequence reads and wherein more than 50% of those sequence reads comprise identical nucleotide repeat lengths;

(k) identifying local peaks from a length distribution plot of nucleotide repeat lengths from each aggregated group of corrected sequence reads from (j); and (l) determining if the length of the microsatellite allele corresponding to a local peak from (k) is 3 or more base pairs shorter than the length of the corresponding microsatellite allele in the reference sequence, wherein local peaks which are 3 or more base pairs shorter than the length of the corresponding microsatellite allele in the reference sequence are determined to have MSI, wherein MSI status is determined within a specificity of >99% and a sensitivity of 75%, and thereby determining microsatellite instability (MSI) status.

30. The method of claim 29, wherein the liquid sample has a tumor fraction of <5%.

31. The method of claim 29, wherein the liquid sample has a tumor fraction of 0.5-7.9%.

32. The method of claim 29, wherein the human genome is the human genome assembly hg19.

* * * * *